(12) United States Patent
Dixon et al.

(10) Patent No.: US 7,622,638 B2
(45) Date of Patent: Nov. 24, 2009

(54) GENETIC MANIPULATION OF CONDENSED TANNINS

(75) Inventors: Richard A. Dixon, Ardmore, OK (US); Nancy L. Paiva, Ardmore, OK (US); Deyu Xie, Ardmore, OK (US); Shashi Sharma, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 1067 days.

(21) Appl. No.: 10/610,351

(22) Filed: Jun. 30, 2003

(65) Prior Publication Data

US 2004/0093632 A1 May 13, 2004

Related U.S. Application Data

(60) Provisional application No. 60/392,562, filed on Jun. 28, 2002.

(51) Int. Cl.
*A01H 5/00* (2006.01)
*A01H 5/10* (2006.01)
*A01H 1/00* (2006.01)
*C12N 15/82* (2006.01)
*C12N 15/53* (2006.01)

(52) U.S. Cl. .................... 800/298; 536/23.2; 800/282; 800/260; 435/41

(58) Field of Classification Search .................. 800/295, 800/278, 282, 317.3; 435/69.1, 91.4, 468, 435/183; 530/350, 370; 536/23.1, 23.6
See application file for complete search history.

(56) References Cited

U.S. PATENT DOCUMENTS

| | | | |
|---|---|---|---|
| 7,098,011 B1 | 8/2006 | Fader et al. ................. | 435/183 |
| 7,189,895 B2 | 3/2007 | McGonigle et al. ......... | 800/278 |
| 2004/0045049 A1 | 3/2004 | Zhang et al. ................. | 800/278 |
| 2004/0093632 A1 | 5/2004 | Dixon et al. ................. | 800/278 |
| 2004/0103458 A1 | 5/2004 | Johnson et al. ............. | 800/284 |
| 2006/0123508 A1 | 6/2006 | Dixon et al. ................. | 800/278 |

FOREIGN PATENT DOCUMENTS

| | | |
|---|---|---|
| WO | WO 02/066625 A1 | 8/2002 |
| WO | WO 03/031622 | 4/2003 |
| WO | WO 03/040306 | 5/2003 |
| WO | WO 03/093464 | 11/2003 |
| WO | WO 2004/090136 | 10/2004 |

OTHER PUBLICATIONS

Stevens et al (1995) Distribution of Alkaloids and Tannins in the Crassulaceae Biochemical Systematics and Ecology 23:157-165.*
Devic et al, (1999) The Banyuls gene encodes a DFR-like protein and is a marker of early seed coat development The Plant J. 19:387-398.*
Van De Loo et al (1995) An Oleate 12-Hydroxylase From *Ricinus communis* L. Is A Fatty Acyl Desaturase Homolog. P.N.A.S. 92:6743-47.*
Broun, et al (1998) Catalytic Plasticity Of Fatty Acid Modification Enzymes Underlying Chemical Diversity Of Plant Lipids. Science 282(13) 1315-1317.*
Schijlen et al. (2004) Phytochemistry 65 (2004) 2631-2648.*
Dixon, et al (2005) *Proanthocyanidinds*—A Final Frontier in Flavonoid Research? New Phytologist 165: 9-28.*
Sharma, & Dixon, (2005) Metabolic engineering of proanthocyanidins by ectopic expression of transcription factors in *Arabidopsis thaliana* The Plant Journal, 44: 62-75.*
Xie, et al (2003) Role of *Anthocyanidin reductase*, encoded by Banyuls in plant flavonoid biosynthesis. Science, 299, 396-399.*
Alberts Plant J. (1997) 11(2) 289-299.*
Sharma. & Dixon, (2005) Metabolic engineering of *Proanthocyanidins* by ectopic expression of transcription factors in *Arabidopsis thaliana* The Plant Journal, 44: 62-75.*
Xie, et al (2004) Archives of Biochem. Biophys. 422:91-102.*
Skadhauge et al (1997, Amer. J. Bot. 84:494-503).*
Devic et al (1999, Plant J. 19:387-398).*
Albert et al., "Banyuls, a novel negative regulator of flavinoid biosynthesis in the *Arabidopsis* seed coat," *The Plant Journ.*, 11:289-299, 1997.
Borevitz et al., "Activation tagging identifies a conserved MYB regulator of phenylpropanoid biosynthesis," *Plant Cell*, 12:2383-2393, 2000.
Clough and Bent, "Floral dip: a simplified method for agrobacterium-mediated transformation of *Arabidopsis thalia*," *Plant J.*, 16:735-743, 1998.
Dalzell and Kerven, "A rapid method for the measurement of *Leucaena* spp *proanthocyanidins* by the *Proanthocyanidin*," *J. Sci. Food Agric.*, 78:405-416, 1998.
Debeaujon et al., "The Transparent TESTA12 gene of *Arabidopsis* encodes a multidrug secondary transporter-like protein required for flavonoid sequestration in vacuoles of the seed coat endothelium," *Plant Cell*, 13:853-872, 2001.
Devic et al., "The *Banyuls* gene encodes a DFR-like protein and is a marker of early seed coat development." *The Plant Journal*, 19:387-398, 1999.
McKhann and Hirsch, "Isolation of chalcone synthase and chalcone isomerase cDNAs from alfalfa (*Medicago sativa* L.): highest transcript levels occur in young roots and root tips," *Plant Mol Biol.*, 24(5):767-77, 1994.
Nesi et al., "The TT8 gene encodes a basic helix-loop-helix domain protein required for expression of DFR and Ban genes in *Arabidopsis siliques*," *Plant Cell*, 12:1863-1878, 2000.
Nesi et al., "The *Arabidopsis* TT2 genr encodes an R2R3 MYB domain protein that acts as a key determinant for *Proanthocyanidin* accumulation in developing seed," *The Plant Cell*, 13:2099-2114, 2002.

(Continued)

*Primary Examiner*—Anne Kubelik
(74) *Attorney, Agent, or Firm*—Steven P. Rhines, Esq.; Sonnenschein Nath & Rosenthal LLP

(57) ABSTRACT

The invention provides method and compositions for the modulation of condensed tannin production in plants. The methods of the invention allow creation of plants having novel phenotypes. Increased expression of condensed tannins in plants may be used to increase the nutritional value of food plants for both human and animal consumption. Increased condensed tannin content also reduces the potential for bloat in animals fed certain forage plants low in condensed tannin content. The invention may also be used to modify plant pigmentation.

50 Claims, 41 Drawing Sheets

OTHER PUBLICATIONS

Sagasser et al., "*A. thaliana* Transparent Testa 1 is involved in seed coat development and defines the WIP subfamily of plant zinc finger proteins,." *Genes Dev.*, 16:138-149, 2002.

Skadhauge et al., "Leucocyanidin reductase activity and accumulation of *Proanthocyanidins* in developing legume tissues," *Am. J Bot.*, 84:494-502, 1997.

Tanner et al., "*Proanthocyanidins* (condensed tannin) destabilise plant protein foams in a dose dependent manner," *Austr. J. Agric. Res.*, 46:1101- 1109, 1995.

Walker et al., "The transparent testa glabra I locus, which regulates trichome differentiation and anthocyanin biosynthesis in *Araidopsis*, encodes a WD40 repeat protein," *Plant Cell*, 11:1337-1350, 1999.

Xie et al., "Role of *Anthocyanidin* reductase, encoded by Banyuls in plant flavonoid biosynthesis," Science, 299:396-399, 2003.

Baudry et al., "TT2, TT8, and TTG1 synergistically specify the expression of banyuls and *Proanthocyanidin biodynthesis* in *Arabidopsis thaliana*," *The Plant journal*, 39:366-380, 2004.

Xie et al., "*Anthocyanidin redutases* from *Medicago truncatula* and *Arabidopsis thaliana*," *Archives of Biochemistry and Biophysics*, 422:91-102, 2004.

Aerts et al., "Polyphenols and agriculture: beneficial effects of *Proanthocyanidins* in forages," *Agriculture, Ecosystems and Environment*, 75:1-12, 1999.

Carron et al., "Genetic modification of condensed tannin biosynthesis in Lotus comiculatus. 1. Heterologous antisense dihydroflavonol reductase down-regulates tannin accumulation in 'hairy root' cultures," *Theoretical and Applied Genetics*, 87:1006-1015, 1994.

Cheynier et al., "Size Separation of Condensed Tannins by Normal-Phase High-Performance Liquid Chromatography," *Methods Enzymology*, 299:178-184, 1999.

Colliver et al., "Differential modification of flavonoid and isoflavonoid biosynthesis with an antisense chalcone synthase construct in transgenic Lotus comiculatus," *Plant Molecular Biology*, 35:509-522, 1997.

Damiani et al., "The maize transcription factor Sn alters proanthocyanidin synthesis in transgenic Lotus corniculatus plants," *Australian Journal of Plant Physiology*, 26.159-169, 1999.

de Majnik et al., "Anthocyanin regulatory gene expression in transgenic white clover can result in an altered pattern of pigmentation," *Australian Journal of Plant Physiology*, 27:659-667, 2000.

Debeaujon et al., "Proanthocyanidin-accumulating cells in *Arabidopsis* testa: regulation of differentiation and role in seed development," *The Plant Cell*, 15:2514-2531, 2003.

Douglas et al., "Effect of condensed tannins in birdsfoot trefoil (lotus corniculatus) and sulla (Hedysarum coronarium) on body weight, carcass fat depth, and wool growth of lambs in New Zealand," *New Zealand Journal of Agricultural Research*. 42:55-64, 1999.

Foo and Porter, "The Phytochemistry of *Proanthocyanidin* Polymers," *Phytochemistry*, 19:1747-1754, 1980.

Gu et al., "Concentrations of proanthocyanidins in common foods and estimations of normal consumption," *J. Nutr.*, 134:613-617, 2004.

Gu et al., "Fractionation of Polymeric Proeyanidins from Lowbus Blueberry and Quantification of Procyanidins in Selected Foods with an Optimized Normal-Phase HPLC-MS Fluorescent Detection Method," *J. Agricultural and Food Chem.*, 50:4852-4860, 2002.

Horsley et al., "Effects of Gene ant13 on Agronomic and Malt Quality Traits of Barley," *Crop Science*, 593-598, 1991.

Jende-Strid, "Gene-enzyme relations in the pathway of flavonoid biosynthesis in barley," *Theoretical and Applied Genetics*, 81:668-674, 1991.

Liu et al., "Bottlenecks for metabolic engineering of isoflavone glycoconjugates in *Arabidopsis*," *Proc. Natl, Acad. Sci* USA, 99, 14578-14583, 2002.

Marles et al., "New perspectives on proanthocyanidin biochemistry and molecular regulation," *Phytochemistry*, 64:367-383, 2003.

Marshall et al., "The annual and perennial Medicago species," *Australian Journal of Experimental Agriculture and Animal Husbandry*, 21:47-50, 1980.

Nesi et al., "The Transparent TESTA 16 locus encodes the *Arabidopis bsister mads* domain protein and is required for proper development and pigmentation of the seed coat," *The Plant Cell*, 14:2463-2479, 2002.

Ray et al., "Expression of anthocyanins and proanthocyanidins after transformation of alfalfa with maize Lc," *Plant Physiol*, 132:1448-1463, 2003.

Reed, "Nutritional toxicology of tannins and related polyphenols in forage legumes," *Journal of Animal Science*, 73:1516-1528, 1995.

Robbins et al., "Genetic Manipulation of Condensed Tannins in Higher Plants," *Plant Physiology*, 116:1133-1144, 1998.

Saito et al., "Direct evidence for anthocyaindin synthase as a 2-oxoglutarate-dependent oxygenase: molecular cloning and functional expression of cDNA from a red forma of Perilla frutescenc," *Plant J.*, 17:181-189, 1999.

von Wettstein et al., "Proanthocyanidin-Free Barley for Brewing: Progress in Breeding for High Yield and Research Tool in Polyphenol Chemistry," *Tech Q Mast Assoc Am*, 22:41-52, 1985.

Zhang et al., "A network of redundant bHLH proteins functions in all TTG1-dependent pathways of *Aradibopsis*," *Development*, 130:4859-4869, 2003.

\* cited by examiner

UV absorbance at 280 nm

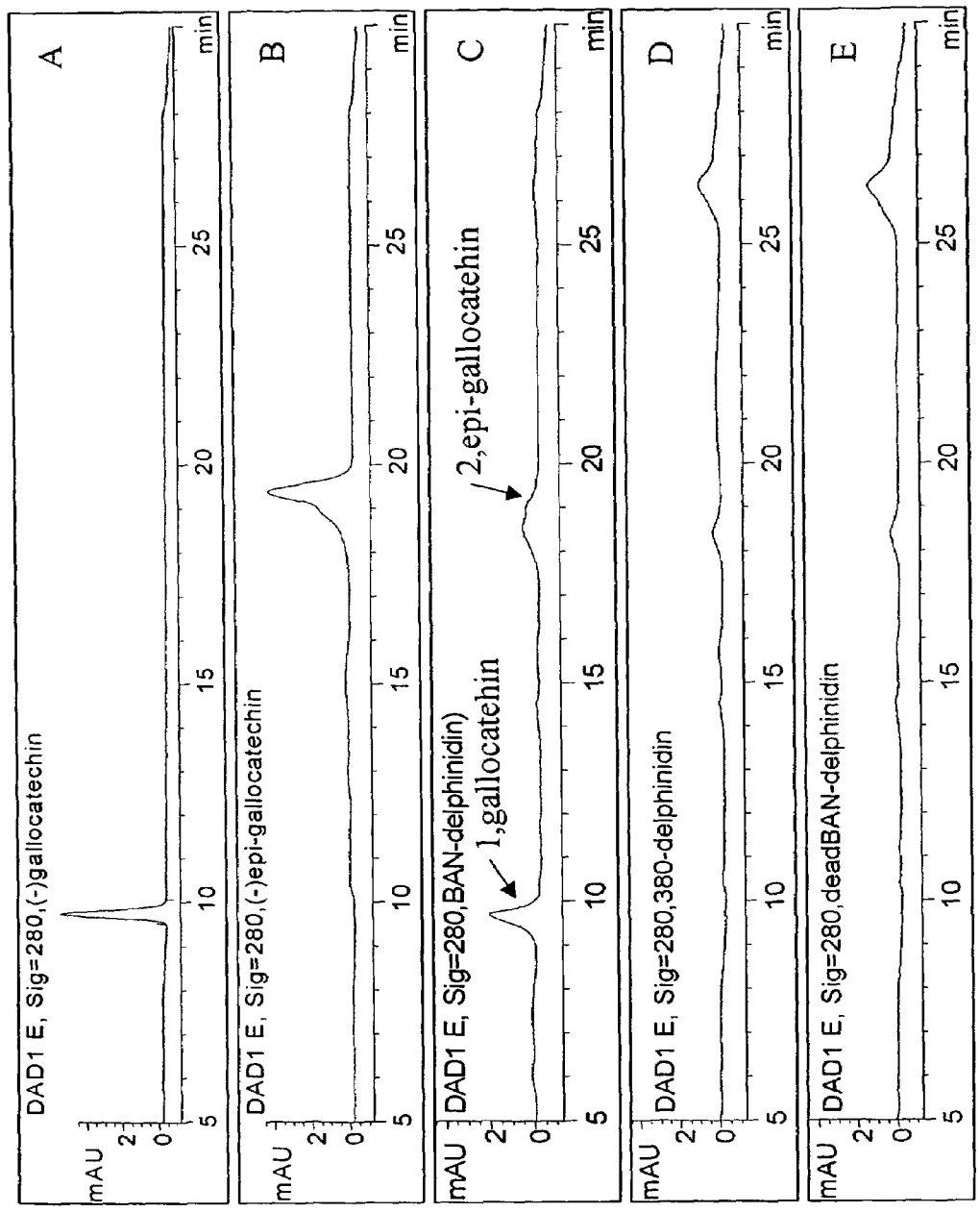
FIG. 14A-E

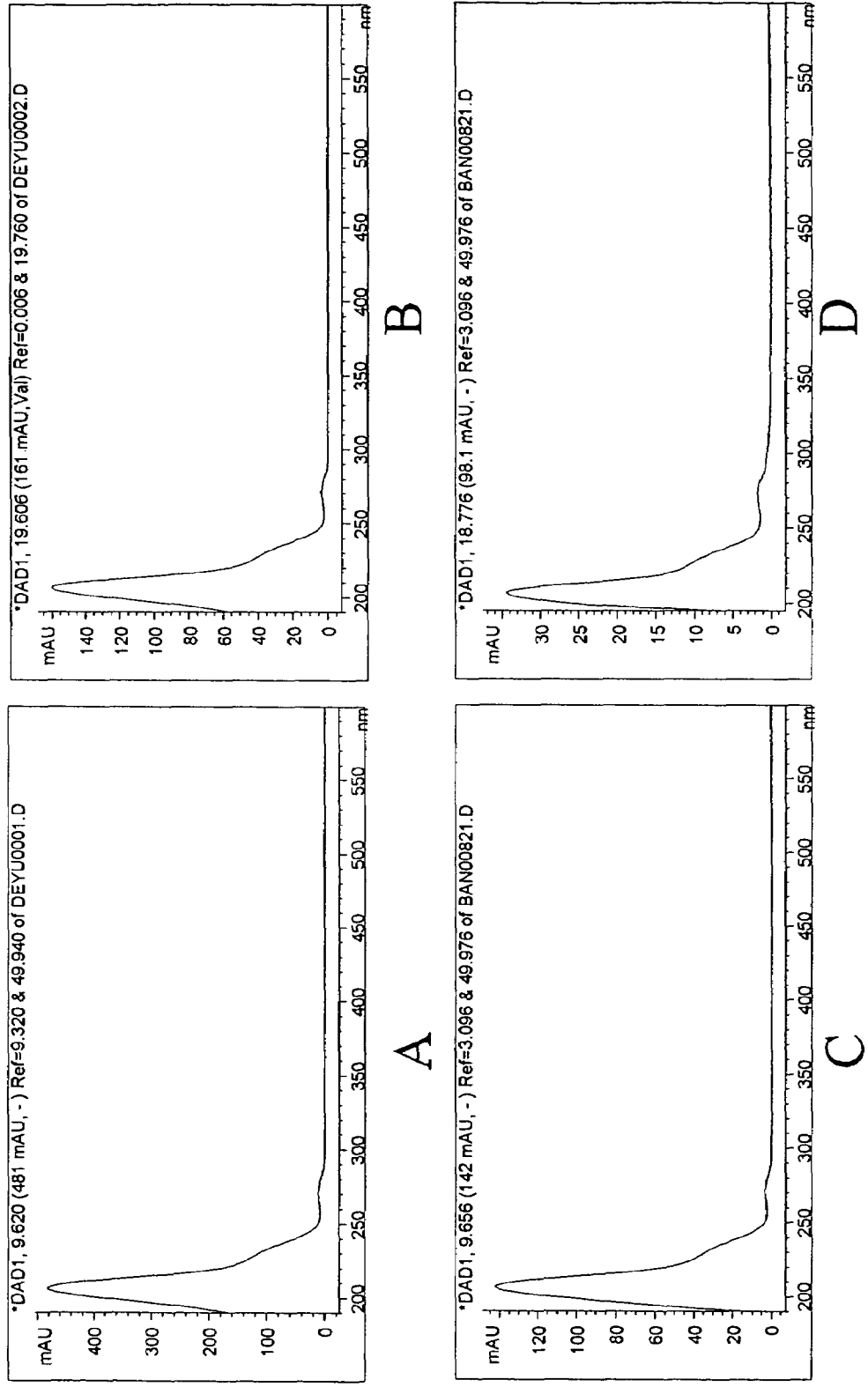
FIG. 15A-D

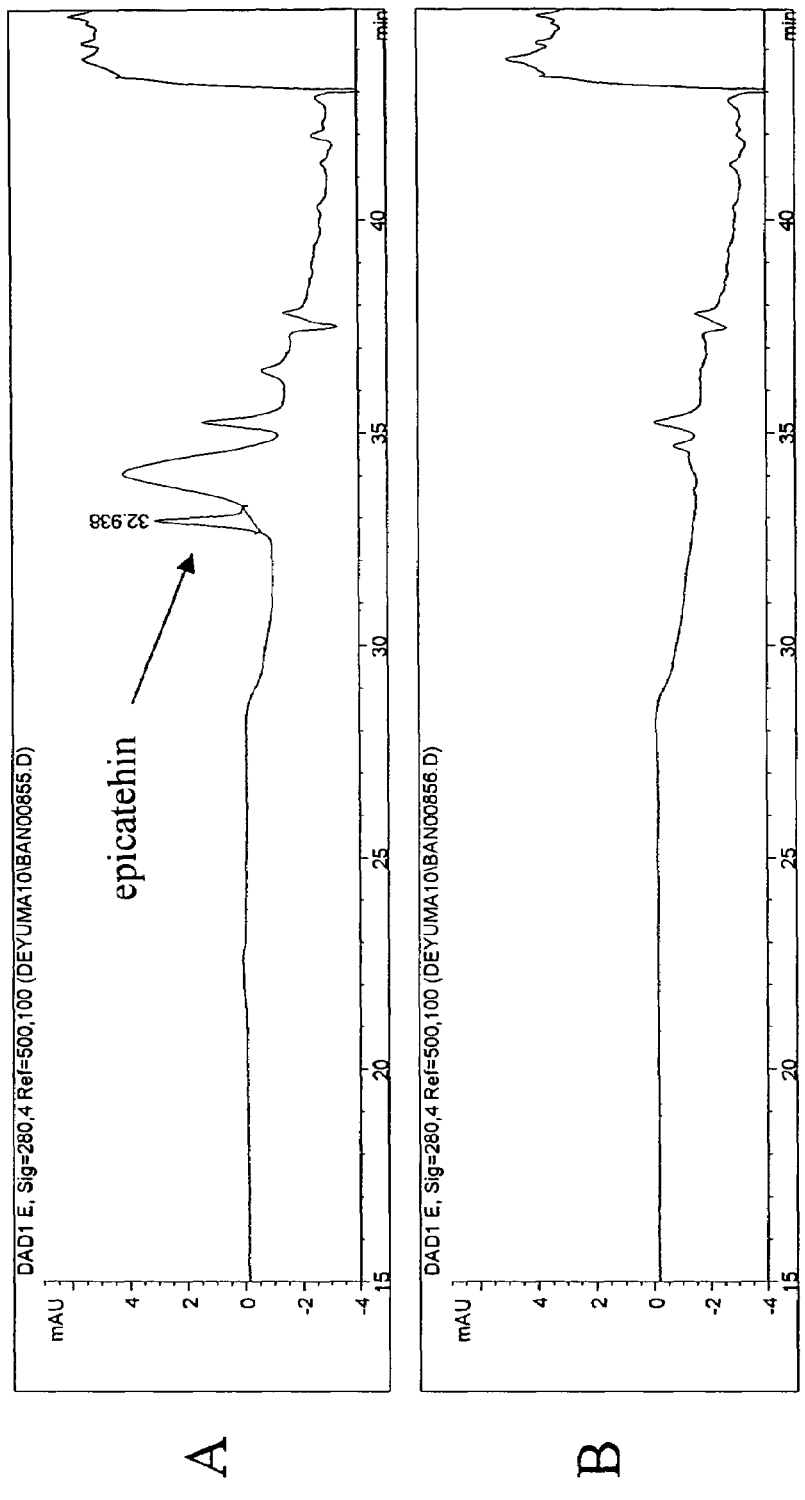
FIG. 16A-B

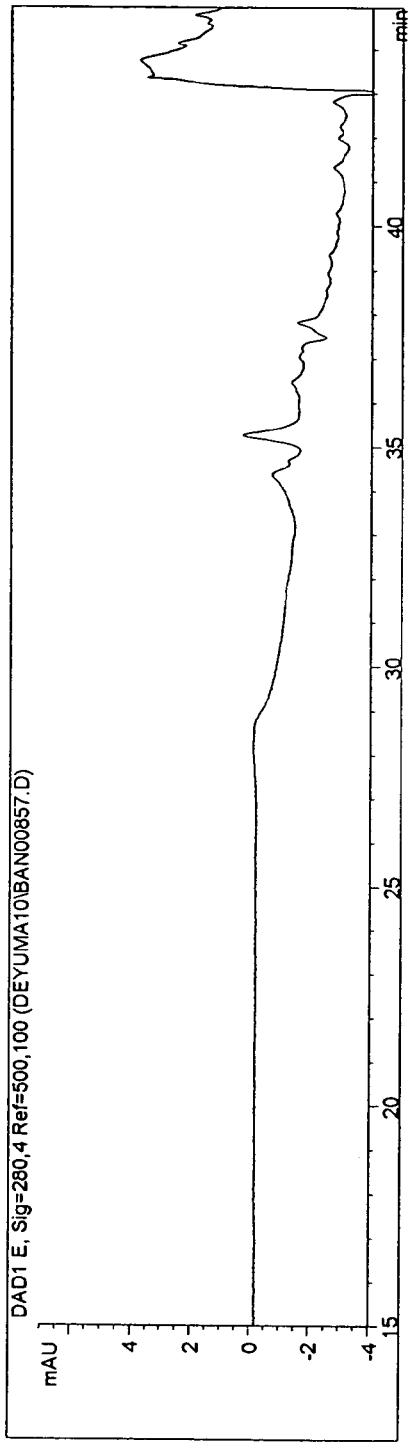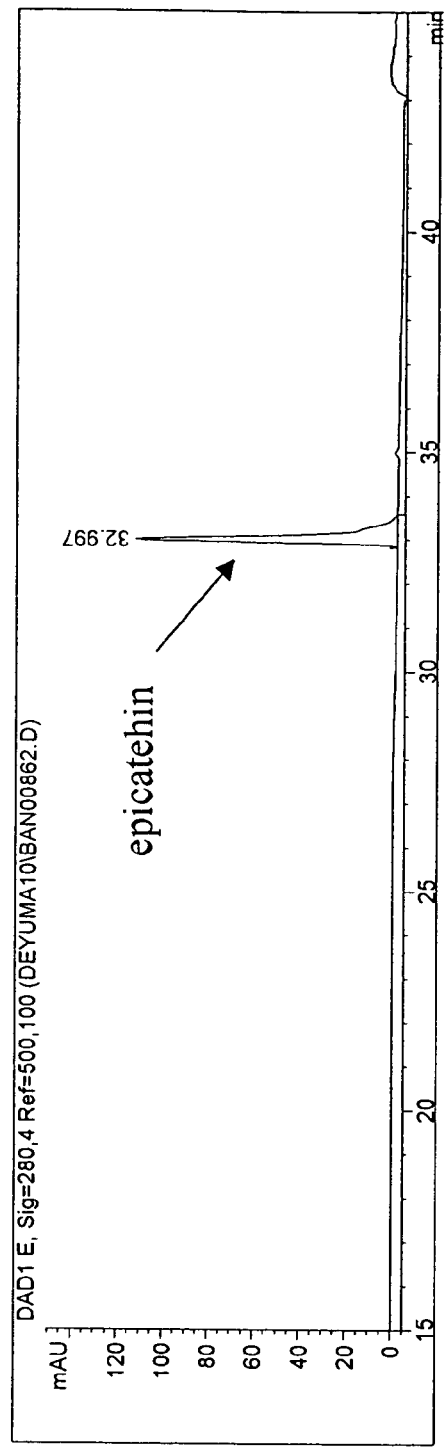
FIG. 16C-D

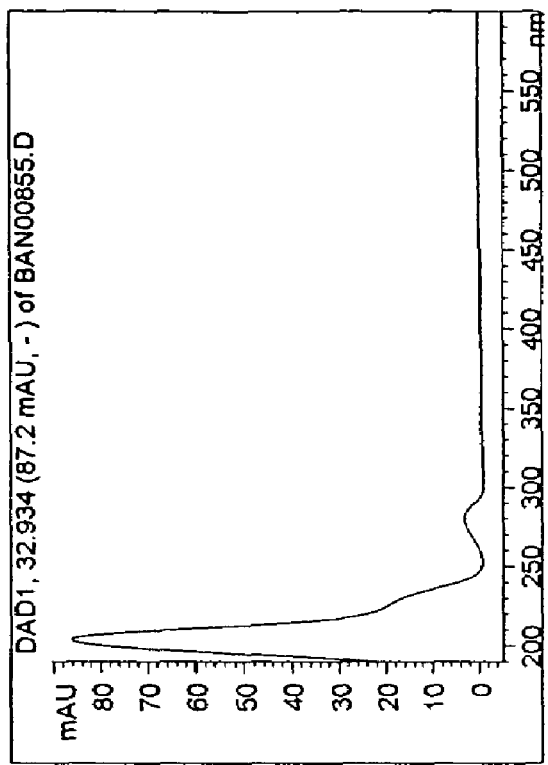
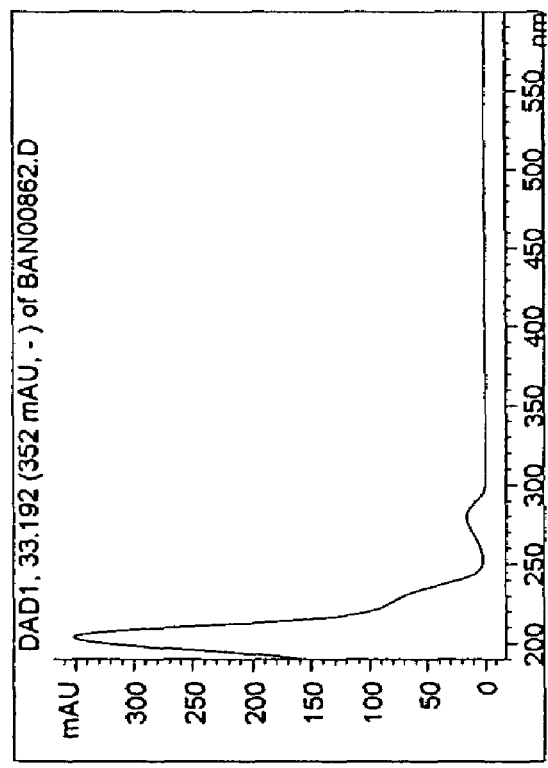
FIG. 17A-B

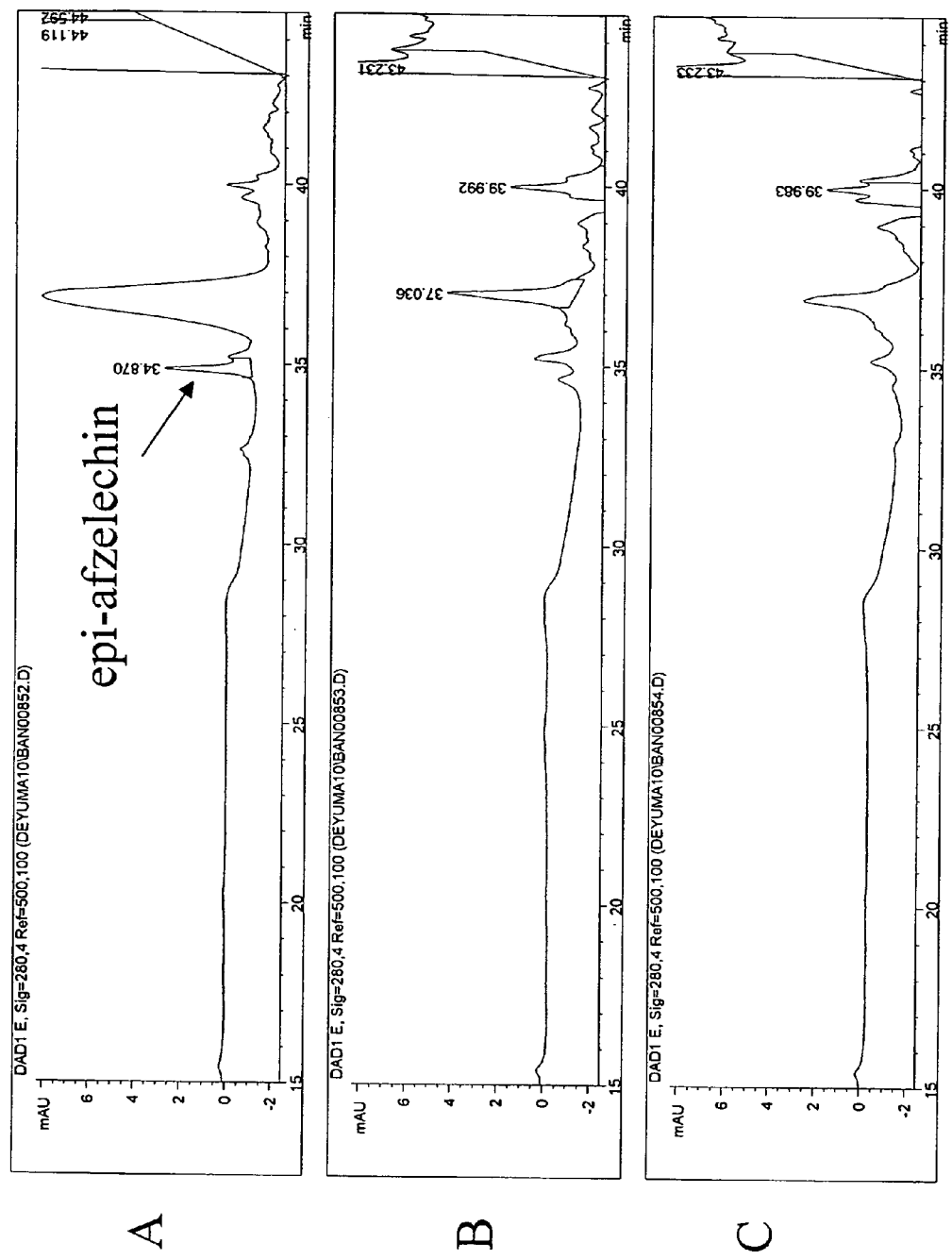
FIG. 18A-C

FIG. 20A-C

PAL: phenylalanine ammonia-lyase
C4H: cinnamate-4-hydroxylase
4CL: 4-coumaroyl:CoA-ligase
CHS: chalcone synthase
F3H: flavanone 3-hydroxylase
F3'H: flavonoid 3' hydroxylase
F3'5'H: flavonoid 3'5'hydroxylase
DFR: dihydroflavonol 4-reductase
LAR: leucoanthocyanidin reductase
ANS: anthocyanidin synthase
ANR: Anthocyanidin reductase (BAN)
CON: condensing enzyme(s)

```
                                                                    Brassica napus
                                                                    Cotton4107
                                                                    Grape4226
                                                                    Medicago90858
                                                                    Sorgham34457
                                                                    Sorgham34925

Majority 780
1011   A A G C G C T C T G A C G C T T C C C C A A T G A T T A T G G T G T T T G A C T C T A G A T C T   Brassica napus
1017   A                                                                                                 Cotton4107
1017                                                                                                     Grape4226
1035   A T A T A T A G A T G C C C C G A T T T A G C T T A A G C A G T A T G T C A G T C G G              Medicago90858
1038   A T T T A A A C T A G T A A G C C A T G C A A G C C A T G C T C A A G T T T G                     Sorgham34457
                                                                                                         Sorgham34925 x x x x x x x x x x x x x x x x x x
                    |------+------|
                          1110

1023                                                              At BAN1
1029                                                              At BAN 2
1034                                                              Barley306
1053                                                              Barley316
1034                                                              Barley49014
 780                                                              Barley55701
1058                                                              Brassica napus
1017                                                              Cotton4107
1017                                                              Grape4226
1085   A C G T A T G A G T C T A G A G G                          Medicago90858
1086   A A T G T C T                                              Sorgham34457
                                                                  Sorgham34925
```

GENETIC MANIPULATION OF CONDENSED TANNINS

This application claims the priority of U.S. provisional patent application Ser. No. 60/392,562, filed Jun. 28, 2002, the entire disclosure of which is specifically incorporated herein by reference.

BACKGROUND OF THE INVENTION

1. Field of the Invention

The present invention generally relates to plant genetics. More specifically, the invention relates to genes involved in the biosynthesis of condensed tannins, and methods for use thereof.

2. Description of the Related Art

Condensed tannins (CTs) are present in many plants and are oligomers or polymers of flavonoid (flavan-3-ol) units. CTs are also commonly termed proanthocyanidins due to the red anthocyanidins that are produced upon heating in acidic alcohol solutions. The most common anthocyanidins produced are cyanidin (from procyanidin) and delphinidin (from prodelphinidin). CTs may contain from 2 to 50 or more flavonoid units. CT polymers have complex structures because of variations in the flavonoid units and the sites for interflavan bonds. Depending on their chemical structure and degree of polymerization, CTs may or may not be soluble in aqueous organic solvents.

CTs are attracting increasing attention due to their ability to affect the nutritional quality of human and animal food (Bagchi et al., 2000; Barry and McNabb, 1999; Morris and Robbins, 1997). In addition, CTs from various plants have beneficial effects on cardiac health and immune responses (Pataki et al., 2002; Foo et al., 2000; Lin et al., 2002). They can reversibly bind to proteins and reduce their degradation rate. The presence of moderate amounts of CT in forage crops reduces the initial rate of microbial digestion of the protein component of forage material in the rumen. The protein tannin complexes then pass to the abomasum where they dissociate at the lower pH, providing "by-pass protein" for utilization by the animal and consequent enhancement of milk and wool production and live weight gain (Barry and McNabb, 1999; Tanner et al., 1995).

In *Arabidopsis thaliana*, CTs accumulate predominantly in the endothelium layer of the seed coat. Many mutations that affect the seed coat color and CT accumulation have been characterized and the corresponding genes cloned. These genes include BAN (Genbank Accession No. AF092912; Devic et al., 1999), TTG1 TTG2, TT1, TT2, TT8 and TT12. The ban mutation leads to accumulation of anthocyanins in the seed coat instead of CTs. TTG1, TTG2, TT1, TT2 and TT8 are regulatory genes and encode a WD-repeat protein (Walker et al., 1999), a WRKY family protein, a WIP subfamily plant zinc finger protein (Sagasser et al., 2002), an R2R3 MYB domain protein (Nesi et al., 2001) and a basic helix-loop-helix domain protein (Nesi et al., 2000), respectively. Expression of the TT2 gene has been shown to induce the TT8 and BAN genes but does not lead to accumulation of CT (Nesi et al., 2001). All the above genes are predominantly expressed in the seed coat endothelium.

The BAN gene encodes an apparent biosynthetic enzyme with sequence similarity to dihydroflavonol reductase (DFR) (Devic et al., 1999), whereas the TT12 gene encodes a multidrug secondary transporter-like protein that may be required for sequestration of flavonoid in vacuoles, the subcellular site of CT deposition (Debeaujon et al., 2001). It has been suggested that the BAN gene might encode an LAR, based on its sequence similarity to DFR and the loss of CT in the ban mutation (Devic et al., 1999).

The foregoing studies have provided a further understanding of the metabolism of plant secondary metabolism. However, the prior art has failed to provide techniques for the application of this understanding to the creation of plants having valuable new characteristics. What is thus needed are practical techniques for the production of novel plants with improved phenotypes and methods for the use thereof. Such techniques may allow the creation and use of plants with improved nutritional quality, thereby benefiting both human and animal health and representing a substantial benefit in the art.

SUMMARY OF THE INVENTION

In one aspect, the invention provides an isolated nucleic acid sequence encoding a BAN polypeptide. Such a nucleic acid sequence may, in certain embodiments of the invention, be further defined as comprising a nucleic acid sequence selected from the group consisting of: a) a nucleic acid sequence encoding the polypeptide of SEQ ID NO:2, b) a nucleic acid sequence comprising the sequence of SEQ ID NO: 1; and c) a nucleic acid sequence hybridizing to SEQ ID NO: 1 under high stringency conditions and having BAN activity. The sequence may also be operably linked to a heterologous promoter and/or a heterologous terminator. Also provided by the invention is an isolated polypeptide comprising the amino acid sequence of SEQ ID NO:2.

In another aspect, the invention provides a transgenic plant transformed with a selected DNA comprising a coding sequence encoding a BAN polypeptide. In one embodiment, the polypeptide comprises the sequence of SEQ ID NO:2 and/or SEQ ID NO:4. In other embodiments, the selected DNA encodes a BAN polypeptide comprising a sequence selected from the group consisting of SEQ ID NO:2, SEQ ID NO:4, SEQ ID NO:30, SEQ ID NO:32, SEQ ID NO:34, SEQ ID NO:36, SEQ ID NO:38, SEQ ID NO:40, SEQ ID NO:42, SEQ ID NO:44 and SEQ ID NO:46. In certain embodiments of the invention, the coding sequence may be further defined as comprising the nucleic acid sequence of SEQ ID NO:1 or SEQ ID NO:3. The coding sequence may, in further embodiments of the invention, be operably linked to a heterologous promoter and/or a heterologous terminator. The selected DNA may also comprise an enhancer, plasmid DNA, and/or a signal peptide. The transgenic plant may be a monocotyledonous or dicotyledonous plant. Examples of monocotyledonous plants include wheat, maize, rye, rice, oat, barley, turfgrass, sorghum, millet and sugarcane. Examples of dicotyledonous plants include tobacco, tomato, potato, soybean, cotton, canola, alfalfa, sunflower, and cotton. In one embodiment of the invention, the plant is maize. In another embodiment of the invention, the plant is an alfalfa plant.

A transgenic plant prepared in accordance with the invention may further comprise a transgenic coding sequence encoding the chalcone isomerase polypeptide encoded by SEQ ID NO:25, SEQ ID NO:26, SEQ ID NO:27 and/or SEQ ID NO:28. In another embodiment of the invention, the transgenic plant comprises a coding sequence encoding the polypeptide of SEQ ID NO: 16, SEQ ID NO: 18, SEQ ID NO:20, SEQ ID NO:22 and/or SEQ ID NO:24.

A transgenic plant in accordance with the invention may, in one embodiment of the invention, be further defined as a fertile $R_0$ transgenic plant, and may also be a progeny plant of any generation of a fertile $R_0$ transgenic plant, wherein said transgenic plant has inherited said selected DNA from said $R_0$ transgenic plant. The invention also provides a seed of such a transgenic plant, wherein said seed comprises said selected DNA.

In yet another aspect, the invention provides a method of increasing tannin biosynthesis in a plant, comprising introducing into said plant a selected DNA comprising a coding sequence encoding the polypeptide of SEQ ID NO:2 and/or SEQ ID NO:4 operably linked to a promoter functional in said plant. By increased or increasing, it is understood in the art that it is meant that a statistically significant increase has been made, e.g., P>0.10 and preferably P>0.05 from tannin production and/or content increase relative to a corresponding plant not increased for tannin biosynthesis. In certain embodiments of the invention, the coding sequence encodes the polypeptide of SEQ ID NO:2 or SEQ ID NO:4, and may be further defined as comprising the nucleic acid sequence of SEQ ID NO:1 or SEQ ID NO:3. In still other embodiments, the coding sequence encodes a polypeptide selected from the group consisting of SEQ ID NO:2, SEQ ID NO:4, SEQ ID NO:30, SEQ ID NO:32, SEQ ID NO:34, SEQ ID NO:36, SEQ ID NO:38, SEQ ID NO:40, SEQ ID NO:42, SEQ ID NO:44 and SEQ ID NO:46.

The coding sequence may, in certain embodiments of the invention, be operably linked to one or more heterologous regulatory elements, including a heterologous promoter, terminator or enhancer. Introducing the selected DNA may be carried out by any method, including by backcrossing and genetic transformation with said selected DNA. The selected DNA may also comprise a sequence encoding a signal peptide. A promoter used may be any type of promoter, including a constitutive or tissue specific promoter.

In a method of increasing tannin biosynthesis in a plant in accordance with the invention, the plant may be a monocotyledonous or dicotyledonous plant. Examples of such monocotyledonous plants include wheat, maize, rye, rice, oat, barley, turfgrass, sorghum, millet and sugarcane. Examples of dicotyledonous plants include tobacco, tomato, potato, soybean, cotton, canola, alfalfa, sunflower, and cotton. In one embodiment of the invention the plant is maize. In another embodiment of the invention the plant is an alfalfa plant. The method may further comprise preparing a transgenic progeny plant of any generation comprising said selected DNA. The invention further provides a plant prepared in accordance with any of the methods of the invention.

In still yet another aspect, the invention provides a method of making food for human or animal consumption comprising: (a) obtaining a plant prepared in accordance with the invention; (b) growing said plant under plant growth conditions to produce plant tissue from the plant; and (c) preparing food for human or animal consumption from said plant tissue. Preparing food may comprise any method, including harvesting the plant tissue. Examples of food that may be prepared include starch, protein, meal, flour or grain.

In still yet another aspect, the invention provides a method for modifying the pigmentation of a plant comprising introducing into said plant a selected DNA comprising a coding sequence encoding the polypeptide of SEQ ID NO:2 and/or SEQ ID NO:4 operably linked to a promoter functional in said plant, wherein the expression of said coding sequence results in a decrease in anthocyanin pigmentation in the plant relative to a second plant that only differs from said plant in that said selected DNA is absent in the second plant. In certain further embodiments of the invention, the coding sequence encodes a polypeptide selected from the group consisting of SEQ ID NO:2, SEQ ID NO:4, SEQ ID NO:30, SEQ ID NO:32, SEQ ID NO:34, SEQ ID NO:36, SEQ ID NO:38, SEQ ID NO:40, SEQ ID NO:42, SEQ ID NO:44 and SEQ ID NO:46. As used herein, "decrease" means a statistically significant difference in anthocyanin concentration and/or visual detection (e.g., p>0.10 and preferably P>0.05). In certain embodiments of the invention, the coding sequence comprised the nucleic acid sequence of SEQ ID NO:1 or SEQ ID NO:3. The coding sequence may, in one embodiment of the invention, be operably linked to one or more heterologous regulatory elements, including a heterologous promoter, terminator or an enhancer. Introducing the selected DNA may be carried out by any method, including by backcrossing and genetic transformation with said selected DNA. The selected DNA may also comprise a sequence encoding a signal peptide. A promoter used may be any type of promoter, including a constitutive or tissue specific promoter. The method may comprise production of plants wherein any and/or all parts of the plant have modified pigmentation. In certain embodiments of the invention, the flowers, seed coat and/or leaves comprise decreased anthocyanin pigmentation.

In a method of modifying the pigmentation of a plant in accordance with the invention, the plant may be a monocotyledonous or dicotyledonous plant. Examples of such monocotyledonous plants include wheat, maize, rye, rice, oat, barley, turfgrass, sorghum, millet and sugarcane. Examples of dicotyledonous plants include tobacco, tomato, potato, soybean, cotton, canola, alfalfa, sunflower, and cotton. In one embodiment of the invention the plant is maize. In another embodiment of the invention the plant is an alfalfa plant. The method may further comprise preparing a transgenic progeny plant of any generation comprising said selected DNA. The invention further provides a plant prepared in accordance with any of the methods of the invention.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 14: MtBAN catalyzes the conversion of delphinidin into gallocatechin and epi-gallocatechin. Gallocatechin (A) and epigallocatechin (B) standards; reaction products from MtBAN enzyme extract (C); pSE380 vector control enzyme extract (D); boiled MtBAN enzyme (E).

FIG. 15: Comparison of UV spectra of (−) gallocatechin (A) and (−) epi-gallocatechin (B) standards and BAN-enzymatic products (1:C and 2:D). and enzymatic products of MtBAN acting on delphinidin (C, 9.6 min product, putative (−) gallocatechin and D, 18.8 min product, putative (−) epi-gallocatechin)

FIG. 16A-D: AtBAN catalyzes the conversion of cyanidin into epi-catechin. NADPH was used as coenzyme. FIG. 16A, reaction products from AtBAN enzyme extract; FIG. 16B, boiled AtBAN enzyme extract; FIG. 16C, vector control enzyme extract; FIG. 16D, epicatechin standard.

FIG. 17A-B: Comparison of UV spectra of epi-catechin standard (FIG. 17A) and the AtBAN enzyme reaction product, putative epi-catechin (FIG. 17B).

FIG. 18A, 18B, 18C: AtBAN catalyzes the conversion of pelargonidin into epi-afzelechin, NADPH used as coenzyme.

FIG. 18A, reaction products from BAN enzyme extract; FIG. 18B, boiled enzyme extraction; FIG. 18C, vector control enzyme extraction.

Figure 24A:
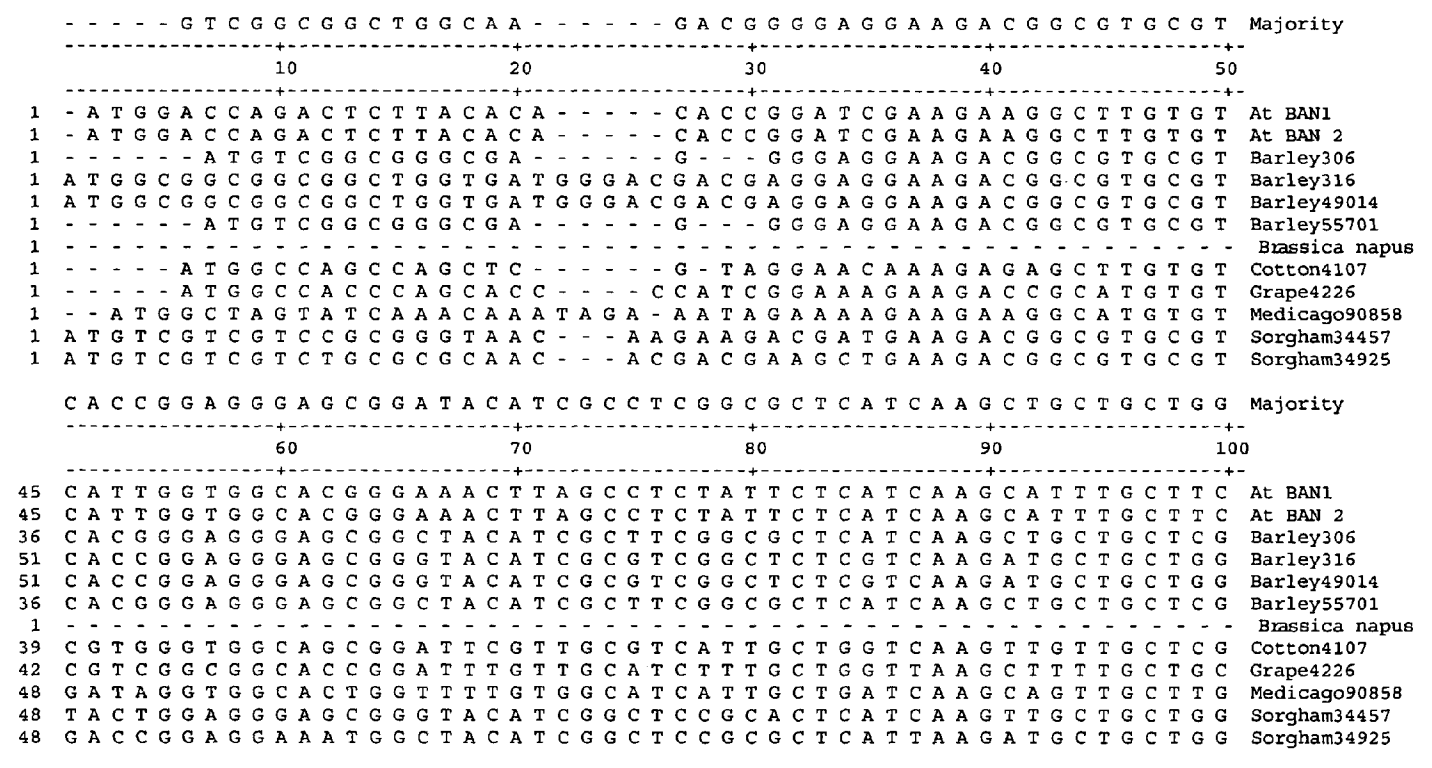
Figure 24B:
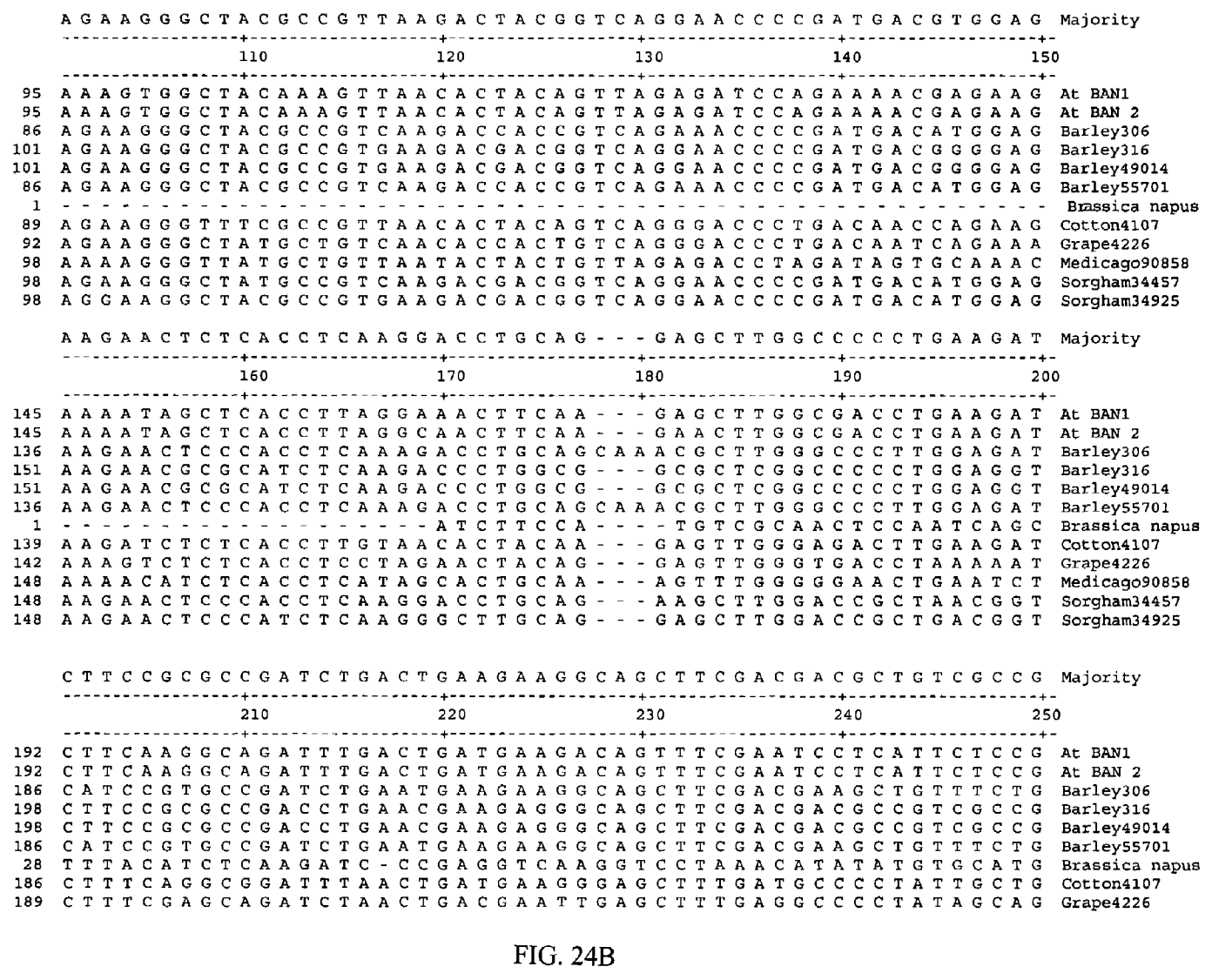
Figure 24C:
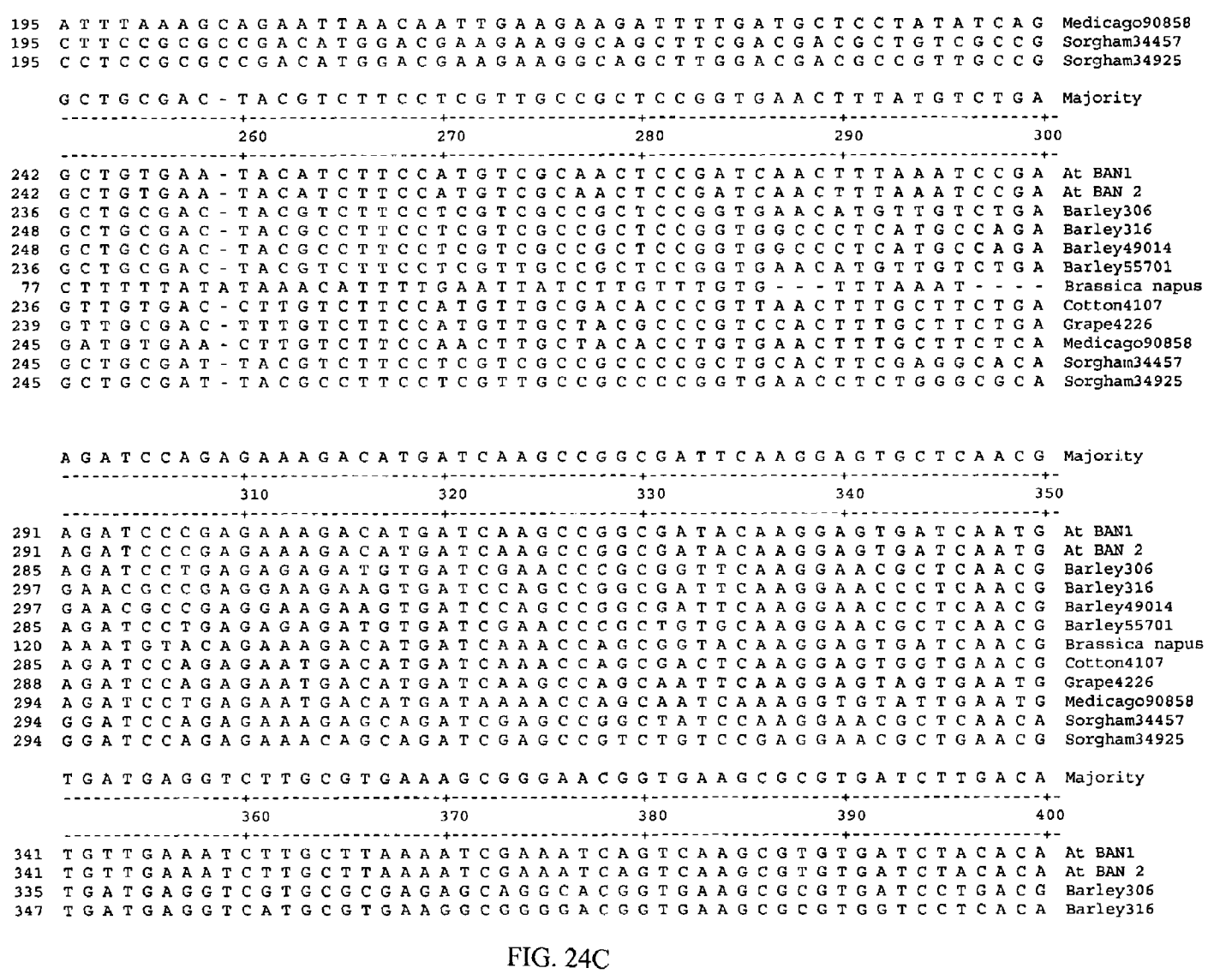
Figure 24D:
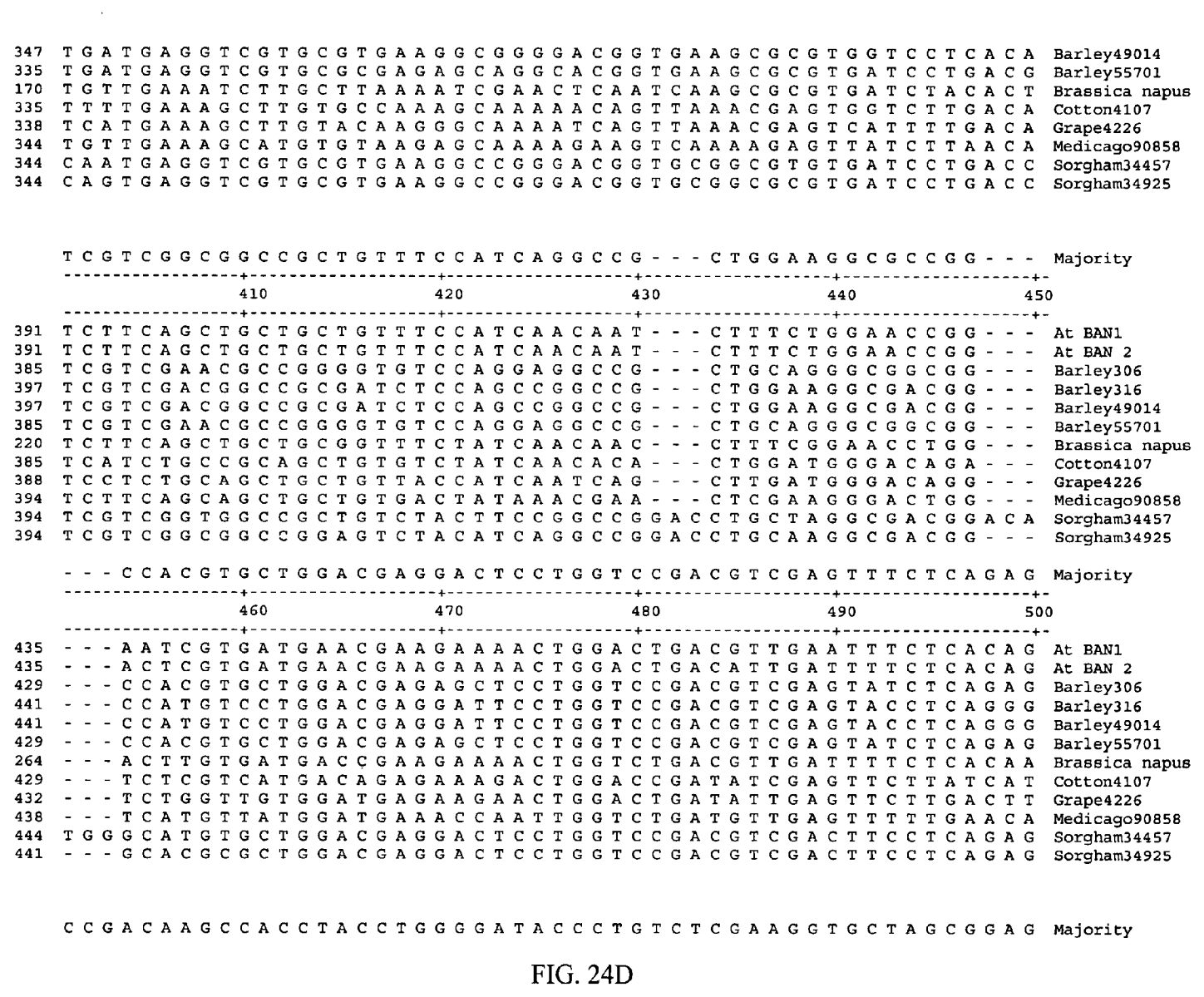
Figure 24E:
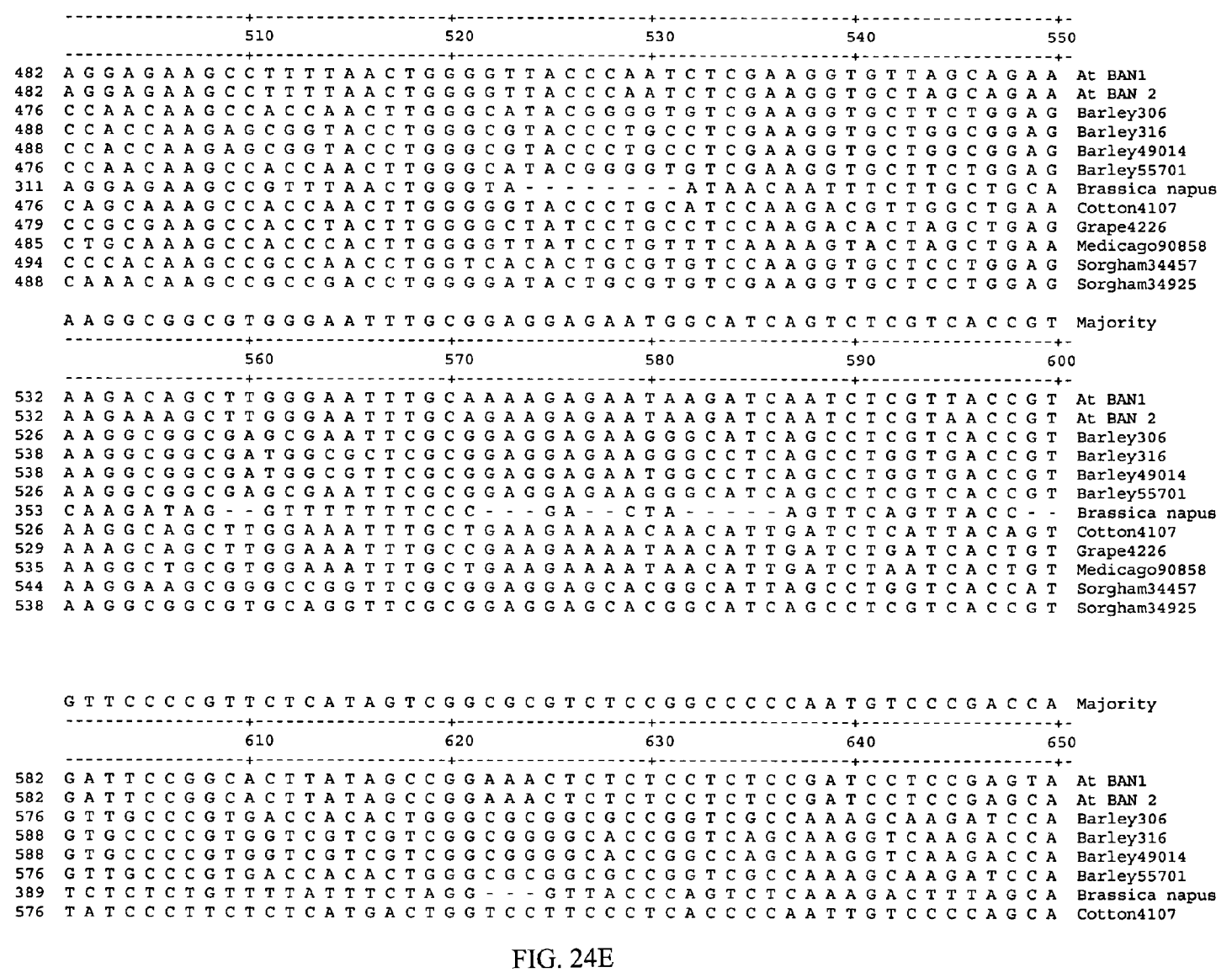
Figure 24F:
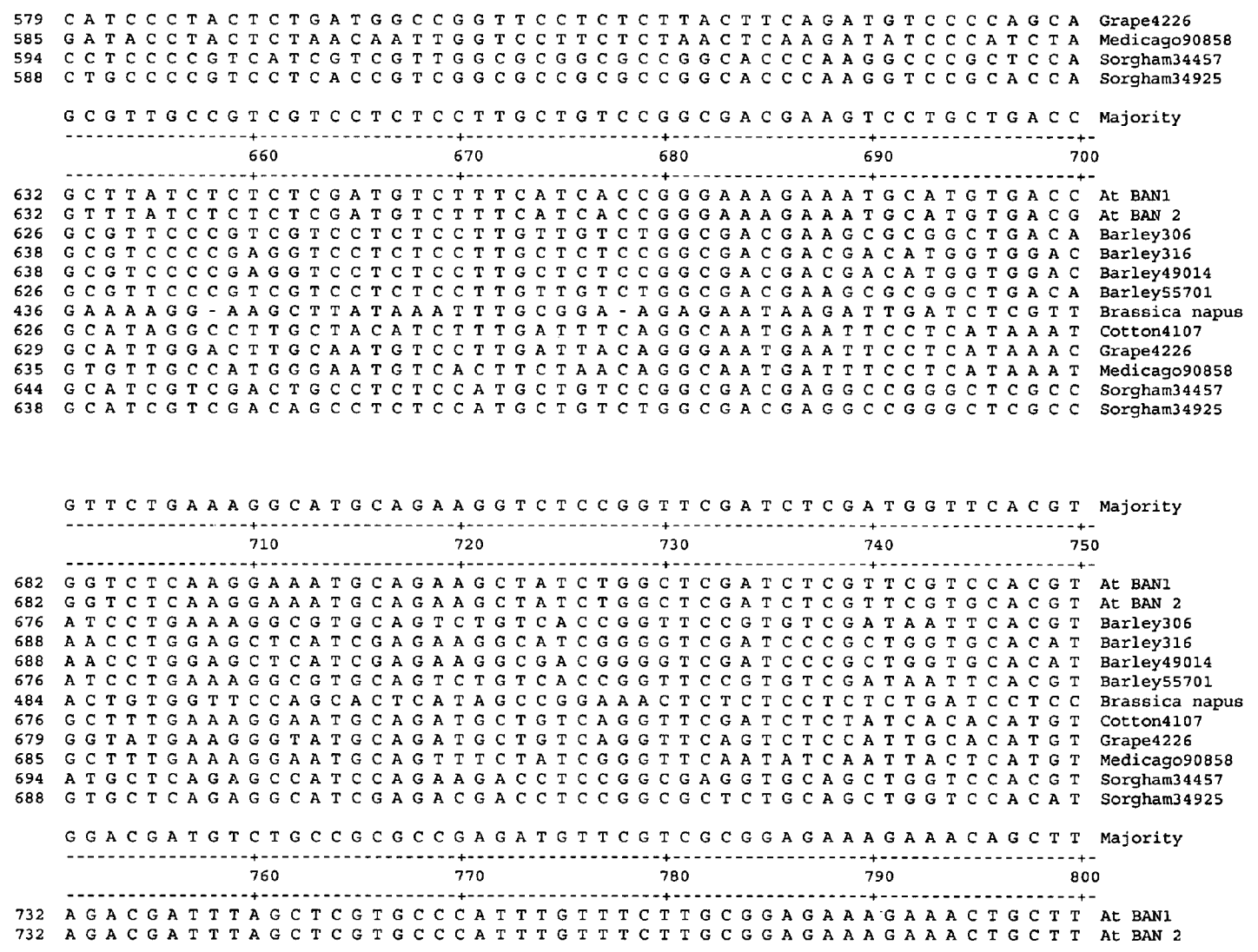
Figure 24G:
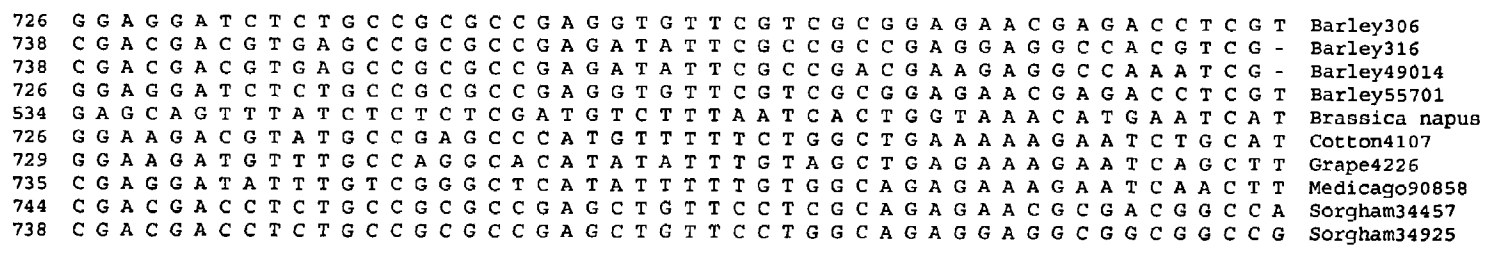
Figure 24H:
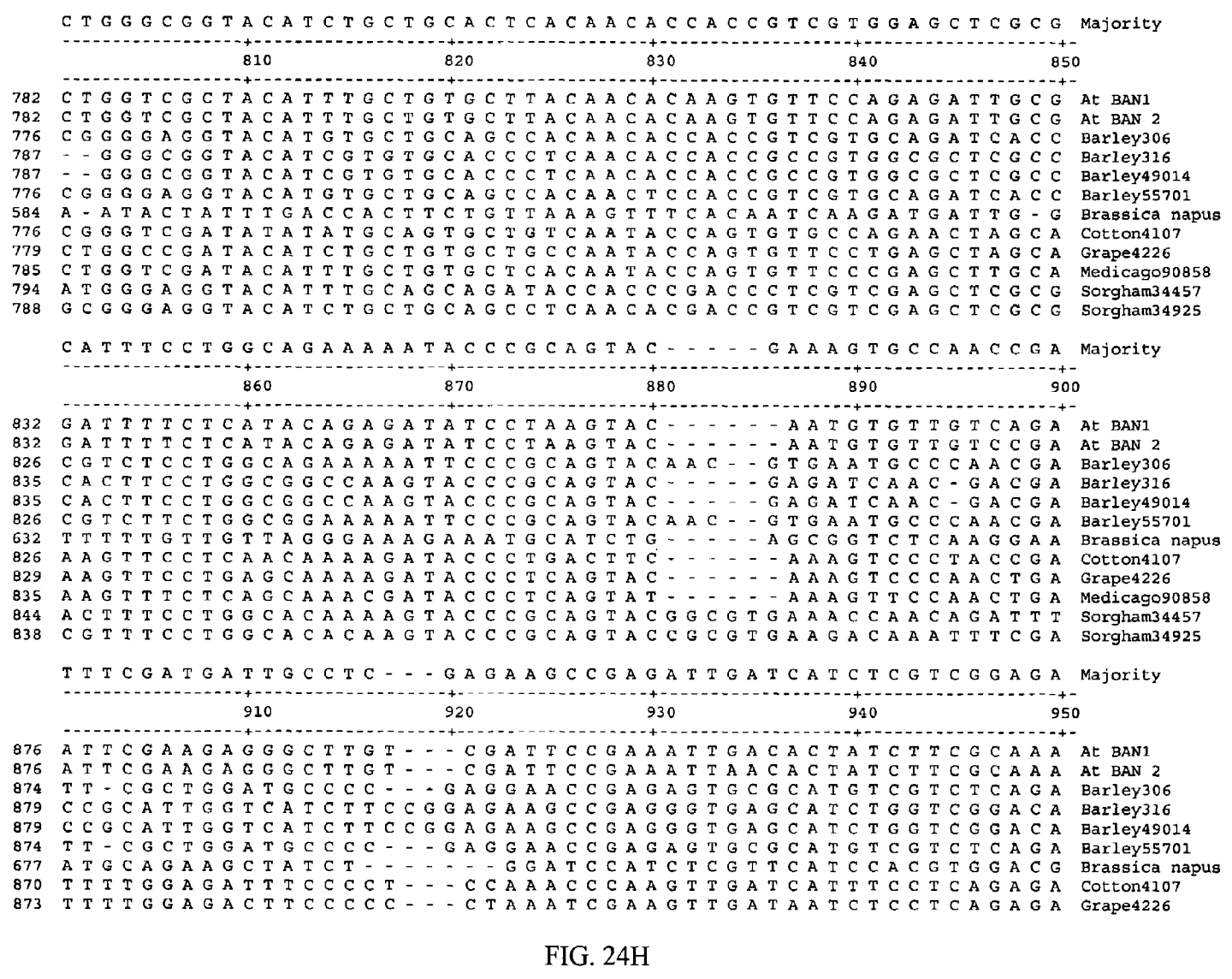
Figure 24I:
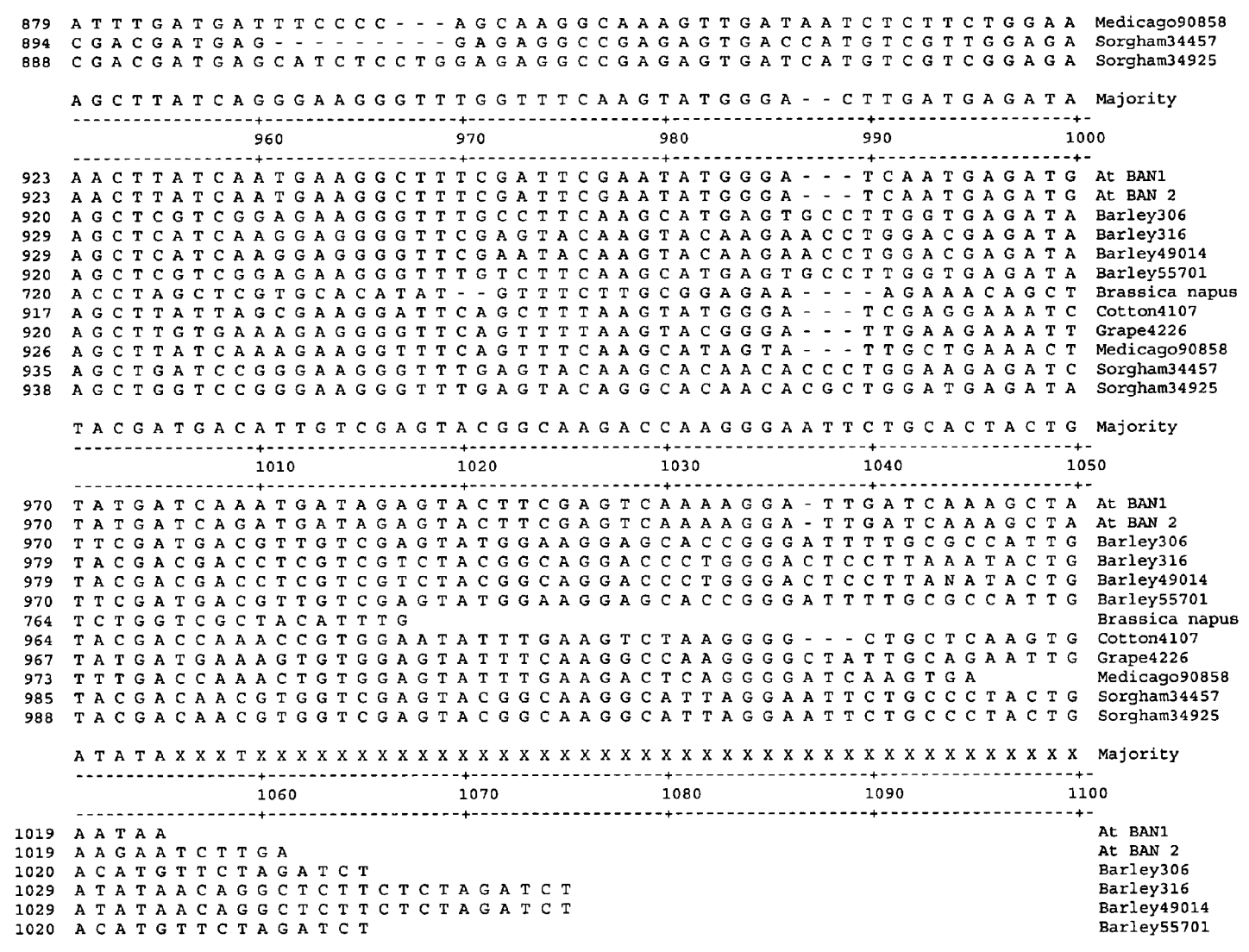

FIG. 24: Alignment of BAN coding sequence open reading frames. Shown are sequences from *Arabidopsis*: At BAN1 (SEQ ID NO:3), At BAN 2 (SEQ ID NO:47); barley: Barley306 (SEQ ID NO:29), Barley316 (SEQ ID NO: 31), Barley49014 (SEQ ID NO:33), Barley55701 (SEQ ID NO:35); *Brassica napus* (SEQ ID NO:37); cotton: Cotton4107 (SEQ ID NO:39); grape: Grape4226 (SEQ ID NO:41); *M. truncatula*: Medicago90858 (SEQ ID NO:1); and sorghum: Sorghum34457 (SEQ ID NO:43), Sorghum34925 (SEQ ID NO:45). Also shown is a "Majority" sequence (SEQ ID NO:53) that provides the most common nucleotide at each position.

Figure 25A:
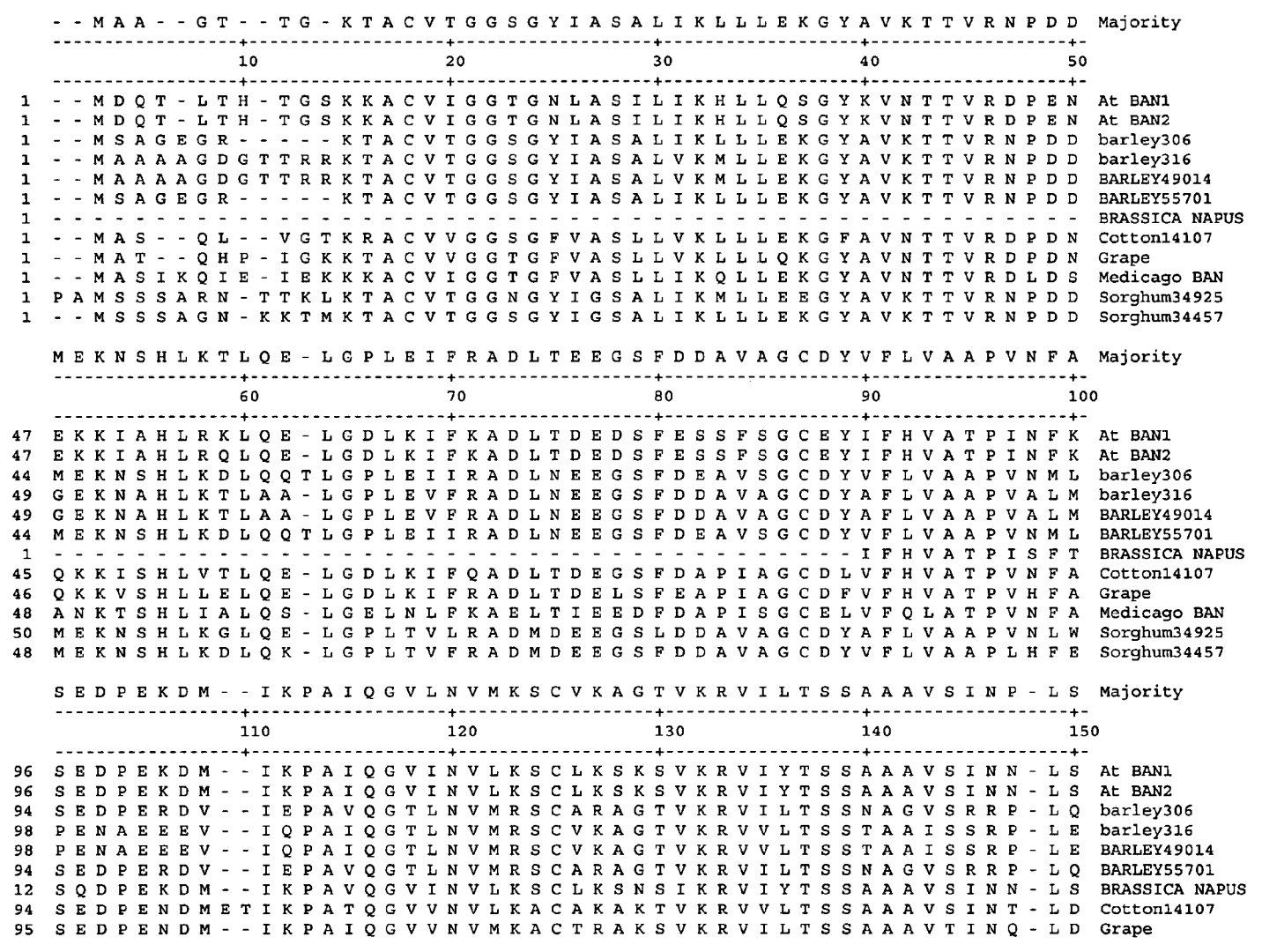
Figure 25B:
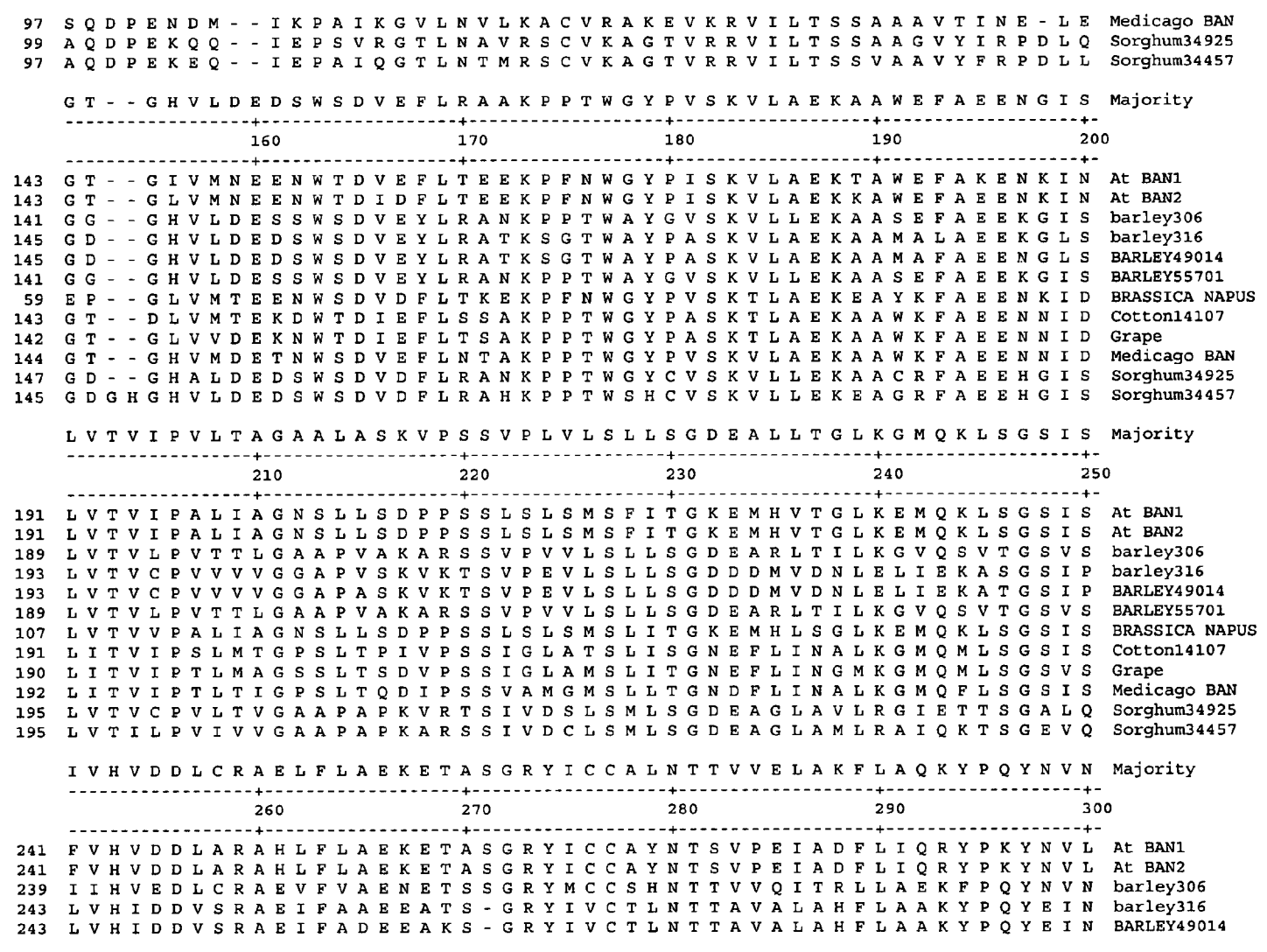
Figure 25C:
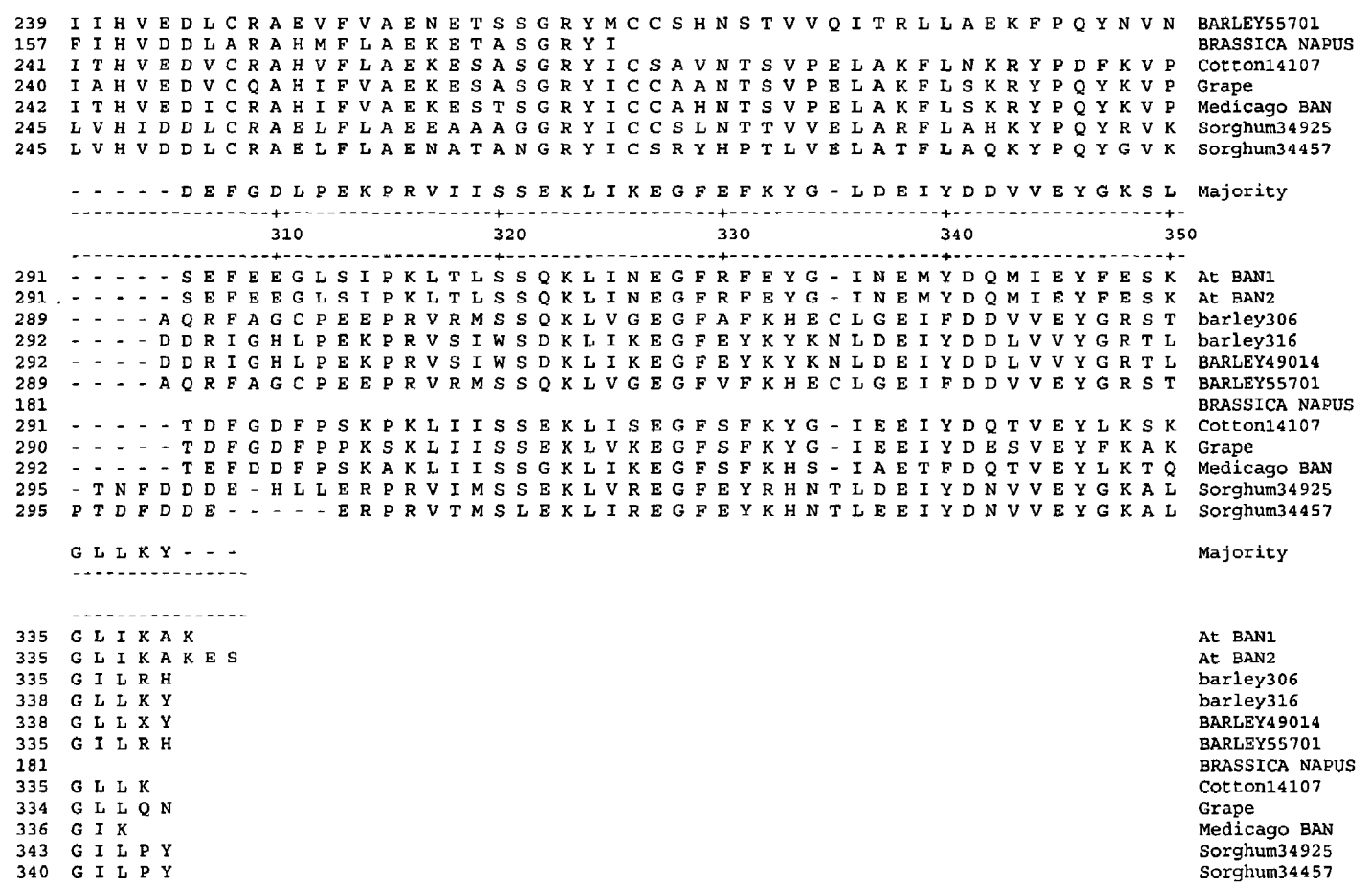

FIG. 25: Alignment of BAN polypeptides. Shown are polypeptides from *Arabidopsis*: At BAN1 (SEQ ID NO:4), At BAN 2 (SEQ ID NO:48); barley: Barley306 (SEQ ID NO:30), Barley316 (SEQ ID NO: 32), Barley49014 (SEQ ID NO:34), Barley55701 (SEQ ID NO:36); *Brassica napus* (SEQ ID NO:38), cotton: Cotton4107 (SEQ ID NO:40); grape: Grape4226 (SEQ ID NO:42); *M. truncatula*: Medicago90858 (SEQ ID NO:2); and sorghum: Sorghum344S7 (SEQ ID NO:44), Sorghum3492S (SEQ ID NO:46). Also shown is a "Majority" sequence (SEQ ID NO:54) that provides the most common amino acid at each position.

FIG. 29A, ANR from flowers; a, the incubation of extract with cyanidin and NADPH producing epicatechin (arrow); b, the incubation of boiled extract with cyandin and NADPH; c, authentic standard epicatehin (arrow). FIG. 29B, ANR from leaves; a, the incubation of extract with cyanidin and NADPH producing epicatechin (arrow); b, the incubation of boiled extract with cyandin and NADPH; c, authentic standard epicatehin (arrow). FIG. 29C, ANR from young pods; a, the incubation of extract with cyanidin and NADPH producing epicatechin (arrow); b, the incubation of boiled extract with cyandin and NADPH; c, the incubation of buffer and extract without NADPH and cyanidin; d, authentic standard epicatehin (arrow). FIG. 29D, barley extract has ANR inhibitor; a, the incubation of extracts from pods with cyanidin and NADPH producing epicatechin (arrow); b, the incubation of extract from pods and barley testa with cyanidin and NADPH producing less epicatechin (arrow).

DETAILED DESCRIPTION OF THE INVENTION

Figure 1:
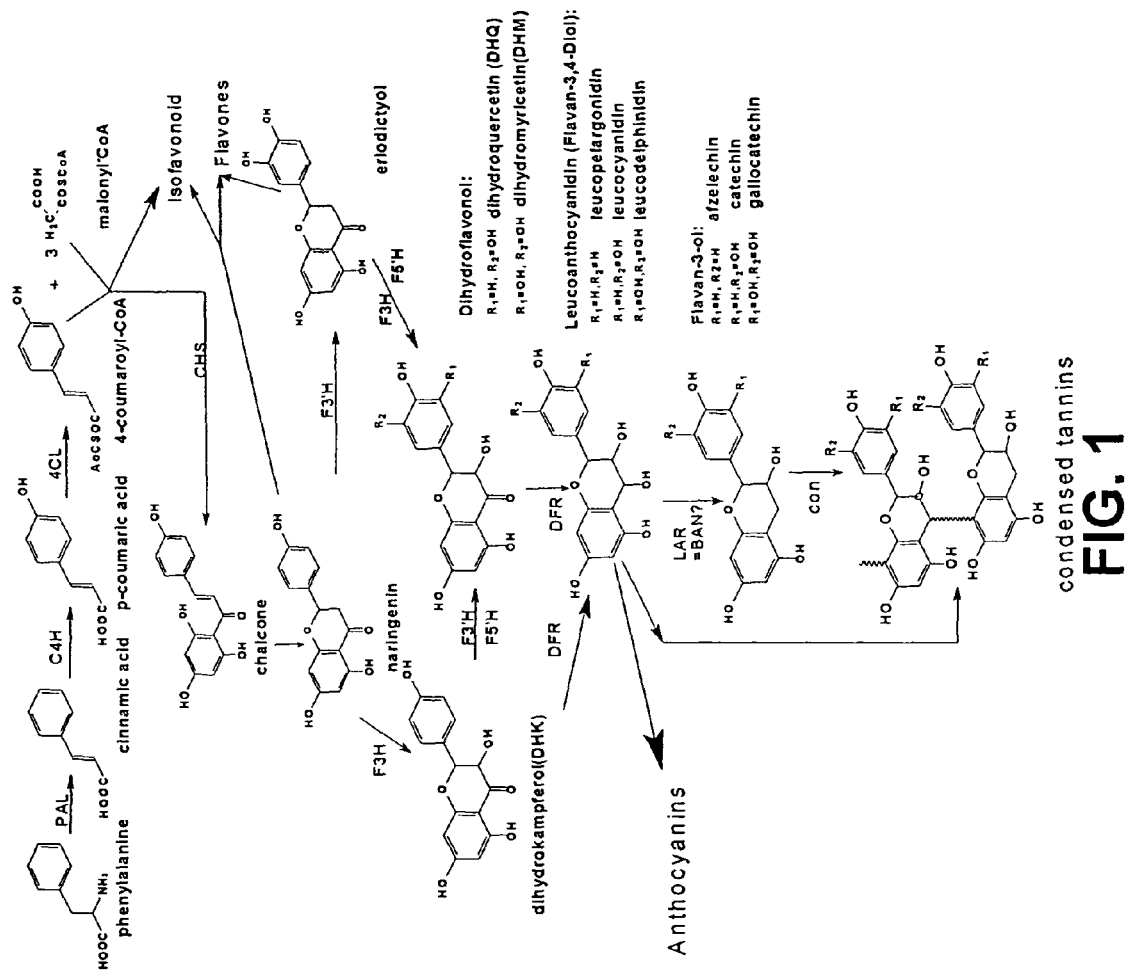
FIG. 1: Shows the published proposed biosynthetic pathways leading to anthocyanins and condensed tannins. PAL: phenylalanine ammonia-lyase; C4H: cinnamate-4-hydroxylase; 4CL: 4-coumaroyl:CoA-ligase; CHS: chalcone synthase; F3H: flavanone 3-hydroxylase; F3'H: flavonoid 3' hydroxylase; F3'5'H: flavonoid 3'5' hydroxylase; DFR: dihydroflavonol 4-reductase; LAR: leucoanthocyanidin reductase CON: condensing enzyme(s).

The invention overcomes the limitations of the prior art by providing methods and compositions for the modification of condensed tannin (CT) metabolism in plants. The invention has numerous important applications to agriculture. One important advance of the invention is that it allows, for the first time, the production of CT in plants or plant tissues that otherwise lack significant CT content. By introduction of a transgene encoding a CT biosynthesis gene into a plant otherwise lacking the gene, or of a gene that is present in the plant but is expressed in minimal quantity in a given plant tissue, the production and accumulation of CT can be induced.

In the absence of CT, high rates of protein degradation occur in the rumen of animals fed certain types of low-CT plants, such as alfalfa, thereby depriving the animal of a major source of amino acids. This can also lead to pasture bloat, a major constraint on the use of protein rich forages such as alfalfa for both livestock and dairy animals. CT can counter this by reversibly binding to proteins to reduce their degradation rate. The presence of moderate amounts of CT in forage crops reduces the initial rate of microbial digestion of the protein component of forage material in the rumen. The protein-tannin complexes then pass to the abomasum where they dissociate at the lower pH, providing "by-pass protein" for utilization by the animal and consequent enhancement of milk and wool production and live weight gain.

The reduced protein degradation that occurs in the presence of CTs helps protect against bloat (Tanner et al., 1995). In addition, it has been shown that the presence of CTs in forage crops significantly reduces emission of the greenhouse gas methane by farm animals. Farm animals have been shown to produce large amounts of methane (~80 kg/yr/cow). Furthermore, CTs also preserve proteins during the ensiling process, increasing the feed value of silage and reducing the amount of nitrogen that is lost to the environment as feedlot waste (Albrecht and Muck, 1991; Reed, 1995).

Many forage crops are low in CT, including annual medics, all *Medicago* spp., white clover, ball clover, Persian clover, red clover, crimson clover, berseem clover, arrowleaf clover, alsike clover, subterranean clovers, fenugreek, and sweetclover (Melilotus spp.). Similarly, bloat can be caused by grazing of wheat pastures and other lush foliage such as fast-growing monocots. "Feedlot bloat" also occurs in cattle fed high-grain rations that may or may not contain legume forage, greenchopped legumes, or other finely ground feed. In these cases, direct engineering of CT accumulation in the forage plant may be used in accordance with the invention to prevent bloat. Further, CT modification could be engineered into feed components that are blended or added to bloat-causing components to reduce the bloat incidence in animals consuming the mixed feed.

One application of the invention is thus the modification of CT biosynthesis in plants with low CT content. Alfalfa is one such plant. Condensed tannins are made in alfalfa (*Medicago sativa*), as in *Arabidopsis*, in the seed coat, but do not accumulate in the leaves (Koupai-Abyazani et al., 1993; Skadhauge et al., 1997). Nonetheless, alfalfa is the world's major forage legume. Therefore, introducing CT biosynthesis to the leaves or other tissues of alfalfa or other low CT plants would substantially improve the utility of this crop for feed by reduction of its potential for causing pasture bloat. Forage crops that accumulate CTs in leaves have low bloating potential; these include *Lotus corniculatus, Leucaena leucocephala, Hedysarum sulfurescens* and *Robinia* spp.

Technology that could result in constitutive expression of CTs in high protein forage crops would also greatly improve the agronomic value of crops in addition to alfalfa. In addition, the potential importance of CTs in human health makes methods for their facile production in plants necessary for the full development of their therapeutic potential.

The present invention provides a gene from *Medicago truncatula* encoding an enzyme that functions to direct precursor from the anthocyanin pathway into the formation of condensed tannins. Also disclosed are methods for the genetic manipulation of condensed tannins for constitutive production of these compounds in plants for a variety of uses.

CTs are synthesized in plants by the flavonoid branch of the phenylpropanoid pathway. However, neither the biosynthetic pathway specific for CTs, nor the genes involved are well characterized. According to the current proposed mode for CT biosynthesis, the first dedicated step in the CT-specific branch pathway has been believed to be the conversion of leucoanthocyanidin, an intermediate also involved in anthocyanin biosynthesis, into catechin by a putative leucoanthocyanidin reductase (LAR) (FIG. 1). Catechins and leucoanthocyanidins are then transported into the vacuole, where they polymerize into CTs. The mechanism of polymerization is completely unknown.

I. APPLICATION OF THE INVENTION

As indicated above, one application of the invention is the introduction or increase of condensed tannin biosynthesis in plants. Such applications may result in forage improvement and nutritional improvement of foods. While much of the flavonoid pathway leading to condensed tannins may be present in a number of tissues, especially those accumulating anthocyanins, the LAR step or another unknown step is critical to formation of condensed tannin monomers (flavan-3-ols) such as catechin and epicatechin, and this step appears to be lacking in tissues which do not accumulate condensed tannins. As such, expression of the LAR step and/or potentially other steps may be used for increasing CT biosynthesis. Tobacco flower data provided herein demonstrate the utility of the approach using the *Medicago truncatula* BAN clone, since it increased condensed tannins and decreased anthocyanin content (as predicted based on pathway competition). *Arabidopsis* BAN was also shown to increase condensed tannins in *Arabidopsis* when over-expressed.

The invention may also be used to improve the nutritional quality of a plant. Catechins and similar flavonoids have been reported to behave as strong antioxidants and have other properties which may make their consumption beneficial to human and animal health. Also, such compounds are generally antimicrobial, and their presence may improve food quality by preventing pre- and post-harvest damage. Accordingly, increases in CT biosynthesis may be used to achieve the associated health benefits.

Another use of the invention comprises the alteration of pigmentation in plant parts, including, but not limited to, flower color, seed coat color and leaf color. This can be achieved, for example, by decreasing anthocyanin content via over-expression of BAN, thereby preventing anthocyanin accumulation and the associated pigmentation of plant tissue. Accumulation of the products of BAN (flavan-3-ols, such as catechin(s), condensed tannins, or similar compounds) may simultaneously improve the nutritional, disease resistance, or herbivore resistance of the plant products.

Manipulation of flower color in particular may be beneficial. Flower color modifications have been valuable to the flower color industry for years. Genetic manipulation of flower color has been reported in the literature using strategies such as increasing or blocking the expression of anthocyanin pathway genes or introducing pathway genes from other species with altered substrate specificity. The data provided herein demonstrate a novel means for altering flower color by over expression of the BAN homolog, a gene from a competing pathway.

Similarly, seed coat color can be modified. White soybean seed coats are desirable in many markets, and are generally obtained using a certain germplasm source which confers low CHS activity on seed coats. Soybean breeders are thus interested in alternative traits to manipulate seed color. The invention provides a means of such manipulation.

In addition to providing the BAN gene alone, other genes may be used to enhance the accumulation of condensed tannins, especially in combination with BAN/LAR expression. For example, the invention further provides two *Medicago truncatula* dihydroflavonol reductase (DFR) clones that were isolated from young developing *Medicago truncatula* seeds, which were shown to accumulate condensed tannins in their seed coats (SEQ ID NO:5; SEQ ID NO:6), or a BAN homolog from *Medicago truncatula* (SEQ ID NO:7). These sequences may find use with the invention as is described herein for the BAN gene.

While clones encoding active DFR enzymes are available from other species, one or both of these specific DFR proteins may interact more efficiently with upstream (e.g., F3H or F3'H) and downstream (e.g., LAR/BAN) enzymes in the condensed tannin pathway in the target species. Despite high similarities at the DNA and protein levels, the two *Medicago truncatula* DFR clones exhibit different kinetic properties in in vitro enzyme assays, and these properties may reflect different roles in metabolism in the cell. They also showed subtle differences in mRNA accumulation in different tissues, suggesting multiple roles or the presence of multiple pathways at work in the same tissue. The genes may thus find use as part of a combination of genes to introduce or increase condensed tannin biosynthesis in numerous species, for forage improvement and nutritional improvement of foods. CT expression could also be modulated using a transgenic chalcone isomerase coding sequence (McKhann and Hirsch, 1994; SEQ ID NO:25; SEQ ID NO:26; SEQ ID NO:27; SEQ ID NO:28).

For example, data was obtained indicating that over-expression of *Medicago* chalcone isomerase increases flavonoid biosynthesis in *Arabidopsis* (x3). This could thus be used in combination with BAN to produce more CT. An *Arabidopsis* or other PAP-1 gene could also be used to increase flux into pathway (Borevitz, 2000; SEQ ID NO: 15). BAN could also be used in conjunction with other regulatory genes such as TTG1 (GenBank Accession No. AJ133743; SEQ ID NO: 19, SEQ ID NO:20), TTG2, TT1 (GenBank Accession No. AF190298; SEQ ID NO:23, SEQ ID NO:24), TT2 (Nesi et al., 2001), and TT8 (GenBank Accession No. AJ277509; SEQ ID NO: 17, SEQ ID NO:18). Benefit may also be obtained from use of BAN in conjunction with TT12 (GenBank Accession No. AJ294464; SEQ ID NO: 21, SEQ ID NO:22) for transport of monomers to the vacuole.

The invention also provides BAN sequences that were originally identified from the plant species barley (SEQ ID NO:29, SEQ ID NO:31, SEQ ID NO:33 and SEQ ID NO:35), sorghum (SEQ ID NO:43 and SEQ ID NO:45), *Brassica napus* (SEQ ID NO:37), cotton (SEQ ID NO:39) and grape (SEQ ID NO:41). The corresponding polypeptides encoded are given in SEQ ID NO:30, SEQ ID NO:32, SEQ ID NO:34, SEQ ID NO:36, SEQ ID NO:38, SEQ ID NO:40 and SEQ ID NO:42. One aspect of the invention thus comprises these nucleic acids and nucleic acids encoding the foregoing polypeptides, as well as the use thereof for plant transformation. Also provided are nucleic acids hybridizing to any of the foregoing nucleic acid sequences and encoding a polypeptide having BAN activity.

As indicated above, a modulation of the phenotype of a gene may be obtained in accordance with the invention by administering a recombinant nucleic acid sequence containing a BAN coding sequence. Such a nucleic acid may be present as a sense and/or antisense nucleic acid. Provided by the invention are BAN sequences which hybridize to the coding sequences provided herein under high stringency conditions. As used herein, "hybridization" or "hybridizes" is understood to mean the forming of a double or triple stranded molecule or a molecule with partial double or triple stranded nature. As used herein "stringent condition(s)" or "high stringency" are those conditions that allow hybridization between or within one or more nucleic acid strand(s) containing complementary sequence(s), but precludes hybridization of random sequences.

Stringent conditions tolerate little mismatch between a nucleic acid and a target strand. Such conditions are well known to those of ordinary skill in the art, and are preferred for applications requiring high selectivity. Medium stringent conditions may comprise relatively low salt and/or relatively high temperature conditions, such as provided by about 5×SSC, 50% formamide and 42° C.; or alternatively, 5×SSC, 50% formamide and 55° C. High stringency may be defined as 0.02M to 0.10M NaCl and 50° C. to 70° C. Specific examples of such conditions include 0.02M NaCl and 50° C.; 0.02M NaCL and 60° C.; and 0.02M NaCL and 70° C.

It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture. It is also understood that compositions and conditions for hybridization are mentioned by way of non-limiting examples only, and that the desired stringency for a particular hybridization reaction in a plant cell is often determined empirically by comparison to one or more positive or negative controls. Depending on the application envisioned it is preferred to employ varying conditions of hybridization to achieve varying degrees of selectivity of a nucleic acid towards a target sequence.

II. PLANT TRANSFORMATION CONSTRUCTS

Certain embodiments of the current invention concern plant transformation constructs. For example, one aspect of the current invention is a plant transformation vector comprising one or more CT biosynthesis gene, including a BAN, PAP-1, TTG1 TTG2, TT1, TT2 and/or TT8 gene. Exemplary coding sequences for use with the invention include those encoding the *Medicago truncatula* BAN polypeptide (SEQ ID NO:2) or the *Arabidopsis thaliana* BAN polypeptide (SEQ ID NO:4). Such coding sequences may comprise the nucleic acid sequence of SEQ ID NO: 1 or SEQ ID NO:3.

In certain embodiments of the invention, coding sequences are provided operably linked to a heterologous promoter, in either sense or antisense orientation. Expression constructs are also provided comprising these sequences, as are plants and plant cells transformed with the sequences.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with sense or antisense CT biosynthesis genes. The CT biosynthesis gene may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with the CT biosynthesis coding sequences will often depend on the purpose of the transformation. One of the major purposes of transformation of crop plants is to add commercially desirable, agronomically important traits to the plant. As CTs are known to confer many beneficial effects on health, one such trait is increased biosynthesis of tannins. Alternatively, plants may be engineered to decrease synthesis of CT and increase anthocyanin content.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to the entire CT biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang & Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be particularly useful, as are inducible promoters such as ABA- and turgor-inducible promoters. In one embodiment of the invention, the native promoter of a CT biosynthesis gene is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include the ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of plant transformation.

It is specifically envisioned that CT biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an a-tubulin gene that also directs expression in roots.

B. Terminators

Transformation constructs prepared in accordance with the invention will typically include a 3' end DNA sequence that acts as a signal to terminate transcription and allow for the poly-adenylation of the mRNA produced by coding sequences operably linked to a CT biosynthesis gene. In one embodiment of the invention, the native terminator of a CT biosynthesis gene is used. Alternatively, a heterologous 3' end may enhance the expression of sense or antisense CT biosynthesis genes. Terminators which are deemed to be particularly useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may fuirther be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

III. ANTISENSE CONSTRUCTS

Antisense treatments represent one way of altering CT biosynthesis in accordance with the invention. In particular, constructs comprising a CT biosynthesis gene and/or a promoter thereof in antisense orientation may be used to decrease or effectively eliminate the expression of CT in a plant. Accordingly, this may be used to increase anthocyanin accumulation in a plant or given plant tissue. In certain embodiments of the invention, a *Medicago truncatula* or *Arabidopsis thaliana* BAN coding sequence could be used in this capacity. In this manner, the accumulation of CT precursors, including anthocyanins, could also be achieved. As such, antisense technology may be used to "knock-out" the function of a CT biosynthesis gene or homologous sequences thereof.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

IV. TISSUE CULTURES

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

V. METHODS FOR GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989). START HERE C. Microprojectile Bombardment Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

VI. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,508,468; and U.S. Pat. No. 5,508,468; each of the disclosures of which is specifically incorporated herein by reference in its entirety).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants are preferably matured either in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}C$-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VII. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a selected CT biosynthesis gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VIII. DEFINITIONS

Condensed tannin (CT) biosynthesis gene: A gene encoding a polypeptide that catalyzes one or more steps in the biosynthesis of condensed tannins.

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule capable of replication in a host cell and/or to which another DNA segment can be operatively linked so as to bring about replication of the attached segment. A plasmid is an exemplary vector.

IX. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Production of CT in Leaves of *Arabidopsis thaliana* by Constitutive Expression of the *Arabidopsis* BAN Gene

*Arabidopsis thaliana* ecotype Colombia (Col-0) and genetically transformed Col-0 plants were grown at 22° C. in long days (16 hr light, 250 µE light intensity). For cloning of the Arabidopsis BAN coding region, 4 µg of total RNA isolated from the first three to four newly emerged siliques was used to synthesize first strand cDNA in a volume of 20 µl containing 20 mM Tris-HCl pH 8.4, 50 mM KCl$_2$, 5 mM MgCl$_2$, 10 mM DDT, 1 mM deoxyribonucleotide triphosphate mixture, 500 ng oligo (dT)12-18 (GibcoBRL), 25 units of RNA Out (Gibco BRL) and 200 units of Moloney murine leukemia virus reverse transcriptase SuperScriptII (Gibco BRL) for 60 min at 42° C. Four µl of the first strand solution was used for PCR reactions using gene specific primers BAN: forward primer GGGCCCATGGACCAGACTCTTACA-CAC (SEQ ID NO:7); reverse primer CCCAGATCTAGAAT-GAGACCAAAGACT (SEQ ID NO:8) and high fidelity Pfu polymerase. PCR products were cloned into pGEM vectors and sequenced to confirm the sequence.

Coding regions for expression in plants were first cloned into the pRTL2 vector. Gene constructs carrying a double cauliflower mosaic virus 35S promoter::gene coding region:: 35S poly (A) transcription termination region were cut from the pRTL2 plasmid and cloned into pCAMBIA2300 and pCAMBIA3300 binary vectors for plant transformation.

Figure 2:
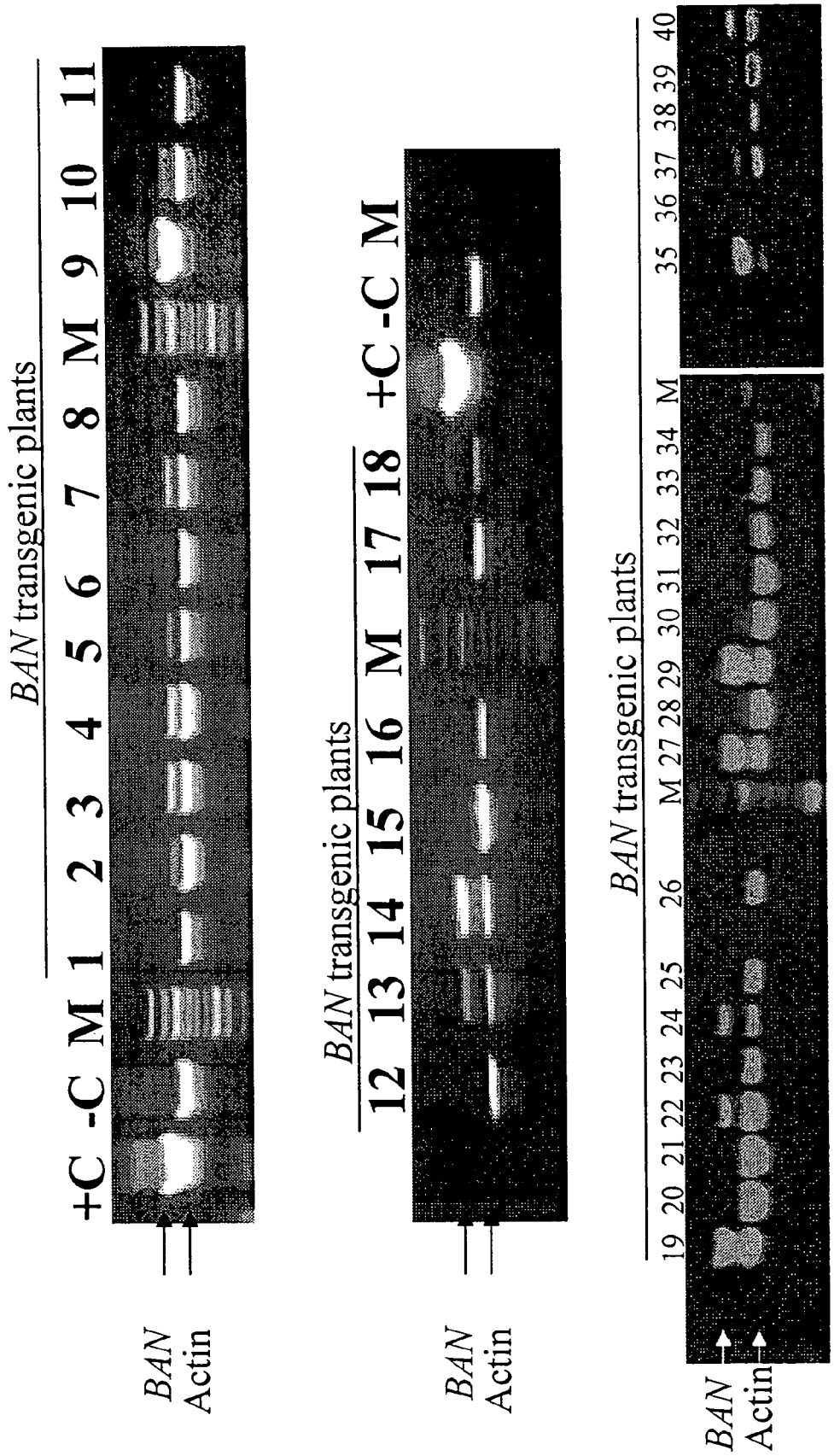
FIG. 2: Shows the analysis of *Arabidopsis thaliana* BAN gene expression in leaves of transgenic Arabidopsis plants by RT-PCR. The numbers refer to independent transformants harboring the 2x35S::BAN gene construct. +C=plasmid carrying the Arabidopsis BAN gene used as positive control; −C=total RNA from a plant transformed with empty vector; M=molecular size markers.

*Arabidopsis* transformants were prepared using the floral dip method (Clough and Bent, 1999). The primary transgenic plants were initially screened by RT-PCR by using Ready-To-Go PCR beads (Pharmacia). The basic recombinant DNA techniques used in the gene cloning were as described by Sambrook et al. (1989). Forty BAN transgenic Col-0 *Arabidopsis* plants were analyzed using RT-PCR. RNA was first isolated from leaf tissues harvested from greenhouse grown plants using RNAzol. The BAN and actin gene-specific primers (actin: forward primer, GATATGGAAAAGATCTG-GCATCAC (SEQ ID NO:9); reverse primer, TCATACTCG-GCCTTGGAGATCCAC (SEQ ID NO:10) were used to monitor the BAN mRNA expression level in comparison to that of the constitutive actin control. The results indicated that 21 plants had very low or undetectable levels, 14 plants had low to medium levels and five (9, 19, 27, 29 and 35) had medium to high levels of BAN mRNA expression in leaf tissue (FIG. 2).

The effect of constitutive BAN gene expression on CT levels was determined by use of the proanthocyanidin (butanol/HCl) assay; a colorimetric method for determination of condensed tannin levels (Dalzell and Kerven, 1998). CTs in leaves or seeds were extracted in 70% aqueous acetone containing 5.26 mM sodium metabisulphite as the antioxidant. The extracts were directly analyzed by the butanol/HCl reaction. Five ml of butanol/HCL mixture (95% butan-1-ol and 5% concentrated HCl) was added to 1 ml of sample in polypropylene tubes. The tubes were heated in a water bath at 95° C. for 1 hr, cooled and read at 550 nm on a spectrophotometer. Unheated blanks were prepared in an identical manner and measured to correct for the background absorbance of the sample.

Three lines, 9, 27 and 29 were analyzed, along with a range of positive and negative controls. The results are summarized in Table 1. The butanol/HCl method can overestimate proanthocyanidin levels, as seen by the background reaction with leaves from Col-0. However, it is clear that the three lines harboring the constitutively expressed BAN gene appear to produce condensed tannins in their leaves, on the basis of increased anthocyanidin levels after heating in butanol/HCl, to levels significantly above the background values of the *Arabidopsis* controls. Other controls included in the study reported in Table 1 were leaf material from alfalfa cv Apollo and *Medicago truncatula* (negative controls) and *Lotus japonicus* (a positive control plant that contains CT in its leaves). Apparent CT levels in the BAN transgenic *Arabidopsis* were, in fact, similar to those in Lotus leaves. The latter were lower than might be expected due to the fact that the Lotus plants were grown under low light. As predicted, seeds of *M. truncatula*, alfalfa and wild-type *Arabidopsis* contained high levels of CT.

TABLE 1

CT levels in Arabidopsis lines and various other plants

| Species (line) | Tissue type | Condensed tannin level (µg cyanidin equivalents/g FW) |
| --- | --- | --- |
| Arabidopsis (N323, ban) | Leaf | 0 |
| Arabidopsis (Col-0) | Leaf | 3.7 |
| Arabidopsis (9) | Leaf | 44.3 |
| Arabidopsis (29) | Leaf | 12.9 |
| Arabidopsis (27) | Leaf | 15.4 |
| Alfalfa cv Apollo | Leaf | 3.0 |
| Medicago truncatula | Leaf | 2.6 |
| Lotus japonicus | Leaf | 16.4 |
| Medicago truncatula | Seed | 139.0 |
| Alfalfa cv Apollo | Seed | 252.3 |
| Arabidopsis (Col-0) | Seed | 265.7 |

Products from butanol/HCl hydrolysis of the above Arabidopsis samples were dried by evaporating the butanol and were dissolved in 100% methanol, followed by HPLC analysis according to Howles et al. (1996). The results are summarized in Table 2. Extracts from seeds and leaves of *Arabidopsis* plants expressing the BAN gene contained a strong peak at a retention time (RT) of approximately 22.9 min, the only major peak between 10 and 30 min RT. This peak was also present at high levels in Col-0 *Arabidopsis* seeds, but was completely absent from leaves of Col-0 or ban *Arabidopsis*. The nature of this compound is yet to be determined. Its levels are expressed as mg catechin equivalents in Table 2.

TABLE 2

Levels of the RT 22.9 minute compound in various Arabidopsis lines

| Arabidopsis line | Tissue type | RT 22.9 min compound (mg catechin equiv/g FW) |
| --- | --- | --- |
| Col-0 | Leaf | 0.0 |
| N323 (ban) | Leaf | 0.0 |

TABLE 2-continued

Levels of the RT 22.9 minute compound in various Arabidopsis lines

| Arabidopsis line | Tissue type | RT 22.9 min compound (mg catechin equiv/g FW) |
|---|---|---|
| 9 | Leaf | 1.73 |
| 27 | Leaf | 1.10 |
| 29 | Leaf | 0.67 |
| Col-0 | Seed | 5.71 |

Example 2

Expression of the BAN Gene Reduces Anthocyanin Levels in the PAP-1D Mutant of *Arabidopsis*

The PAP-1 gene of *Arabidopsis* encodes a MYB transcription factor (Borevitz et al., 2000). Over-expression of PAP-1 leads to strong constitutive induction of the complete pathway leading to anthocyanins in *Arabidopsis*. The pap-1 D mutant of Arabidopsis over-expresses PAP-1 by virtue of the insertion of a T-DNA activation tag close to the 5'-end of the PAP-1 gene, and ectopically accumulates anthocyanins throughout the plant, resulting in a strong purple coloration (Borevitz et al., 2000).

Figure 3:
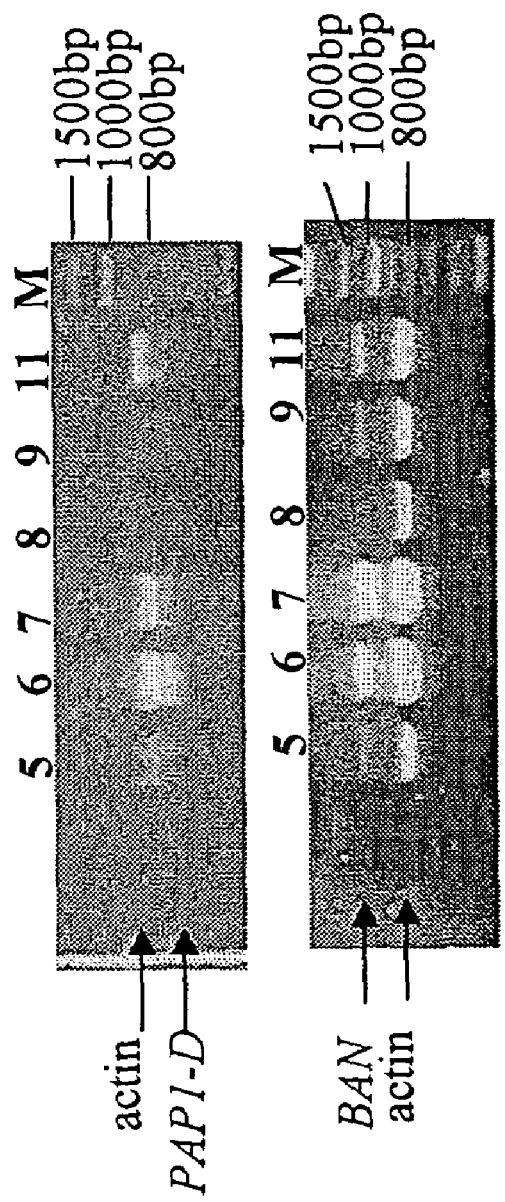
FIG. 3: Shows RT-PCR analysis of transgenic Arabidopsis plants harboring both the T-DNA activation tagged PAP1-D gene and the Arabidopsis BAN transgene, which have lost anthocyanin pigmentation for the expression of PAP1-D, BAN and actin mRNA.

The PAP1-D mutant was transformed with *Agrobacterium* harboring the full length *Arabidopsis* ban cDNA under control of a double 35S promoter (p2xS35::BAN) using the floral dip method (Clough and Bent, 1999). Most of the 2xS35:: BAN transformed PAP1-D plants lost the purple anthocyanin pigmentation in their leaves. Some of these plants were analyzed for expression of PAP, BAN and actin genes by RT-PCR. (PAP1-D primers used for RT-PCR were: forward primer, GGATCCATGGAGGGTTCGTC-CAAAGGGCTGCG (SEQ ID NO:11) and reverse primer, TCTAGACTCGAGATCAAATTTCACAGTCTCTCC (SEQ ID NO:12). The results confirmed that, apart from line #8, these plants strongly expressed both the BAN and PAP1-D genes (FIG. 3). According to the published proposed pathway, these data suggest that the BAN gene product acts on leucoanthocyanidin, a substrate common for both CT and anthocyanin biosynthesis, diverting it into the CT pathway. According to the published proposed pathway, BAN would be a leucoanthocyanidin reductase that had a higher affinity for leucoanthocyanidin or a higher activity in the transformed tissues than leucoanthocyanidin dioxygenase (anthocyanidin synthase), the enzyme that channels leucoanthocyanidin into the anthocyanin pathway (Saito et al., 1999).

Example 3

Cloning of a BAN gene from the forage legume *Medicago truncatula*

Unvernalized seeds of *Medicago truncatula* cv Jemalong line A-17 were planted in pots and seedlings grown in the greenhouse. After pollination of flowers, young seed pods were collected and young seeds about 2-5 mm in size were removed from the pods, dropped in liquid nitrogen, and stored at −80° C. Total RNA was extracted from young seeds using a Qiagen Midi kit RNA isolation kit, and mRNA obtained from the total RNA using a poly(A) mRNA purification kit (Qiagen). A cDNA library was constructed from the mRNA using a Stratagene ZAP-cDNA synthesis kit and ZAP-cDNA Gigapack III Gold cloning kit, according to the manufacturer's protocols. Mass excision of the cDNA library was performed using 1 µl primary cDNA library (about 10, 000 pfu of phage) following the protocol of the Stratagene kit. One µl of mass excised plasmids was used for plating with *E. coli* SoLR cells following the protocols in the Stratagene kit. Five thousand colonies were picked individually and each incubated in 1.5 ml TB medium with 100 µg/ml ampicillin contained in wells of 96-well plates. Plasmids were prepared and inserts sequenced following a robotic plasmid preparation/sequencing protocol utilizing a crude alkaline lysis technique for plasmid isolation (Roe, 1996) followed by automated sequencing with an ABI 3700 capillary sequencer and Big Dye terminator chemistry.

Comparisons of the nucleotide sequences were made against the GenBank database, revealing one clone from the young seed library that appeared to correspond to a full-length *A. thaliana* BAN cDNA (Genbank Accession No. AF092912; Devic, 1999). This clone was located in the third block (96 well plate) sequenced, with the designation NF003H09YS1F1080. The full-length putative *M. truncatula* BAN cDNA was 1.164 kb in length, with 59% nucleotide sequence similarity to *Arabidopsis* BAN (SEQ ID NO:3).

To determine the number of copies of the putative BAN gene in the *M. truncatula* genome, genomic DNA was extracted from *M. truncatula* leaves. Ten µg of DNA was digested with the restriction enzymes HindIII and EcoRI at 37° C. overnight, and fragments resolved by electrophoresis in a 0.8% agarose gel with Tris-acetic acid-EDTA (TAE) buffer. The complete *M. truncatula* putative BAN open reading frame was labeled with $^{32}$P-dCTP using a random primer labeling kit from Promega (Prime-a-Gene® labeling system) and used as probe. DNA gel blot hybridization was performed according to standard protocols (Sambrook et al., 1989; Church and Gilbert, 1984). The results indicated the presence of a single copy of the putative BAN gene in the *M. truncatula* genome.

Example 4

Determination of BAN gene expression patterns in *M. truncatula*

For determining BAN gene expression patterns in *M. truncatula*, total RNA was extracted from different organs including roots, hypocotyls, leaves, flower buds, open flowers and young seeds using a Tri-Reagent kit (Molecular Research Center). Root samples included uninoculated 16 day-old roots and 4 week-old nodulated roots. Young expanding folded leaves and unfolded mature leaves were collected from vernalized greenhouse grown plants without the central red anthocyanin-containing leaf spots, as well as from unvernalized plants grown in a growth room with a light intensity of 200 µE and low nitrogen fertilizer. Flower buds, flowers (including the calyx), and young seeds were collected from plants grown in the greenhouse. Hypocotyls were collected from seedlings either grown in the dark to suppress anthocyanin accumulation or grown under high light to induce anthocyanin accumulation. Seeds were scarified with concentrated sulfuric acid for 10 min and then washed several times with sterile MilliQ water, before placing on wet Whatman 3M paper in clear petri dishes for germination in the dark. White hypocotyls were harvested from five-day old dark grown plants.

Three day-old dark grown seedlings were transferred to light (200 μE) and red/purple hypocotyls were harvested after 30 and 50 hr. Fifteen μg total RNA samples were dissolved in 20 μl RNA preparation solution (0.5λ formaldehyde gel-running buffer, 2.2 M formaldehyde, 50% formamide), denatured at 65° C. for 15 min and chilled on ice. After centrifugation, 2 μl formaldehyde gel-loading buffer (50% glycerol, 1 mM EDTA pH 8.0, 0.25% bromophenol blue, 0.25% xylene cyanol FF) was added to RNA samples, which were then electrophoresed in 1.5% agarose gels in the presence of ethidium bromide (1 μg/20 μl). RNAs were then transfer blotted to GeneScreen Plus®(NEN/Dupont) membranes. Membranes were pre-hybridized at 65° C. in hybridization buffer (1% BSA, 1 mM EDTA pH 8.0, 0.5 M NaHPO$_4$ pH 7.2, 7% SDS) for 4 hours, then labeled probes were added to the hybridization solution and allowed to hybridize with the membrane overnight at 65° C. The BAN gene coding region probe was labeled with α-$^{32}$P dCTP using a Promega Prime-a-Gene® labeling system random primer labeling kit. Hybridized membranes were washed twice for 10 min in wash buffer #1 (0.5% BSA, 1 mM EDTA, 40 mM NaHPO$_4$ pH 7.2, 5% SDS), then twice for 5-10 min in wash buffer #2 (1 mM EDTA, 40 mM NaHPO$_4$ pH 7.2, 1% SDS). Membranes were then exposed overnight in a phosphorimager or exposed to X-ray film at −80° C. for 48-72 hr.

BAN RNA levels were also determined using an RT-PCR method. One μg total RNA sample was used for the first strand cDNA synthesis using an Advantage™ RT-for-PCR kit (Clonetech). Five μl of the first strand cDNA was used for each PCR reaction in 50 μl final volume. The PCR reactions were done using *M. truncatula* BAN gene primers (forward 5'CCTCATAGCACTGCAAAGTTTGGGGG3' (SEQ ID NO:13) and reverse 5'GCCTGTTAG AAGTGACATTCCC3' (SEQ ID NO:14)). The cycle conditions were 94° C. for 2 min; 30 cycles at 94° C. for 30 sec, 60° C. for 30 sec and 72° C. for 1.5 min, followed by a final extension at 72° C. for 10 min. Products of PCR amplification were analyzed by electrophoresis of 20 μl reaction aliquots on 0.8% agarose gels in Tris-acetic acid-EDTA buffer and visualized with ethidium bromide.

Figure 4:
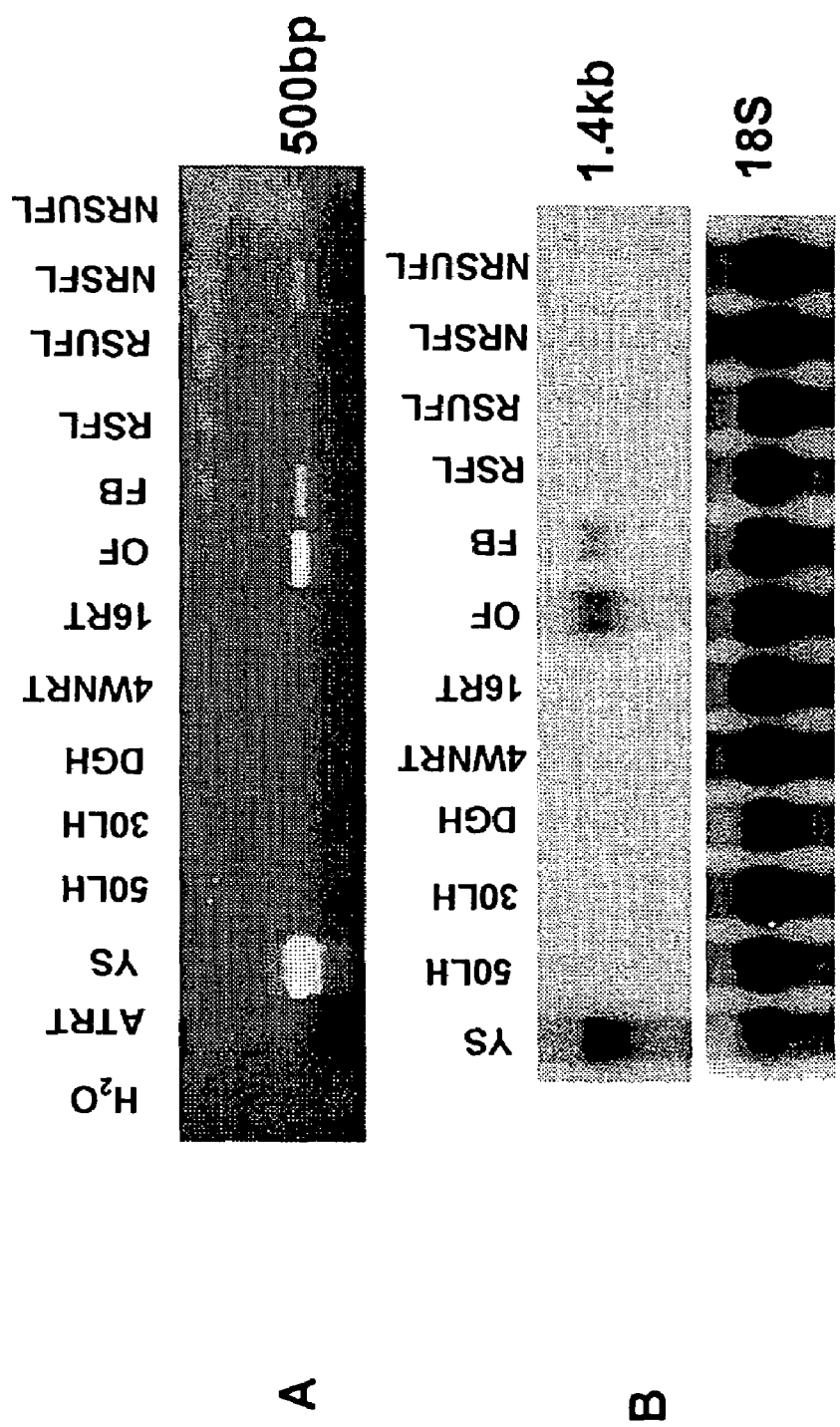
FIG. 4: Shows the tissue specificity of endogenous BAN gene expression in *Medicago truncatula* determined by RT-PCR (A) and Northern blot (B). NRSUFL: nonred-spot-unfolded leaves; NRSFL: non-red-spot-folded leaves; RSUFL: red-spot-unfolded leaves; RSFL: red-spot-folded leaves; FB: flower buds; OF: open flowers; 16RT: 16-day old geminated roots; 4WNRT: 4-week old nodulated roots; DGH: dark-grown hypocotyls; 30LH: 30-hour light-induced hypocotyls; 50LH: 50-hour light-induced hypocotyls; YS: young seeds.

Both RT-PCR and RNA gel blot hybridization analysis showed that the putative BAN gene was most highly expressed in immature seeds, flowers and flower buds of *M. truncatula*, with highest expression in the seeds (FIG. 4). The high level of expression in seeds correlated with the presence of CTs in the *M. truncatula* seed coat, as determined by staining with 1% vanillin in 5 N HCl as described by Kristensen and Aastrup (1986).

Example 5

Inhibition of Anthocyanin Production and Introduction of Formation of CTs in Flower Petals of Tobacco by Constitutive Expression of the *Medicago truncatula* BAN Gene The binary vector pBI121-BAN was constructed by inserting the complete *M. truncatula* BAN open reading frame into the BamHI and SacI sites of pBI121 (Clonetech). In this construct, BAN expression is under control of the cauliflower mosaic virus 35S promoter and Nos 3' terminator. pBI121-BAN was transformed into *Agrobacterium tumefaciens* LBA4404 by electroporation.

Leaves of tobacco (*Nicotiana tabacum* cv. Xanthi) seedlings were cut into discs about 1 cm$^2$ in size, and these were pre-cultured for 3 days on MS104 medium consisting of MS0 [containing 4.3 g/l MS salts (Gibco) (Murashige and Skoog, 1962), 1 ml/l B5 vitamins (Sigma) (Gamborg et al., 1968), 30 g/l sucrose, and 0.3% (w/v) phytogel, pH 5.7], 1.0 mg/l benzyladenine (BA) and 0.1 mg/l naphthalene acetic acid (NAA). A single colony of *A. tumefaciens* harboring pBI121-BAN was grown overnight in the dark in Luria-Bertani medium (Sambrook et al., 1989) containing 100 mg/l streptomycin (Sigma) and 50 mg/l kanamycin (Sigma) at 28° C. on a gyratory shaker set at 250 rpm. Bacteria from this culture were pelleted and then re-suspended in 50 ml sterile MS0 liquid medium. The pre-cultured leaf discs were dipped into the bacterial suspension for 10 min, blotted dry on sterile Whatman paper, and inoculated on solid MS104 medium for co-cultivation for 3 days. The infected leaf discs were then further selected on MS104 medium supplemented with 300 mg/l kanamycin and 500 mg/l carbenicillin. Putative transgenic shoots were rooted on rooting medium consisting of MS0 supplemented with 200 mg/l kanamycin and 500 mg/l carbenicillin. Thirty eight putative transgenic plantlets were transferred to pots and grown in the greenhouse.

Figure 5:
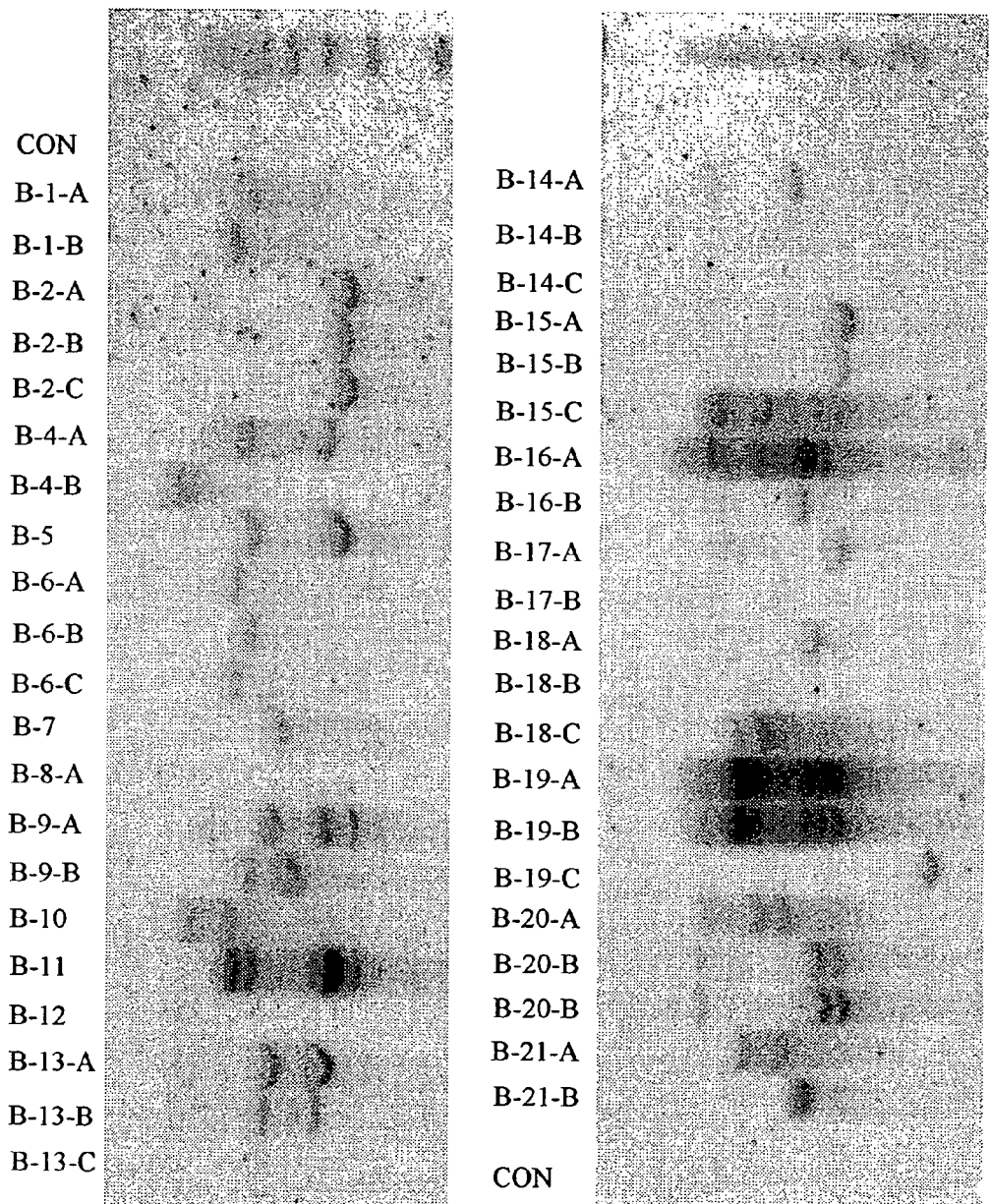
FIG. 5: Shows DNA gel blot analysis of tobacco plants transformed with the *Medicago truncatula* BAN gene. The genomic DNA had been digested with HindIII, and the NPTII gene from the binary vector was used as labeled probe. Each lane represents a separate transgenic plant. CON=wild-type control.

To confirm chromosomal insertion of the *Medicago* BAN transgene, genomic DNA was extracted from leaves of putative transgenic tobacco plants. One hundred to 150 mg of fresh leaf tissue was processed using the DNeasy® Plant Minikit (Qiagen). After digestion with HindIII, eight μg of genomic DNA were separated by electrophoresis as described above. The NPTII selectable marker gene in the binary vector was used as probe; it was labeled with $^{32}$P-dCTP using the Ready-To-Go DNA labeling beads (dCTP) kit (Amersham Pharmacia Biotech). Membranes were pre-hybridized for 4 hours at 65° C. in hybridization buffer (1% BSA, 1 mM EDTA, 0.5 M NaHPO$_4$ pH 7.2, 7% SDS), then labeled probe was added and allowed to hybridize with the membrane overnight at 65° C. Hybridized membranes were washed twice for 10 min in wash buffer #1 (0.5% BSA, 1 mM EDTA, 40 mM NaHPO$_4$ pH 7.2, 5% SDS), then washed twice for 5-10 min in wash buffer #2 (1 mM EDTA, 40 mM NaHPO$_4$ pH 7.2, 1% SDS). Membranes were exposed overnight in a phosphorimager or exposed to X-ray film at −80° C. for 48-72 hr. The DNA gel blot analysis showed that the transgene construct copy number varied from single to multiple copies. More than two copies of the transgene construct were present in transgenic lines B-9-A, B-11, B-15-C, B-16-A, B19-A and B-19-B (FIG. 5). Plants B-5, B-13-A and B-21-A had two copies (FIG. 5). A single copy was present in plants B-1-B, B-2-A, B-2-B, B-2-C, B-6-A, B-6-B, B-6-C, B7, B-15-A, B-15-B, B-16-B, B-17-A, B-18-A, B-19-C and B-21-B (FIG. 5).

Example 6

Confirmation of BAN Transgene Expression and Phenotypic Modification

Figure 6:
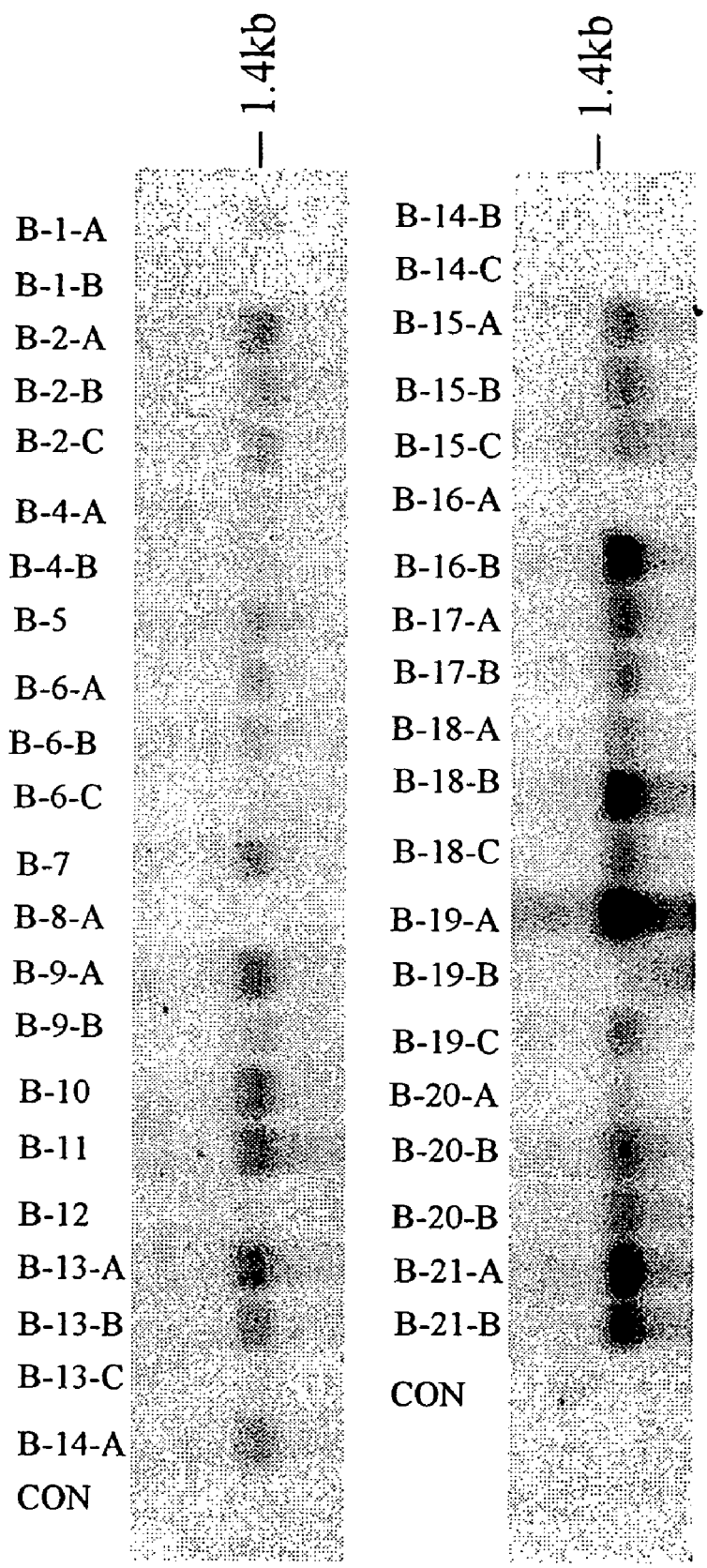
FIG. 6: Shows RNA gel blot analysis of total RNA from leaves of tobacco plants transformed with the *Medicago truncatula* BAN gene. The *M. truncatula* BAN cDNA sequence was used as labeled probe. Each lane represents a separate transgenic plant. CON=wild-type control.

To investigate the extent of *Medicago* BAN transgene expression in tobacco plants, total RNA was extracted from young leaves. A labeled *M. truncatula* BAN probe was made using a Ready-To-Go DNA labeling beads (dCTP) kit (Amersham Pharmacia Biotech). Thirty four plants showed various levels of BAN transcripts as determined by RNA gel blot hybridization analysis (FIG. 6). Lines B-16-B, B-18-B, B-19-

A, B-21-A and B-21-B had the highest levels of BAN transgene expression (FIG. 6). Lines B-2-A, B-7, B-9-A, B-10, B-11, B-13-A, B-13-B, B-14-A, B-15-A, B-15-B, B-17-A, B-17-B, B18-C, B-19-C, B-20-B and B-20-C had intermediate expression. Gene silencing may have occurred in the multiple-copy lines B-16-A and B-19-B (FIG. 6).

Figure 7:
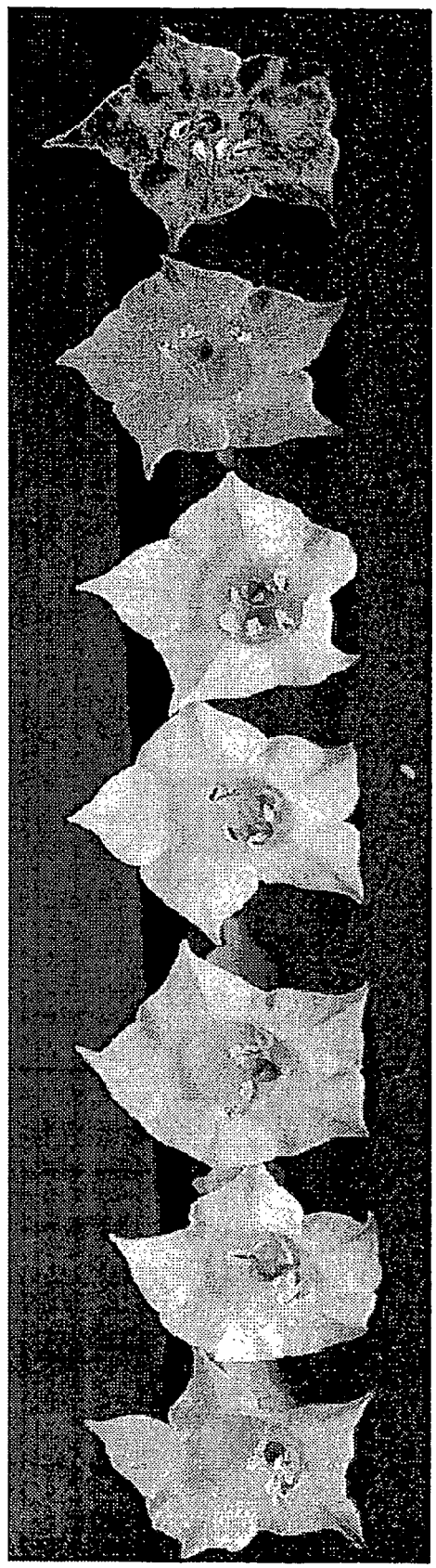
FIG. 7: Shows flower petal coloration for wild-type and BAN transgenic tobacco plants. The plants were: 1, wild-type; 2, B-11; 3, B-17-A; 4, B-19-A; 5, B-21-B; 6, 121-3-A (empty vector control); 7, D-5-C (a transgenic plant over-expressing an *M. truncatula* dihydroflavonol reductase transgene).

About 30% of the transgenic plants showed changes in flower color. A dramatic change from red or pink to white occurred in lines B-11, B-17-A, B-19-A and B-21-B (FIG. 7), but no white flower color was ever observed in non-transgenic control plants (6 lines derived from tissue culture) and vector control transgenic plants (21 lines), although the intensity of red flower coloration did vary. These results demonstrate that ectopic expression of BAN changes flower color, presumably by channeling intermediates away from anthocyanin biosynthesis.

Figure 8:
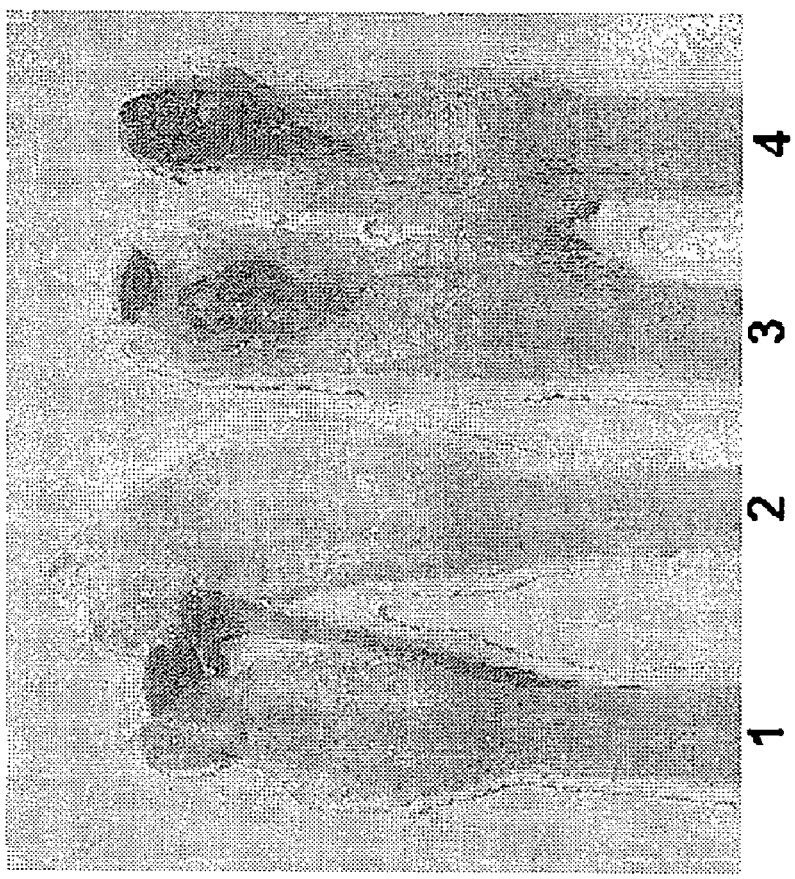
FIG. 8: Shows the presence of CTs in petals of transgenic tobacco expressing *M. truncatula* BAN (3 and 4) in comparison with petals from wild-type plants (1 and 2). Petals were stained with 0.1% DMACA in ethanol/6M HCl (1:1)

Condensed tannins in the petals of transgenic plants were visualized by incubating fresh tissues in 1% vanillin in 5N HCl (Kristensen and Aastrup, 1986) for 30 min in petri dishes, or by staining tissues in a solution of ethanol: 6M HCl (1:1) containing 0.1% (w/v) dimethylaminocinnamaldehyde (DMACA) (Sigma) (Bavage et al. 1997) for 3-6 min, then washing three times with MilliQ water. If CTs are present a blue color develops with DMACA reagent, and the cells containing CTs can be examined under a dissecting microscope. Both vanillin and DMACA staining indicated that BAN transgenic petals contained CTs but that petals from control plants did not. FIG. 8 shows DMACA staining of BAN-transgenic and control petals.

For quantitative analysis of anthocyanins and CTs in transgenic tobacco petals, fresh petals (0.4-0.8 g fresh weight) from three flowers were immersed in 15 ml ethanol: 6M HCl (1:1) in 50 ml screw-cap tubes and extracted at 4° C. in the cold room for 10 hours. The anthocyanin extract solution was removed into new 50 ml screw cap tubes; a further 15 ml ethanol: 6M HCl (1:1) was added and the petal samples extracted for a further 10 hours. The two anthocyanin extractions were pooled together and stored at 4° C. for estimation of anthocyanins from their absorption at 528 nm.

The white petals (after extraction of anthocyanin) were transferred to new 50 ml screw-cap tubes, washed three times in MilliQ water and then immersed in MilliQ water overnight (16 hours) in the cold room. The now semi-transparent white petals were blotted on paper tissue to remove excess water and placed into 15 ml capped tubes. Three ml butanol: concentrated HCl (95:5, v/v) was added to each tube, which was then heated to 100° C. in a water bath for 1 hour, and then cooled to room temperature. The absorbance of the butanol-HCl extract was measured at 550 nm (Carron et al., 1994), and cyanidin was used as standard (Giner-Chavez et al., 1997). The butanol-HCl extract was also dried under vacuum and the residue re-suspended in 200 µl methanol containing 0.1% HCl for HPLC analysis.

Figure 9:
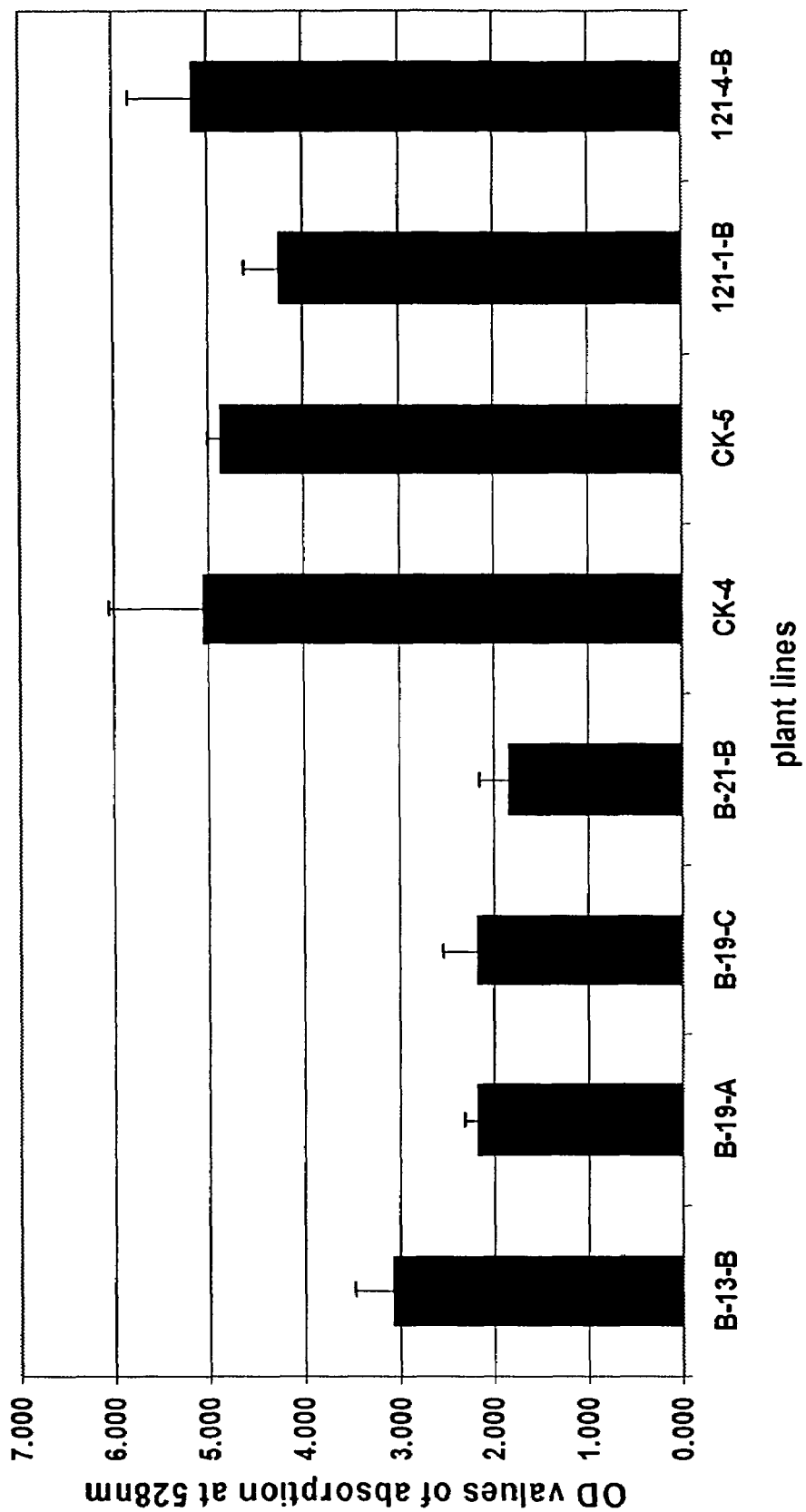
FIG. 9: Shows the levels of anthocyanins in petals of tobacco plants expressing the *M. truncatula* BAN gene (lines designated with B-) compared to empty vector control lines (121- designation) or wild-type plants (CK- designation). Anthocyanins were extracted in ethanolic HCl, and their levels determined by measurement of absorbance at 528 nm.

The levels of anthocyanins in petals of tobacco plants expressing the *M. truncatula* BAN gene were reduced approximately three-fold compared to those in control plants (FIG. 9). The analysis of these transgenic plants was repeated using a modified procedure for extraction and analysis of anthocyanins. Individual tobacco flowers were cut at the base of the swelling below the corolla (the portion of the flower containing the majority of the anthocyanins in wild-type tobacco flowers). To extract the anthocyanin pigments, the upper portion (approximately 1.5 cm) including the corolla from each flower was placed in 10 ml methanol acidified with 0.05% HCl in a plastic screw cap tube and shaken gently at room temperature in the dark for 24 hr. The absorbance of extracts was measured at 528 nm. The results are shown in Table 3, and confirm the reduction in anthocyanin levels in flowers of plants expressing *M. truncatula* BAN. Furthermore, the results in Table 3 also include data on anthocyanin levels in three transgenic lines over-expressing *M. truncatula* dihydroflavonol reductase. In these lines, anthocyanin levels were increased. This can also be seen visually in FIG. 7, plant D-5-C. Thus, although the *M. truncatula* BAN gene has significant sequence similarity to DFR, the phenotypes resulting from over-expression of DFR or BAN are opposite, indicating that *M. truncatula* BAN does not possess DFR activity.

TABLE 3

Anthocyanin levels in petals from transgenic tobacco plants constitutively expressing *Medicago truncatula* BAN or DFR

| Construct | Plant line (# of samples) | Flower Color | Avg. absorbance (528 nm) | Std dev |
|---|---|---|---|---|
| CaMV35S:MtBAN | BAN-21-B (3) | light pink rays | 0.018 | 0.002 |
| CaMV35S:MtBAN | BAN-13-B (3) | light pink overall | 0.037 | 0.005 |
| CaMV35S:MtBAN | BAN-6-C (2) | very pale pink | 0.027 | 0.001 |
| CaMV35S:MtBAN | BAN-19-A (3) | pale pink | 0.017 | 0.004 |
| CaMV35S:MtBAN | BAN-14-A (2) | very pale pink | 0.017 | 0.003 |
| CaMV35S:MtD-DFR | D-DFR-3-C (3) | dark pink | 0.118 | 0.026 |
| CaMV35S:MtD-DFR | D-DFR-5-B (2) | pink | 0.087 | 0.018 |
| CaMV35S:MtD-DFR | D-DFR-2 (2) | pink | 0.111 | 0.017 |
| CaMV35S:GUS | 121-1-C (2) | pink | 0.054 | 0.006 |
| CaMV35S:GUS stock lines: | 121-5-A (2) | pink | 0.067 | 0.019 |
| untransformed | NF+ 0 (2) | pink | 0.072 | 0.018 |
| promoterless GUS | 101-H1 (2) | pink | 0.086 | 0.013 |

After extraction of anthocyanins, petals from transgenic plants expressing the BAN gene produced a red color on boiling in butanol-HCl, but no red color was observed in petals from control plants. UV/visible spectroscopy indicated that petal extracts from the BAN transgenic plants had 2-3 times higher absorption at 550 nm than extracts from control petals. Using cyanidin as external standard, the level of CT in BAN transgenics was between 7.7-42.7 µg cyanidin equivalents per g fresh weight (Table 4).

TABLE 4

Condensed tannin levels in petals of transgenic tobacco expressing the *Medicago truncatula* BAN gene in comparison to levels in empty vector and wild-type controls.

| Tobacco line | CT (µg cyanidin equivalents/g FW) |
| --- | --- |
| Wild-type CK-4 | 1.2 |
| Wild-type CK-5 | 0.8 |
| Empty vector 121-1-B | 0.0 |
| Empty vector 121-4-B | 1.2 |
| B-13-B | 42.7 |
| B-19-A | 14.3 |
| B-19-C | 7.7 |
| B-21-B | 26.6 |

Example 7

Identification of BAN Coding Sequences from Plant Species

Following identification and confirmation of the utility and function of the *M. truncatula* BAN sequence (SEQ ID NO: 1), studies were carried out to identify BAN coding sequences from other plants. Using a genomics-based approach, plant genome databases were scanned for additional BAN coding sequences. Corresponding sequences were identified from barley, *Brassica napus*, Cotton, grape and sorghum. Amino acid sequences of the BAN genes from *M. truncatula* and *A. thaliana* were used to scan TIGR gene indices for different crop plants by a tblastn method. Sequences identified were further aligned by using the Clustal W method, MegAlign DNASTAR program to confirm their homology. Two barley BAN coding sequences were identified using this approach, barley 49014 and barley barley55701; as were two sorghum sequences, designated sorghum TC34457 and TC34925. The coffesponding coding sequences (ORFs) for the barley sequences are given in SEQ ID NO:33 and SEQ ID NO:35 and the polypeptides encoded are given in SEQ ID NO:34 and SEQ ID NO:36, respectively. The coding sequences for sorghum TC34457 and sorghum TC34925 are given in SEQ ID NO:43 and SEQ ID NO:45, and the encoded polypeptides are given in SEQ ID NO:44 and SEQ ID NO:46, respectively. The other sequences identified were as follows: the *Brassica napus* coding sequence is given in SEQ ID NO:37 and the encoded polypeptide is given in SEQ ID NO:38; the cotton coding sequence is given in SEQ ID NO:39 and the encoded polypeptide is given in SEQ ID NO:40; the grape coding sequence is given in SEQ ID NO:41 and the encoded polypeptide is given in SEQ ID NO:42.

Two new BAN sequences were also cloned from barley cv. Morex. Total RNA was isolated from the developing seed testa of barley cv. Morex using a Tri-Reagent kit (Molecular Research Center). Four µg total RNA was used to synthesize first stand cDNA as described in Example 1. Four µl of the first stand cDNA solution was used for PCR reactions using high fidelity Pfu polymerase in combination with gene specific primers for barley BAN (SEQ ID NO: 35) (forward primer: AGGCTGGTGCCACGCGGTTCTTCCATGGCG GCGGGCGAGGGGAGGAAGACGG (SEQ ID NO: 49) and reverse primer: AGATCTAGAACATGTCAATGGCG-CAAAATCCCGGTGCTC) (SEQ ID NO: 50) and barley BAN, SEQ ID NO:33 (forward primer: CAGGCTGGTGC-CACGCGGTTCTTCCATGGCGGCGGCGGCTGGTGAT GGGAC (SEQ ID NO: 51) and reverse primer: AGATCTA-GAGAAGAGCCTGTTATATCAGTAT (SEQ ID NO:52)). The PCR products digested with NcoI and XbaI were cloned into pRTL2. Cloned genes were sequenced and the coding sequences, designated as barley 306 and barley 316, are given SEQ ID NO 29 and SEQ ID NO 31 and the corresponding polypeptides are given SEQ ID NO 30 and SEQ ID NO32.

To confirm the ANR activity for barley 306 and barley 316, the sequences were digested with NcoI restriction enzyme and mung bean nuclease and then with XbaI restriction enzyme and were cloned into *E. coli* expression vector pMAL-C2X digested with XmnI and XbaI, resulting into pMAL-306 and pMAL316, respectively. *E. coli* carrying pMAL-306 and pMAL-316 were induced with 1 mM IPTG for 24 hr at 16° C. and protein extracts from them were assayed for ANR activity as described in Example 8. Both these constructs showed ANR activity by reducing anthocyanidins to (–) epicatechins.

Example 8

Novel Anthocyanidin Reductase Enzyme Activity Assay for the Recombinant Protein Encoded by the *Medicago truncatula* BAN homolog and the *Arabidopsis thaliana* BAN cDNA clones (MtBAN and AtBAN)

The coding region of the *Medicago truncatula* BAN homolog (MtBAN) was subcloned by digesting the original plasmid with NcoI (cuts at the start codon) and XhoI (cuts after the polyA tail), then ligating the fragment into the *E. coli* expression vector pSE380. The plasmid was used to transform *E. coli* BL21-Gold host cells (Stratagene), with 100 µg/ml ampicillin selection. The cDNA clone of the *Arabidopsis thaliana* BAN (AtBAN) was obtained as described above by RT-PCR using primers which introduced NcoI and XbaI sites at 5' and 3' (60 bp after the stop codon) of the BAN ORF, respectively. The PCR products were coned into pGEM-T Easy (Promega). After confirming the BAN ORF sequence, the pGEM-T Easy-BAN plasmid was cut with NcoI and XbaI. The NcoI/XbaI fragment carrying the BAN ORF was purified and ligated into NcoI and XbaI cut *E. coli* expression vector pPROEX-1 (GIBCO, Life Technologies). The ligation mix was used to transform DH5a host cells, with 100 µg/ml ampicillin selection.

A single colony harboring either MtBAN or AtBAN expression constructs or pSE380 (empty vector control) was inoculated into 3 ml LB medium containing ampicillin 100 µg/ml and incubated overnight at 37° C. at 250 rpm. One ml cell suspension was used to inoculate 50 ml LB medium containing ampicillin 100 µg/ml and incubated at 37° C. at 250 rpm until the culture density reached $OD_{600}$=0.3, then incubated at 16° C. or 12° C. at 250 rpm until the culture density reached $OD_{600}$=0.6 to 0.7. IPTG (100 mM stock) was added to each culture to a final concentration of 1 mM to induce protein synthesis. The cultures were incubated an additional 20-23 hrs at the same conditions, and then the cells were collected by centrifugation at 4° C. (induction at higher temperatures resulted in mostly insoluble BAN protein). The pellets were used to extract enzyme or were stored at –20° C. for future enzyme assays.

Cells from 50 ml cultures were lysed by resuspending the cell pellet in 1 ml lysis buffer containing 100 mM Tris-HCl (pH 7.0), and 100 µg/ml lysozyme (from egg-white; Sigma). After 10 min incubation at room temperature, the viscous lysate was sonicated 15-20 sec on ice to shear DNA and homogenize the solution. The suspension was centrifuged 15 min at 4° C. and the supernatant was transferred into new chilled centrifuge tube and kept on ice for further activity and molecular weight assay (SDS-PAGE analysis).

Pelargonidin chloride, cyanidin chloride and delphinidin chloride (Indofine Chemical Company, Inc. (Sommerville, N.J.) were used as substrates for an anthocyanidin reductase activity assay of the recombinant BAN-encoded proteins. Initial assays used the extracts from cultures expressing the MtBAN (*Medicago*) protein. The protein extracts from *E. coli* cultures harboring the empty expression vector pSE380 were used as negative controls. As an additional negative control for the assay, a portion of the MtBAN and vector control protein extracts were boiled in a water bath for 10 min. The enzyme assays were carried out in 1.5 ml polypropylene tubes containing 345 µl 100 mM Tris-HCl pH 7.0, 5 µl pelargonidin chloride, cyanidin chloride or delphinidin chloride (10 mM stock in MEOH), 50 µl NADPH (fresh 20 mM stock) and 100 µl crude enzyme extract (approximately 50 µg protein by BioRad dye-binding protein assay with BSA as a standard). Initial assays were carried out with protein extracts from cultures expressing recombinant MtBAN proteins, or from cultures containing the empty expression vectors, or these extracts after boiling (boiled MtBAN protein or boiled pSE380 vector control proteins). After adding the protein extracts, the assay mixture was mixed well and incubated in a 30° C. water bath for 30 min. The reaction was stopped by adding 1 ml ethyl acetate and vortexing 1 min. Phases were separated by centrifuging at 14,000 rpm 4° C. for 15 min. A portion (0.8 ml) of the ethyl acetate extract (upper phase) was transferred to a new 1.5 ml tube, and the ethyl acetate was evaporated with nitrogen gas at room temperature. The residues were dissolved in 100% methanol (HPLC grade) for HPLC analysis.

HPLC analysis was carried out on a HP1100 HPLC system with a UV/Vis Diode Array detector (Agilent Co., formerly Hewlett-Packard). The HPLC column was a reverse phase C18 (MetaChem "Waters" Spherisorb ODS 5 um 250×4.6 mm) and the solvents were 1% $H_3PO_4$ (solvent A) and acetonitrile ($CH_3CN$) (solvent B). The HPLC program consisted of the following percentages of $CH_3CN$ (B): equilibration and first 5 min after injection, 5% B; from 5 to 7 min, linear increase to 7% B; hold at 7% B until 25 min; from 25 to 40 min, linear increase to 40% B; from 40 to 40.5 min (wash cycle begins), linear increase to 95% B, hold at 95% B until 49.5 min, and linear return to 5% B (initial conditions) from 49.5 to 50 min. After a 10 min re-equilibration, the next sample was injected. The flow rate was 1.5 ml/min and the injection volume was 30 µl. Standards of (±)-catechin or (−)-epicatechin, gallocatechin, epigallocatechin (Sigma) were used for comparison of HPLC retention times and UV diode array spectra in the assay.

Figure 10:
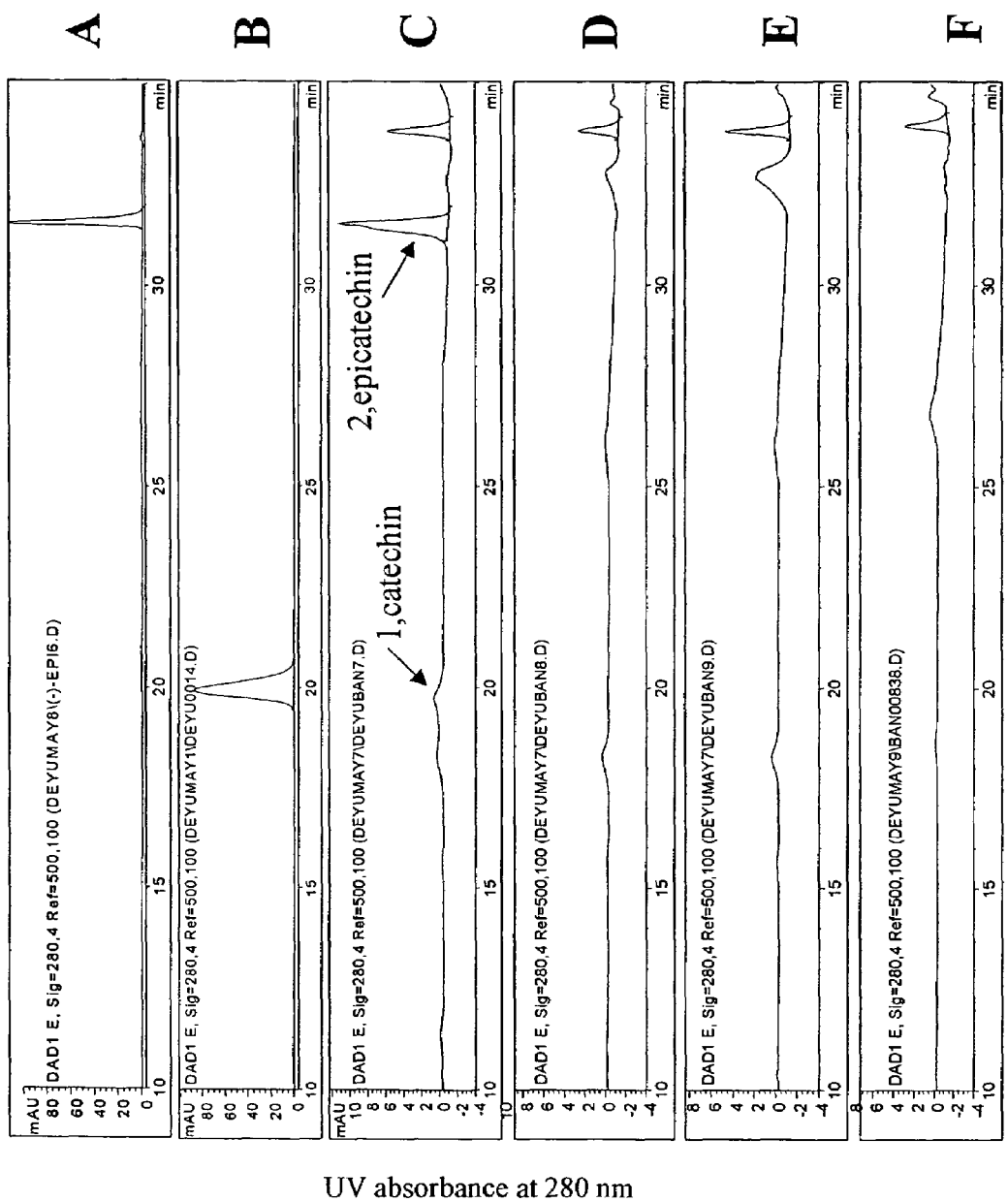
FIG. 10: MtBAN catalyzes the conversion of cyanidin into catechin and epicatechin. Standards for epicatechin (A) and catechin (B); reaction products from MtBAN enzyme (C); boiled MtBAN enzyme (D); pSE380 vector control protein extract (E); boiled pSE380 vector control protein extract (F).
Figure 11:
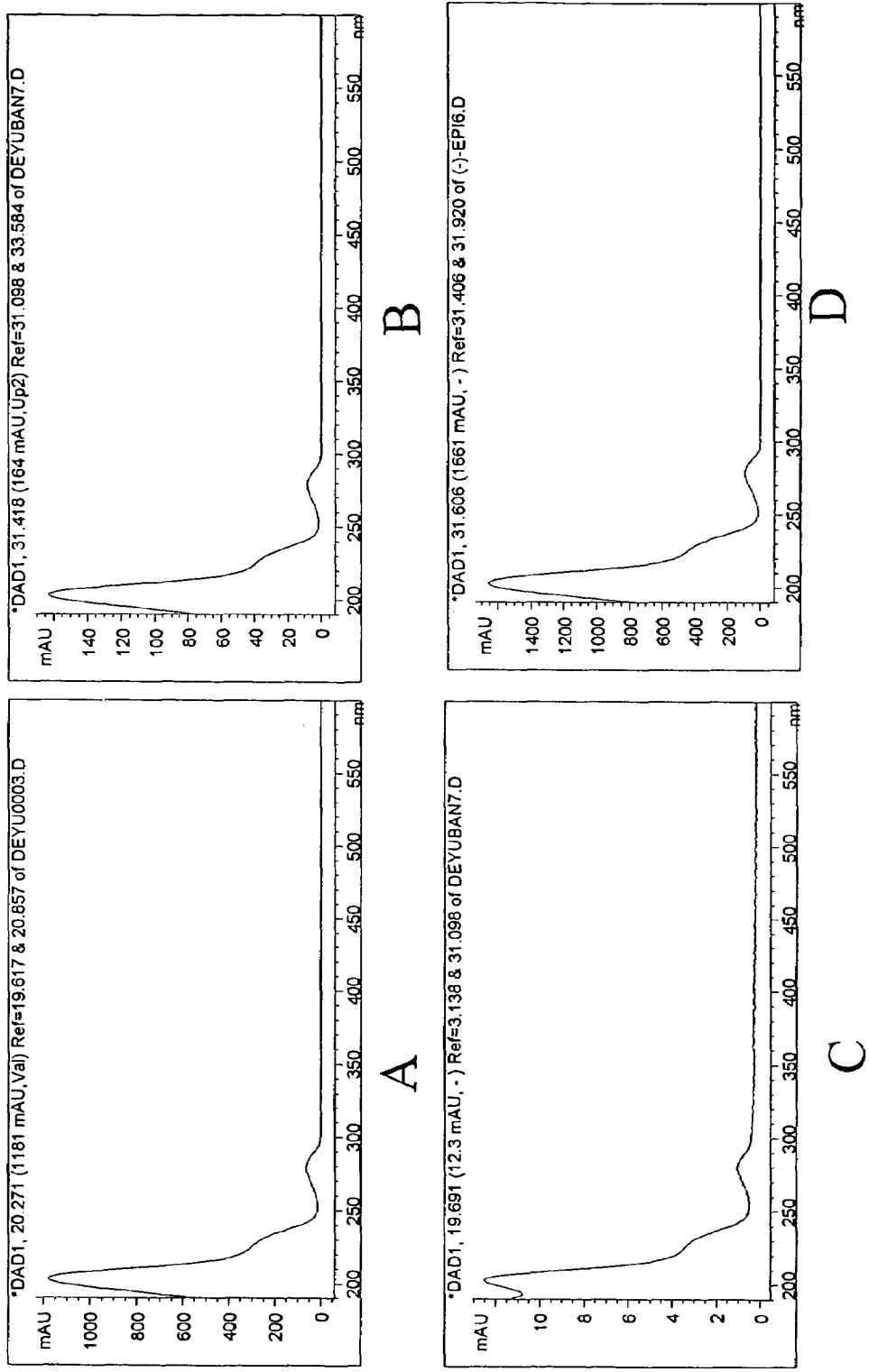
FIG. 11: Comparison of UV spectra of (±) catechin (A) and (−) epicatechin (B) standards and enzymatic products of MtBAN acting on cyanidin (C, 19.6 min product, putative catechin and D, 31.9 min product, putative epicatechin)

After 30 min incubation at 30° C. of the enzyme assay mixture containing MtBAN protein extract, NADPH, cyanidin, and buffer, two new peaks appear in the HPLC chromatogram, which are not present in chromatograms from assays with the pSE380 control protein extracts, or with boiled (inactivated) MtBAN extracts or boiled pSE380 extracts (FIG. 10; note that the y-axes are in mAU at 280 nm, and that the scale varies with the samples). The major new peak eluted at approximately 31.6 min. This retention time matches that of the epicatechin standard in this system and had a UV diode array spectrum matching that of epicatechin (FIG. 11). A broad minor new peak eluted at approximately 20 min, matching the retention time and UV spectrum of the catechin standard (FIG. 10 and FIG. 11). Therefore, the MtBAN protein was concluded to be a novel, previously unexpected, anthocyanidin reductase, in this case reducing cyanidin to the corresponding flavan-3-ols, catechin and epicatechin, in vitro. In addition to acting on free anthocyanidins, MtBAN may also act on anthocyanins (anthocyanidins with 3-glucose substitution).

When NADPH was omitted from the enzyme assay mixtures, no conversion of anthocyanidins to flavan-3-ols was observed, indicating that the enzyme reaction is NADPH-dependent. When NADH (2 mM, final concentration) was substituted for NADPH, some conversion was observed (approximately 50% of the level achieved with NADPH at the same concentration), indicating that the enzyme may use other reducing co-factors.

Figure 12:
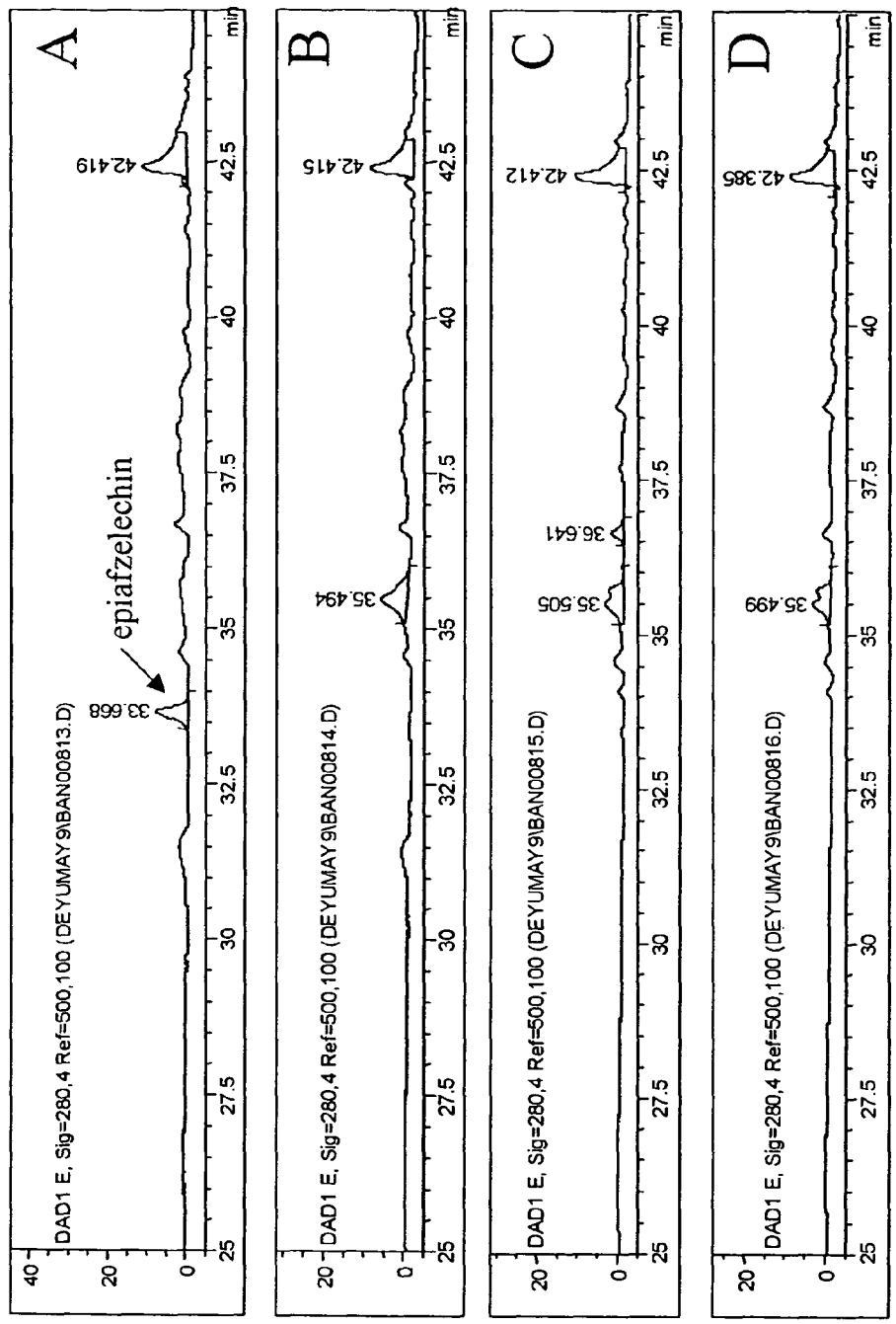
FIG. 12: MtBAN catalyzes the conversion of pelargonidin into afzelechin. A, reaction products from MtBAN enzyme extract, with putative epiafzelechin peak labeled; B, pSE380 vector control enzyme extract; C, boiled MtBAN enzyme extract; D, boiled pSE380 vector control enzyme extract.
Figure 13:
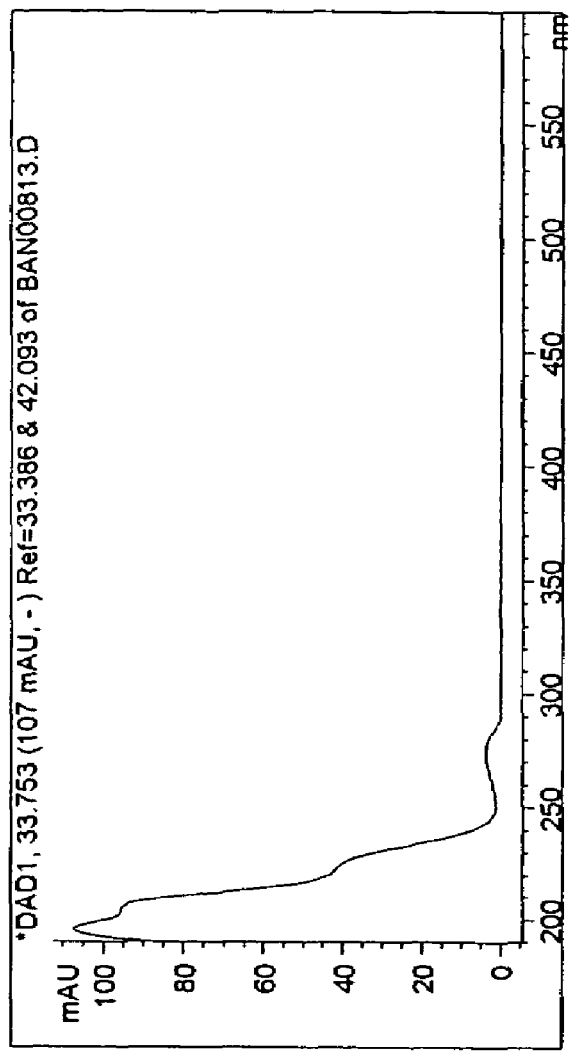
FIG. 13: UV spectrum of putative epiafzelechin peak.

MtBAN protein extracts also catalyzed the reduction of pelargonidin into a new compound eluting at 33.6 min, but negative control proteins (pSE380, boiled MtBAN and boiled pSE380) do not produce this product (FIG. 12). This peak was tentatively identified as epi-afzelechin, the flavan-3-ol corresponding to pelargonidin, based on relative retention time and UV spectra (FIG. 12 and FIG. 13). MtBAN protein extracts also catalyzed the reduction of delphinidin into putative gallo-catechin and epi-gallocatechin (FIG. 14 and FIG. 15). No formation of any of these products were observed in the reaction mixtures with negative control protein extracts.

Figure 19:
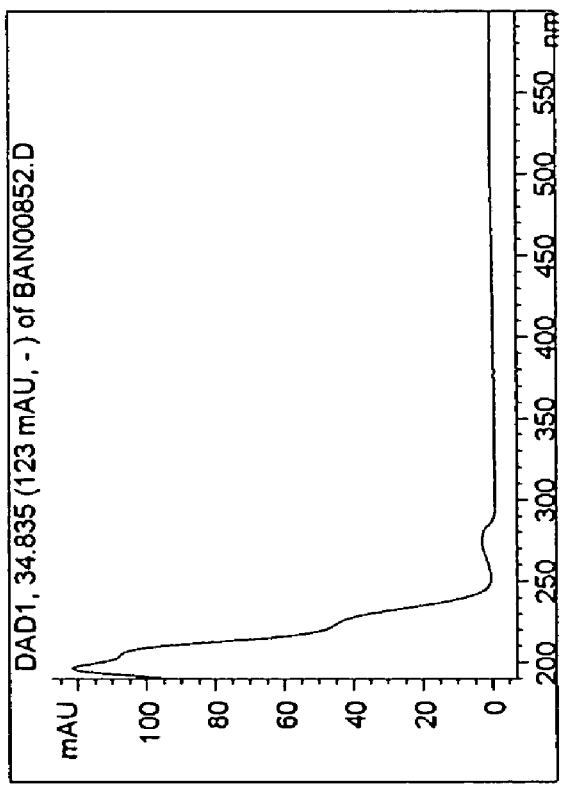
FIG. 19: UV spectrum of AtBAN enzymatic reaction product, putative epiafzelechin
Figure 20:
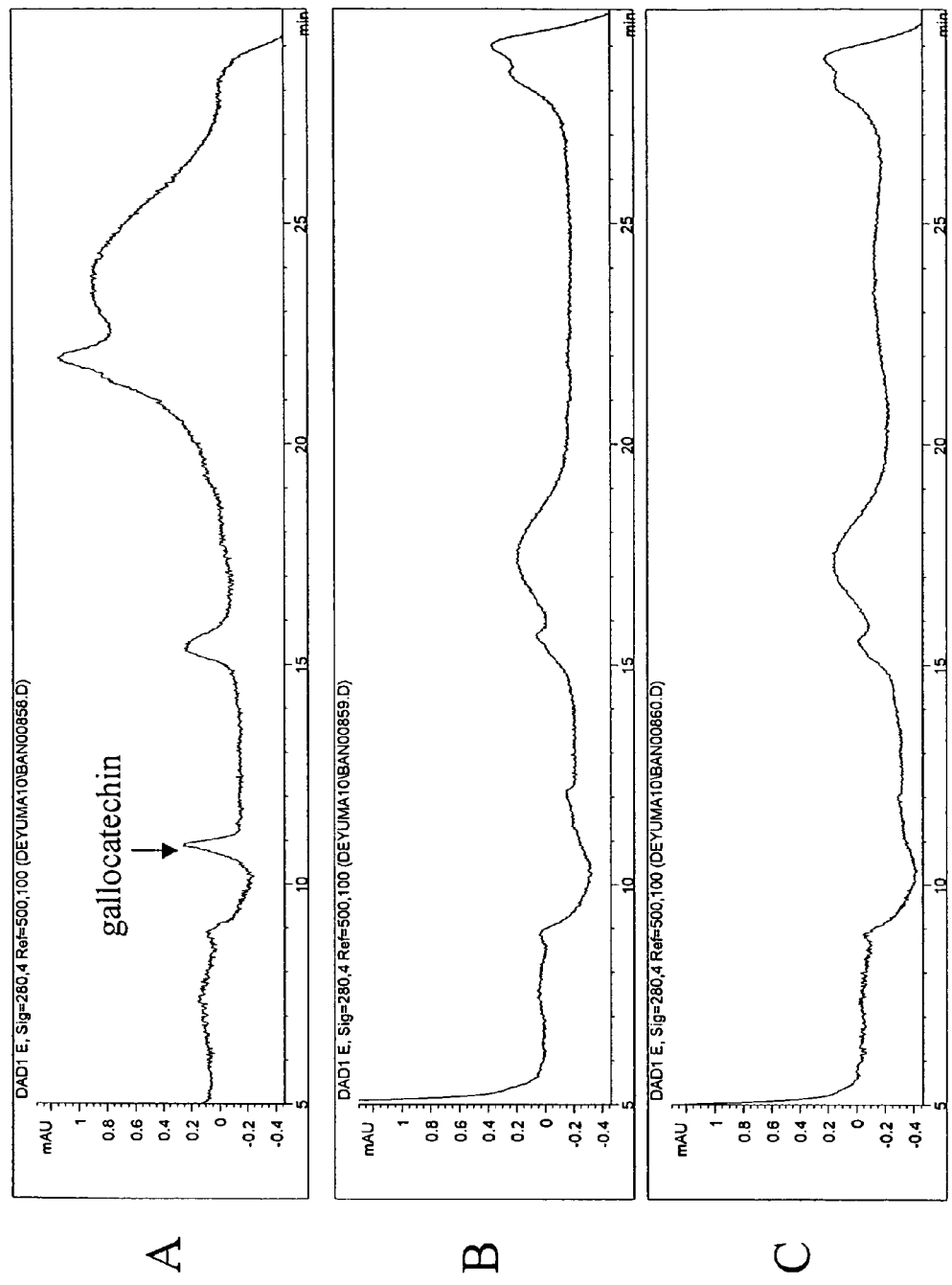
FIG. 20: AtBAN catalyzes the conversion of delphinidin into gallocatechin, NADPH used as coenzyme. A, reaction products from BAN enzyme extract; B, boiled enzyme extract; C, vector control enzyme extract.
Figure 21:
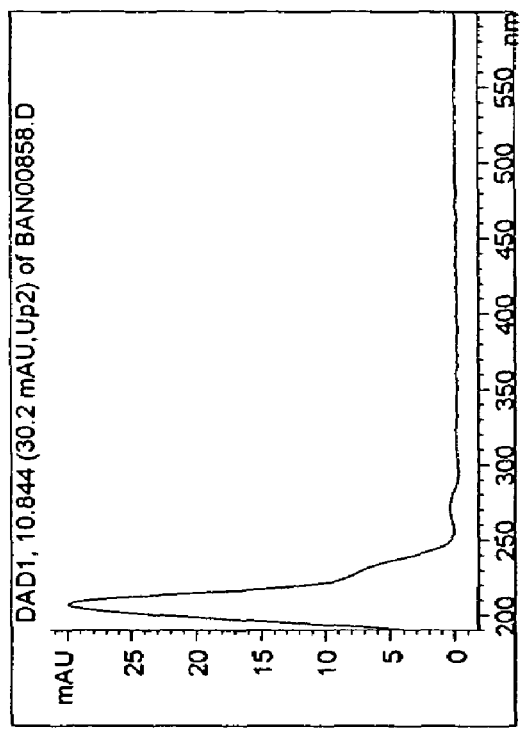
FIG. 21: UV spectrum of AtBAN enzyme reaction product, putative gallocatechin.

The anthocyanidin reductase assay was repeated with extracts from cultures expressing the AtBAN (*Arabidopsis*) protein. The protein extracts from *E. coli* cultures harboring the empty expression vector pPROEX-1 were used as negative controls, or these extracts after boiling. As was shown for the MtBAN extracts, protein extracts from cultures expressing the AtBAN protein were able to catalyze the reduction of cyanidin to epicatechin (FIG. 16 and FIG. 17), pelargonidin into epi-alfzelechin (FIG. 18 and FIG. 19), and delphinidin into gallocatechin (FIG. 20 and FIG. 21). The lower amounts of reaction products recovered from the AtBAN reactions may be due to the fact that 4 month old frozen protein extracts were used in the assay, and additional products, like those observed with MtBAN extracts, may be observed with a more active AtBAN enzyme preparation.

Figure 22:
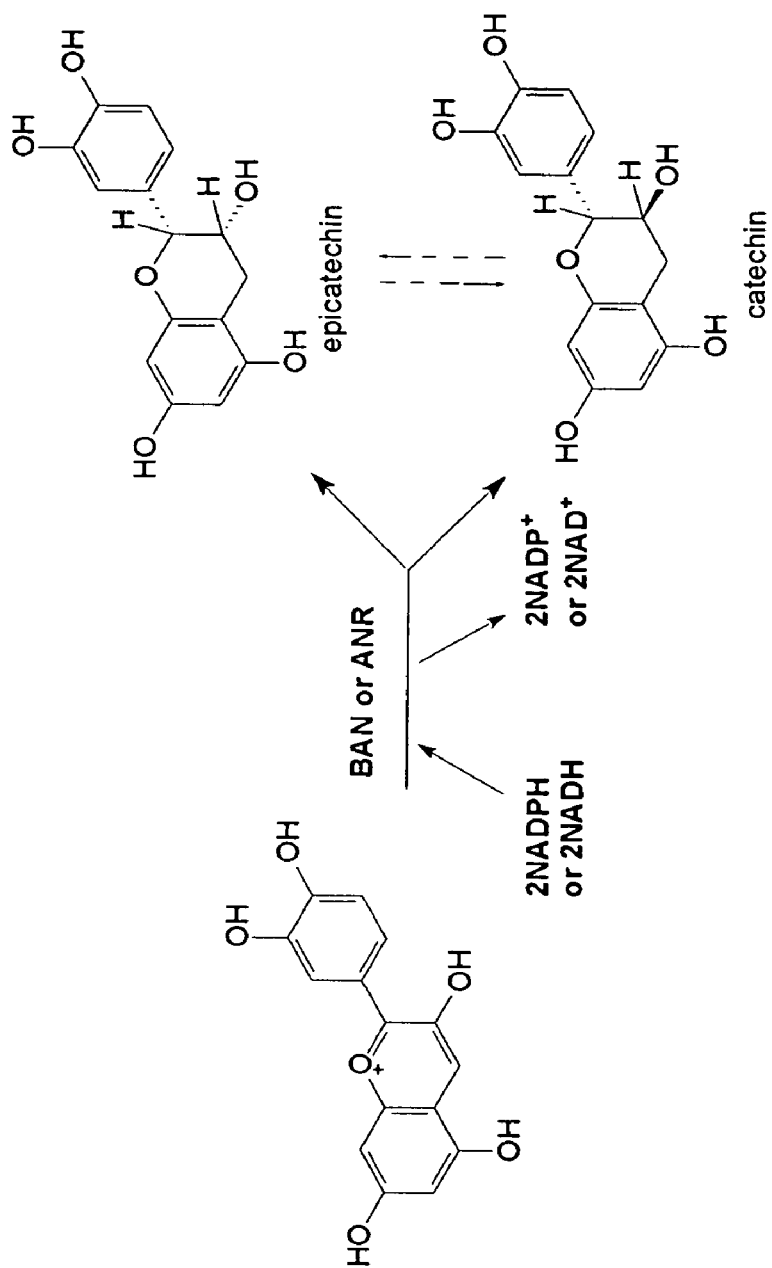
FIG. 22: Schematic presentation of BAN catalyzing the conversion (anthocyanin reductase reaction) of cyanidin into epicatechin and catechin

The results demonstrate that the BAN gene encodes a novel enzyme of anthocyanidin reductase catalyzing the reduction of anthocyanidins into flavan-3-ols, which can then be polymerized into condensed tannins. The overall reaction is described in FIG. 22. For the cyanidin and pelargonidin substrates, the major product accumulating in vitro appears to be the "epi" (2R,3R) configuration (hydroxyl at the 3 position and aromatic ring at 2 position are cis) of the flavan-3-ol, although some product with the trans configuration (2S,3R) is also observed. Incubating the "epi" (2R,3R) configuration- (−) epicatechin or (2R, 3S) (+)-catechin with MTBAN or AtBAN in the presence of NADPH does not produce (2S,3R) configuration (−) catechin or (−) epicatechin, indicating that BAN converts cyanidin into both (−) epicatechin as major product and (−) catechin as minor products. In cases where two product peaks were observed, the ratio of the areas of the two product peaks (putative isomers) varied from study to study. The identity and exact stereochemistry of the product peaks is being further confirmed by LC-MS analysis and other methods.

Using a similar C-18 HPLC column and gradient with one half the flow rate, LC-MS analysis of the products from large-scale reactions of MtBAN enzyme acting on pelargonidin, cyanidin and delphinidin was carried out. For cyanidin as substrate, the two product peaks generated molecular ions, fragmentation patterns and retention times matching those of the catechin and epicatechin standards, and for delphinidin as substrate, the two product peaks generated molecular ions, fragmentation patterns and retention times matching those of the gallocatechin and epigallocatechin standards. For pelargonidin as substrate, no product standards were available for comparison, but two peaks consistent with the molecular weight of afzelechin or epi-afzelechin (16 mass units lighter than the catechin standard) were observed.

During repeated attempts, no LAR activity was observed in reactions containing leucoanthocyanidins and recombinant MtBAN or AtBAN proteins. It could not, however, be ruled out that this LAR enzyme activity exists in plant cells. It was demonstrated that the introduction of the BAN-encoded anthocyanidin reductase activity was sufficient to confer the accumulation of condensed tannins in plants cells, particularly those already accumulating anthocyanins (Example 6; FIG. 8). Heterologous expression of MtBAN in transgenic tobacco flowers generated condensed tannins in corolla and simultaneously decreased anthocyanins, consistent with the anthocyanidin reductase activity herein elucidated for BAN.

It has previously been reported that the enzyme leucoanthocyanidin reductase (LAR), catalyzing the reduction of leucoanthocyanidins into flavan-3-ols such as catechin (FIG. 1), is a component of condensed tannins synthesis (Stafford, 1990). The BAN gene product was suggested to be LAR in previous instances because ban mutants of *Arabidopsis* no longer produce condensed tannins in seed coats, the predicted protein sequence was similar to DFR, and the seeds accumulated higher levels of anthocyanins, consistent with the loss of LAR allowing more leucoanthocyanidins to go to anthocyanin accumulation (Devic, 1999). Prior to this, BAN was thought to encode a negative regulator (transcription factor) of anthocyanin biosynthesis (Alberts, 1997). The BAN gene cDNA and genomic fragments were previously cloned from *Arabidopsis* (Devic, 1999), but there has not been a direct demonstration of its biochemical fluctions with regard to condensed tannins biosynthesis, nor any previous demonstration that its over-expression or ectopic expression confers accumulation of condensed tannins in tissues that do not naturally accumulate condensed tannins.

Figure 23:
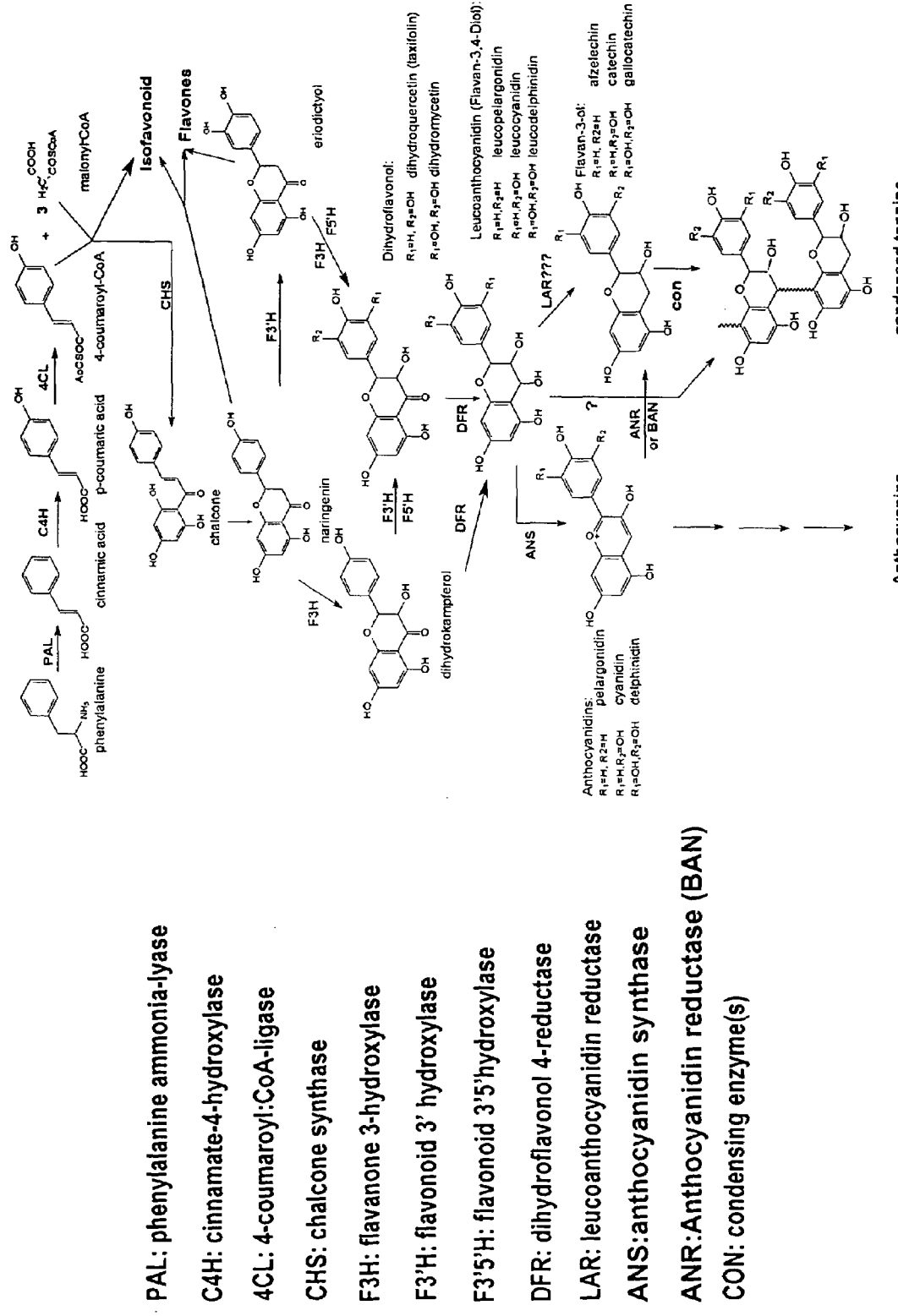
FIG. 23: Proposed modified condensed tannins biosynthetic pathway. ANR (BAN) catalyzes the conversion of anthocyanidins into flavan-3-ols which are then incorporated into condensed tannins. PAL: phenylalanine ammonia-lyase; C4H: cinnamate-4-hydroxylase; 4CL: 4-coumaroyl:CoA-ligase; CHS: chalcone synthase; F3H: flavanone 3-hydroxylase; F3'H: flavonoid 3' hydroxylase; F3'5'H: flavonoid 3'5'hydroxylase; DFR: dihydroflavonol 4-reductase; LAR: leucoanthocyanidin reductase; ANS:anthocyanidin synthase; ANR:Anthocyanidin reductase (BAN); CON: condensing enzyme(s).
Figure 26:
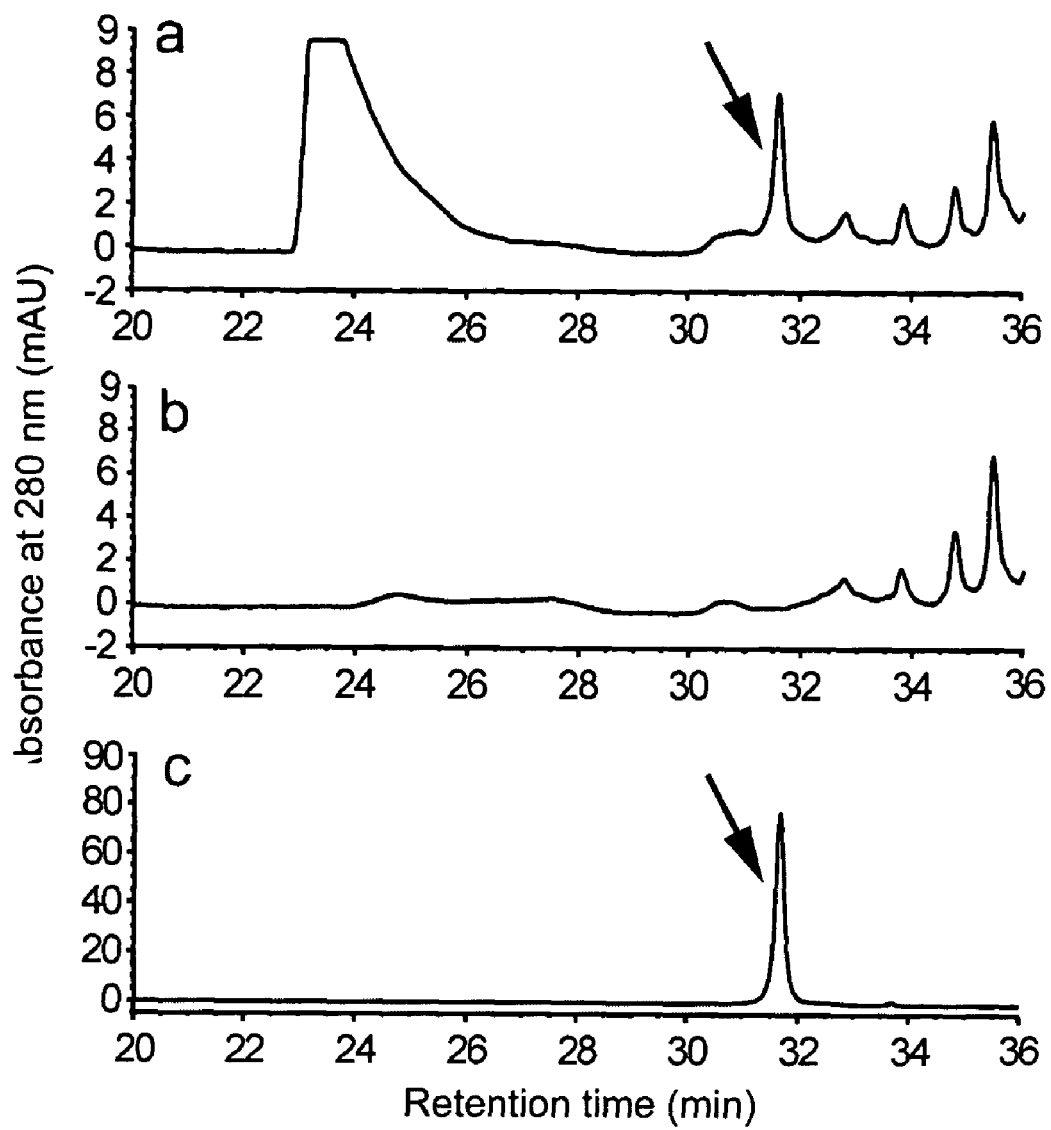
FIG. 26: Anthocyanidin reductase in *Lotus corniculatus*. HPLC analysis showed that ANR converts cyaniding into epicatechin. a, the incubation of extract with cyanidin and NADPH producing epicatechin (arrow); b, the incubation of boiled extract with cyandin and NADPH; c, authentic standard epicatehin (arrow).
Figure 27:
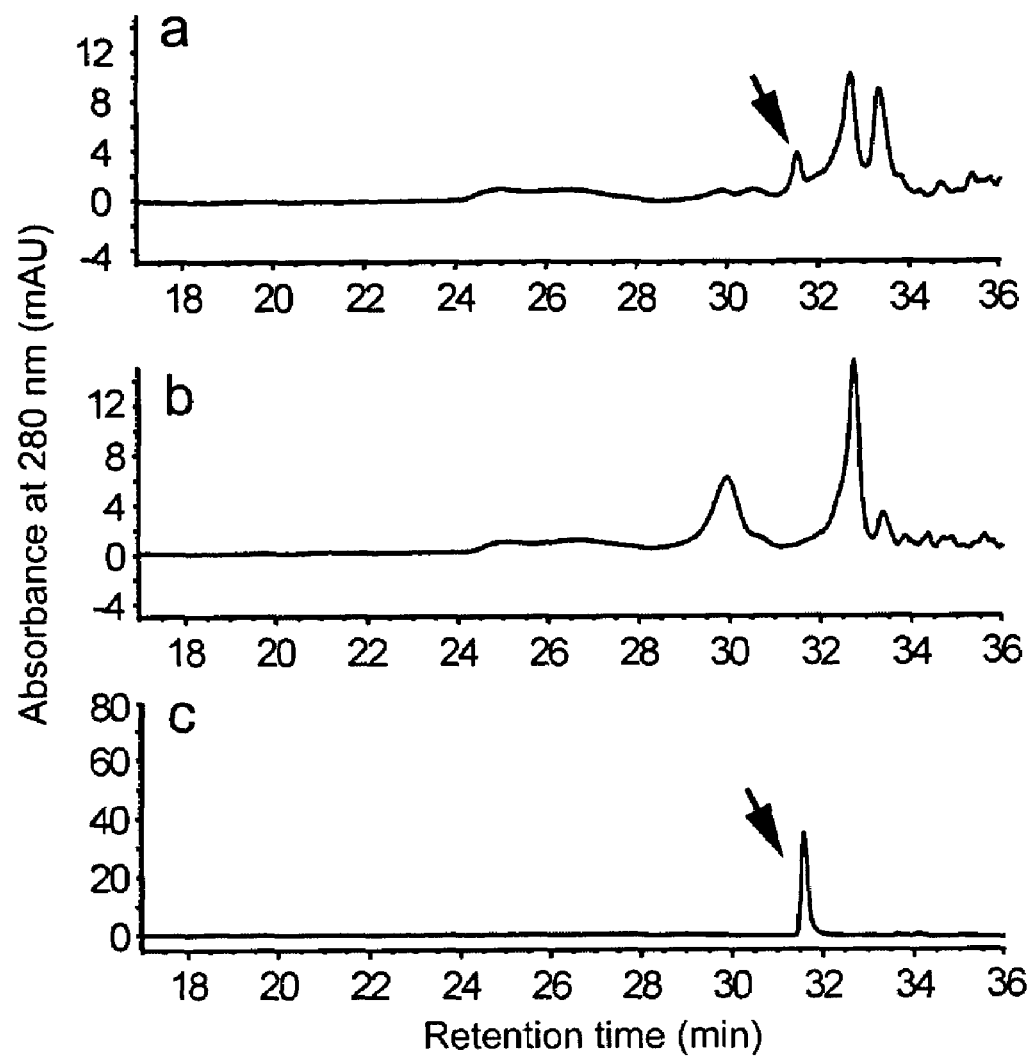
FIG. 27: Anthocyanidin reductase in grape fruit skin of *Vitis vinifer*. a, the incubation of extract with cyanidin and NADPH producing epicatechin (arrow); b, the incubation of boiled extract with cyandin and NADPH; c, authentic standard epicatehin (arrow).
Figure 28:
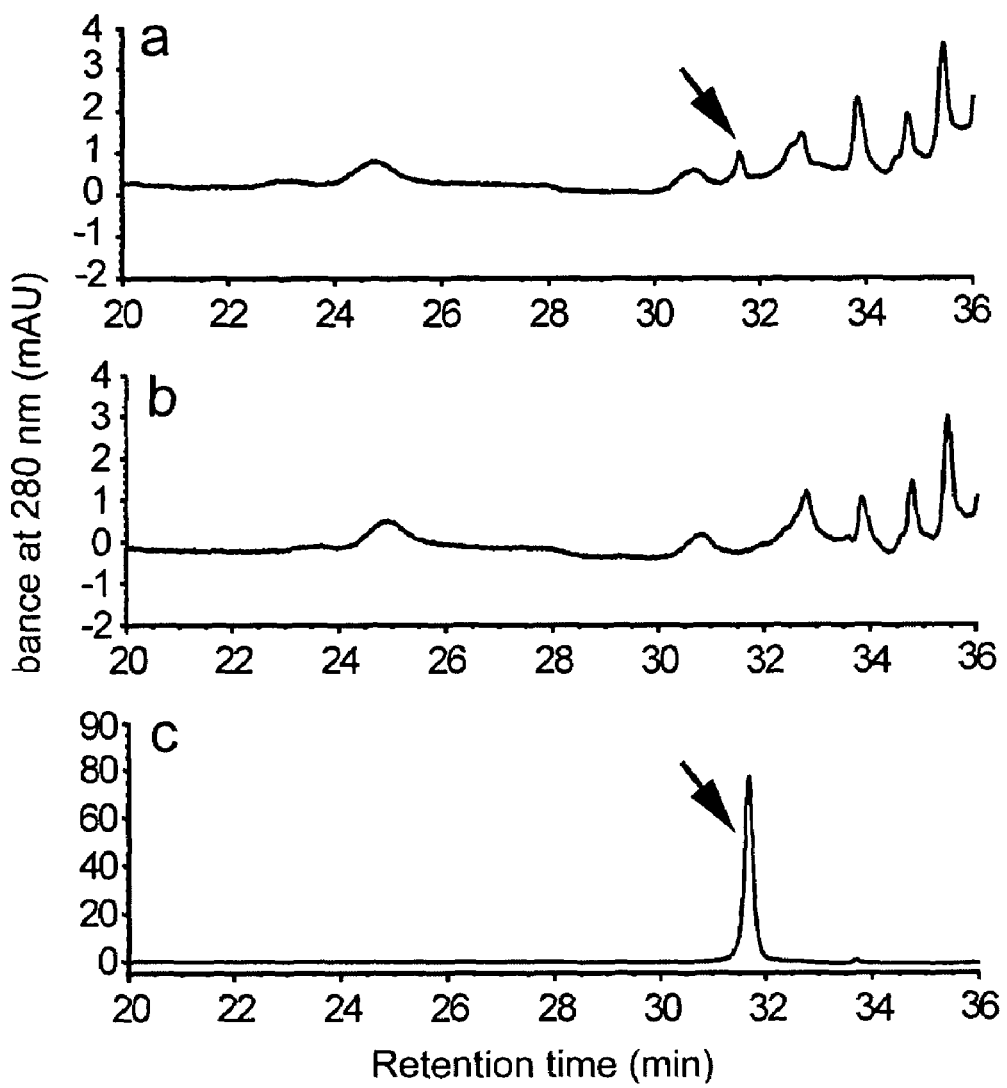
FIG. 28: Anthocyanidin reductase in testa tissue of *Hordeum vulgera* (barley) cv. morex. a, the incubation of extract with cyanidin and NADPH producing epicatechin (arrow); b, the incubation of boiled extract with cyandin and NADPH; c, authentic standard epicatehin (arrow).
Figure 29:
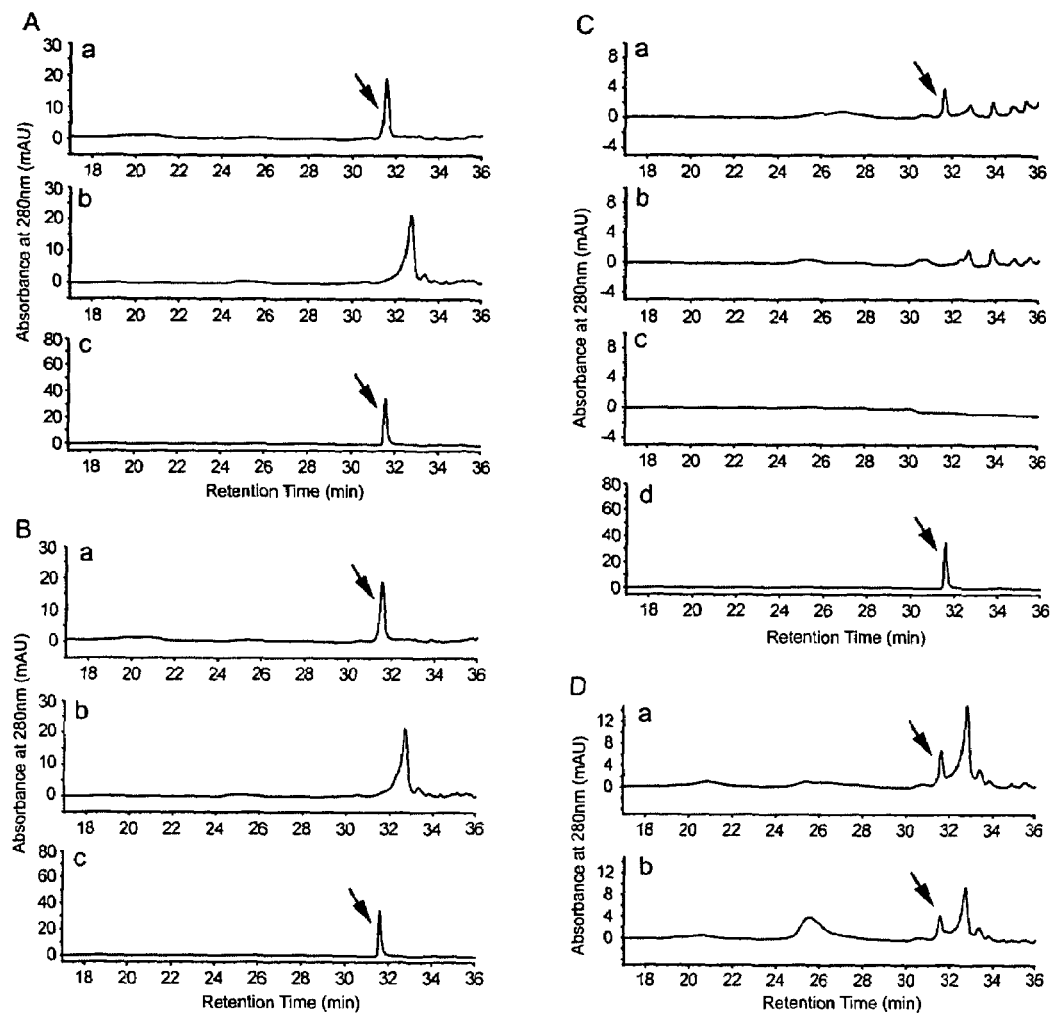
FIG. 29A-D: Anthocyanidin reductase (ANR) in different tissues of *Desmodium uncinatum*.

The condensed tannin and anthocyanin biosynthetic pathways may interact as now described in FIG. 23, with the BAN-encoded anthocyanidin reductase (ANR) now acting upon anthocyanidins (the product of ANS, anthocyanidin synthase, or LDOX, leucoanthocyanidin oxidase), instead of competing for the leucoanthocyanidin pathway intermediates. Anthocyanin (anthocyanidin-3-O-glucosides) and anthocyanidins accumulation is thus reduced by way of conversion of the anthocyanidins to flavan-3-ols.

Example 9

Anthocyanidin Reductase in Different Crop Species

*Lotus corniculatus, Desmodium uncinatum* and Barley cv. Morex were grown in a green house. Young leaves from *L. corniculatus*, unexpanded leaves, and young pods as well as open flowers and flower buds from *D. uncinatum*, and young grains from Barley were collected. Testa of barley grains were excised and pooled together for enzyme extraction. Mature grape fruit stored at −80° C. was treated in pH 7 100 mM Tris.HCl buffer for 30 seconds for isolated the skin for enzyme extraction.

A fresh one-gram leaf sample of *L. corniculatus*, one-gram testa from barley, and 9 grams of grape fruit skin, as well as two grams of flowers, 3 grams of young pods and 3 grams of young unexpanded leaves from *Desmodium uncinatum* were ground into homogenate fine powder in liquid nitrogen. The follow buffer systems were used for enzyme extraction. Extraction buffer 1: pH7 100 mM Tris.HCl, 10% glycerol and 2 mM 1,4-dithiothreitol; Extraction buffer 2: pH8 50 mM phosphate buffer, 10% glycerol, 1.5% polyethyleneglycerol 4000 (PEG-4000), 2 mM pH 8.0 Na-DETA, 25 mM sodium ascorbate, 20 mM β-mecaptoenthanol, and 5 mM 1,4-dithiothreitol; Extraction buffer 3: pH8 100 mM Tris.HCl, 10% glycerol 1.5% polyethyleneglycerol 4000 (PEG-4000), 2 mM pH 8.0 Na-DETA, 25 mM sodium ascorbate, 80 mM β-mecaptoenthanol, and 5 mM 1,4-dithiothreitol.

The homogenate powder of lotus leaf and barley testa tissue was suspended in 5 ml extraction buffer 1, in which 1% proteinase inhibitor (Sigma) (V/V) was added. The homogenate powder of flowers and pods from *Desmodium* was suspended in extraction buffer 2, also in which 1% proteinase inhibitor (Sigma) (V/V) was added. The fine powder of Desmodium leaves or grape fruit skin was respectively suspended in 6 ml or 50 ml extraction buffer 3, in which 1% proteinase inhibitor (Sigma) (V/V) is added. The homogenates were vortexed vigorously and stayed on ice for 5-10 mm, squeezed through microcloth into 50 ml tubes and then 1/5 (W/V) equilibrated Dowex 1×2 was added into collected squeezed mixture solution. The samples were vigorously vortexed, and then centrifuged at 4° C. at 13000 rpm (20,000 g) for 30 mm. The supernatants were mixed with extraction buffer equilibrated polyvinylpyrrolidone (PVP) with a ratio of 1/5 (W/V) and then centrifuged at 4° C. at 14000 rpm (23,000 g) for 30 mm. The supernatants were desalted on an PD-10 sephadex G-25 column (Amercia Pharmacia) equilibrated and eluted with 100 mM Tris.HCl, 2 mM DTT, 5 mM sodium ascorbate and 10% glycerol following the manufacturer's protocol. The desalted enzyme was concentrated with a 10K MW membrane column (Amicon Ultra, MilliQ) to 0.5-1 ml for enzyme assay.

Enzyme assay was carried out in 200 μl in the formula of pH 7 100 mM Tris HCl, 1 mM NADPH, 100 μM cyanidin and 50-25 μg desalted crude enzyme, 30° C. for 30 min. The reaction was stopped by adding 1 ml ethyl acetate and vortexing 1 min vigorously, and then centrifuged 1 min at 10000 rpm. 0.9 ml ethyl acetate extraction phase was dried with liquid nitrogen and the residues were dissolved in 50 μl methanol, of which 40 μl volume was used for HPLC assay using the same program as above (example 8).

The results of the analysis are presented in FIGS. 26-29, and show that anthocyanidin reductase from all tissues from above plants converted cyanidin into epicatechin. The results indicated a conserved BAN function among plants and indicated the ability to engineer plants by heterologous BAN expression in general.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,188,642
U.S. Pat. No. 5,302,523
U.S. Pat. No. 5,322,783
U.S. Pat. No. 5,384,253
U.S. Pat. No. 5,464,765

U.S. Pat. No. 5,508,184
U.S. Pat. No. 5,508,468
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
U.S. Pat. No. 5,633,448
EPA App. 154,204, 1985
PCT App. WO 97/41228
PCT App. WO 94/09699
PCT App. WO 95/06128
PCT App. WO 97/04103
PCT App. WO 92/17598
Abdullah et al., *Biotechnology*, 4:1087, 1986.
Albert et al., *Plant J.*, February; 11(2):289-99, 1997.
Albrecht and Muck, *Crop Science*, 31:464-469, 1991.
Bagchi et al., *Toxicology*, 148:187-97, 2000.
Barry and McNabb, *Brit. J. Nutr.* 81:263-72, 1999.
Bates, *Mol. Biotechnol.*, 2(2):135-145, 1994.
Battraw and Hall, *Theor. App. Genet.*, 82(2):161-168, 1991.
Bavage et al., *Plant Mol. Biol.* 35:443-458, 1997.
Bevan et al., *Nucleic Acids Research*, 11 (2):369-385, 1983.
Bhattacharee; An; Gupta, *J. Plant Bioch. and Biotech.* 6, (2):69-73. 1997.
Borevitz et al., *Plant Cell*, 12:2383-2393, 2000.
Bouchez et al., *EMBO Journal*, 8(13):4197-4204, 1989.
Bower et al., *The Plant Journal*, 2:409-416. 1992.
Buchanan-Wollaston et al., *Plant Cell Reports* 11:627-631. 1992
Buising and Benbow, *Mol Gen Genet*, 243(1):71-81. 1994.
Callis, Fromm, Walbot, *Genes Dev.*, 1:1183-1200, 1987.
Carron et al., *Theor. App. Genet.*, 87:1006-1015, 1994.
Casa et al., *Proc. Nat'l Acad. Sci. USA*, 90(23):11212-11216, 1993.
Chandler et al., *The Plant Cell*, 1:1175-1183, 1989.
Christou; et al., *Proc. Nat'l Acad. Sci. U S A*, 84(12):3962-3966, 1987.
Chu et al., *Scientia Sinica*, 18:659-668, 1975.
Church, and Gilbert, *Proc. Natl. Acad. Sci. USA*, 81:1991-1995, 1984.
Clough and Bent, *Plant J.*, 16:735-743, 1998.
Conkling et al., *Plant Physiol*, 93:1203-1211, 1990.
Dalzell and Kerven, *J. Sci. Food Agric.*, 78:405-416, 1998.
De Block et al., *The EMBO Journal*, 6(9):2513-2518, 1987.
De Block, De Brouwer, Tenning, *Plant Physiol.*, 91:694-701, 1989.
Debeaujon et al., *Plant Cell*, 13:853-872, 2001.
Dellaporta et al., In: *Chromosome Structure and Function: Impact of New Concepts, 18th Stadler Genetics Symposium*, 11:263-282, 1988.
Devic et al., *Plant J.*, 19:387-398, 1999.
D'Halluin et al., *Plant Cell*, 4(12):1495-1505, 1992.
Ebert et al., 84:5745-5749, *Proc. Nat'l Acad. Sci. USA*, 1987.
Ellis et al., *EMBO Journal*, 6(11):3203-3208, 1987.
Foo et al., *Phytochemistry*, 54:173-81, 2000.
Fraley et al., *Bio/Technology*, 3:629-635, 1985.
Fromm et al., *Nature*, 319:791-793, 1986.
Gallie et al., *The Plant Cell*, 1:301-311, 1989.
Gamborg et al., *Exp. Cell Res.*, 50, 151-158, 1968.
Gelvin et al., In: *Plant Molecular Biology Manual*, 1990.
Ghosh-Biswas et al., *J. Biotechnol.*, 32(1):1-10, 1994.
Giner-Chavez et al., *J. Sci. Food Agric.*, 74:359-368, 1997.
Hagio, Blowers, Earle, *Plant Cell Rep.*, 10(5):260-264, 1991.
Hamilton et al., *Proc. Natl. Acad. Sci. USA*, 93(18):9975-9979, 1996.
Haseloff et al., *Proc. Natl. Acad. Sci. USA*, 94(6):2122-2127, 1997.
He et al., *Plant Cell Reports*, 14 (2-3):192-196, 1994.
Hensgens et al., *Plant Mol. Biol.*, 22(6):1101-1127, 1993.
Hiei et al., *Plant. Mol. Biol.*, 35(1-2):205-218, 1997.
Hinchee et al., *Bio/technol.*, 6:915-922, 1988.
Hou and Lin, *Plant Physiology*, 111: 166, 1996.
Howles, et al., *Plant Physiol.*, 112:1617-1624, 1996.
Hudspeth and Grula, *Plant Mol. Biol.*, 12:579-589, 1989.
Ikuta et al., *Bio/technol.*, 8:241-242, 1990.
Ishidia et al., *Nat. Biotechnol.*, 14(6):745-750, 1996.
Kaeppler et al., *Plant Cell Reports* 9: 415-418, 1990.
Kaeppler, Somers, Rines, Cockburn, *Theor. Appl. Genet.*, 84(5-6):560-566, 1992.
Katz et al., *J. Gen. Microbiol.*, 129:2703-2714, 1983.
Klee, Yanofsky, Nester, *Bio-Technology*, 3(7):637-642, 1985.
Knittel, Gruber; Hahne; Lenee, *Plant Cell Reports*, 14(2-3): 81-86, 1994.
Koupai-Abyazani et al., *J. Agric. Food Chem.*, 41:565-569, 1993.
Kristensen and Aastrup, *Carlsberg Res. Commun.*, 51:509-513, 1986.
Lawton et al., *Plant Mol. Biol.* 9:315-324, 1987.
Lazzeri, *Methods Mol. Biol.*, 49:95-106, 1995.
Lee; Suh; Lee, *Korean J. Genet.*, 11(2):65-72, 1989.
Lin et al., *J. Nat. Prod.*, 65:505-8, 2002.
Lorz et al., *Mol Gen Genet*, 199:178-182, 1985.
Marcotte et al., *Nature*, 335:454, 1988.
McCabe, Martinell, *Bio-Technology*, 11(5):596-598, 1993.
McCormac et al., *Euphytica*, v. 99 (1) p. 17-25: 1998.
McKhann and Hirsch, *Plant Mol Biol.*, 24(5):767-77, 1994
Morris and Robbins, In *Biotechnology and the Improvement of Forage Legumes*, McKersie and Brown (Eds.), CAB International, Wallingford, Conn., pp 147-173, 1997.
Murakami et al., *Mol. Gen. Genet.*, 205:42-50, 1986.
Murashige and Skoog, *Physiol. Plant.*, 15:473-497, 1962.
Nagatani et al., *Biotech. Tech.*, 11(7):471-473, 1997.
Nesi et al., *Plant Cell*, 12:1863-1878, 2000.
Nesi, et al., *Plant Cell*, 13:2099-2114, 2001.
Odell et al., *Nature*, 313:810-812, 1985.
Ogawa et al., *Sci. Rep.*, 13:42-48, 1973.
Omirulleh et al., *Plant Mol. Biol.*, 21(3):415-428, 1993.
Ow et al., *Science*, 234:856-859, 1986.
Pataki et al., *Am. J. Clin. Nutr.*, 75:894-899, 2002.
Potrykus et al., *Mol. Gen. Genet.*, 199:183-188, 1985.
Prasher et al., *Biochem. Biophys. Res. Commun.*, 126(3): 1259-1268, 1985.
Reed, *J. Animal Sci.*, 73:1516-1528, 1995.
Reichel et al., *Proc. Natl. Acad. Sci. USA*, 93 (12) p. 5888-5893. 1996.
Rhodes et al., *Methods Mol. Biol.*, 55:121-131, 1995.
Ritala et al., *Plant Mol. Biol.*, 24(2):317-325, 1994.
Roe, B. A., J. S. Crabtree, and A. S. Khan. 1996. DNA Isolation and Sequencing (Essential Techniques Series). New York: John Wiley & Sons. 176 pp.
Rogers et al., *Methods Enzymol.*, 153:253-277, 1987.
Sagasser et al., *Genes Dev.*, 16:138-149, 2002.
Saito et al., *Plant J.*, 17:181-189, 1999.
Sambrook et al., In: *Molecular Cloning-A Laboratory Manual* (second edition), Cold Spring Harbour Laboratory Press, 1989.
Sambrook et al., *Molecular Cloning: A Laboratory Manual*. (Cold Spring Harbor, N.Y.: Cold Spring Harbor Laboratory Press, 1989.
Sheen et al., *Plant Journal*, 8(5):777-784, 1995.

Singsit et al., *Transgenic Res.*, 6(2):169-176, 1997.
Skadhauge et al., *Am. J. Bot.*, 84:494-502, 1997.
Spencer et al., *Plant Molecular Biology*, 18:201-210, 1992.
Stafford, H. A., Pathway to proanthocyanindins (condensed tannins), flavan-3-ols, and unsubstituted flavans. In: *Flavonoid metabolism* edited by Stafford, H. A., CRC Press. Inc., pp 63-99, 1990.
Stalker et al., *Science*, 242:419-422, 1988.
Sullivan et al., *Mol. Gen. Genet.*, 215(3):431-440, 1989.
Sutcliffe, *Proc. Natl. Acad. Sci. USA*, 75:3737-3741, 1978.
Tanner et al., *Austr. J. Agric. Res.*, 46:1101-1109, 1995.
Thillet et al., *J. Biol. Chem.*, 263:12500-12508, 1988.
Thomas et al., *Plant Sci.* 69:189-198, 1990.
Thompson et al., *Euphytica*, 85(1-3):75-80, 1995.
Thompson et al., *The EMBO Journal*, 6(9):2519-2523, 1987.
Tian, Sequin, Charest, *Plant Cell Rep.*, 16:267-271, 1997.
Tingay et al., *The Plant Journal* v. 11 (6) p. 1369-1376. 1997.
Tomes et al., *Plant. Mol. Biol.* 14(2):261-268, 1990.
Torbet, Rines, Somers, *Crop Science*, 38(1):226-231, 1998.
Torbet, Rines, Somers, *Plant Cell Reports*, 14(10):635-640, 1995.
Toriyama et al., *Theor Appl. Genet.*, 73:16, 1986.
Tsukada; Kusano; Kitagawa, *Plant Cell Physiol.*, 30(4)599-604, 1989.
Twell et al., *Plant Physiol* 91:1270-1274, 1989.
Uchimiya et al., *Mol. Gen. Genet.*, 204:204, 1986.
Van Eck; Blowers; Earle, *Plant Cell Reports*, 14(5):299-304, 1995.
Vasil et al., *Plant Physiol.*, 91:1575-1579, 1989.
Walker et al., *Plant Cell*, 11: 1337-1350, 1999.
Walker et al., *Proc. Natl. Acad. Sci. USA*, 84:6624-6628, 1987.
Wang et al., *Molecular and Cellular Biology*, 12(8):3399-3406, 1992.
Yamada et al., *Plant Cell Rep.*, 4:85, 1986.
Yang and Russell, *Proc. Natl. Acad. Sci. USA*, 87:4144-4148, 1990.
Zheng and Edwards, *J. Gen. Virol.*, 71:1865-1868, 1990.
Zhou et al., *Plant Cell Reports*, 12(11).612-616, 1993.
Zukowsky et al., *Proc. Natl. Acad. Sci. USA*, 80:1101-1105, 1983.

What is claimed is:

1. An isolated nucleic acid molecule comprising a nucleic acid sequence selected from the group consisting of
   a) a nucleic acid sequence encoding the polypeptide of SEQ ID NO:2; and
   b) a nucleic acid sequence comprising the sequence of SEQ ID NO:1.

2. A nucleic acid construct comprising the isolated nucleic acid molecule of claim 1 operably linked to a heterologous promoter.

3. A nucleic acid construct comprising the isolated nucleic acid molecule of claim 1 operably linked to a heterologous terminator.

4. A transgenic plant transformed with a DNA encoding a polypeptide comprising the sequence of SEQ ID NO:2 and having anthocyanidin reductase activity.

5. A transgenic plant which comprises the nucleic acid molecule of claim 1.

6. The transgenic plant of claim 4, defined as exhibiting condensed tannin levels in petals of at least 7.7 µg cyanidin equivalents per gram of fresh weight.

7. The transgenic plant of claim 4, wherein the DNA is operably linked to a heterologous promoter and/or terminator.

8. The transgenic plant of claim 4, wherein said DNA comprises an enhancer and/or a signal peptide.

9. The transgenic plant of claim 4, further defined as a forage crop.

10. The transgenic plant of claim 4, further defined as a monocotyledonous plant.

11. The transgenic plant of claim 4, further defined as a dicotyledonous plant.

12. The transgenic plant of claim 11, wherein said dicotyledonous plant is an alfalfa plant.

13. The transgenic plant of claim 4, wherein the plant is further defined as comprising a transgenic coding sequence encoding a chalcone isomerase polypeptide, wherein the transgenic coding sequence comprises SEQ ID NO:25, SEQ ID NO:26, SEQ ID NO:27 or SEQ ID NO:28.

14. The transgenic plant of claim 4, wherein the plant is further defined as comprising a coding sequence encoding a polypeptide comprising SEQ ID NO:16, SEQ ID NO:18, SEQ ID NO:20, SEQ ID NO:22 or SEQ ID NO:24.

15. The transgenic plant of claim 4, further defined as a fertile $R_0$ transgenic plant.

16. The transgenic plant of claim 4, further defined as a progeny plant of any generation of a fertile $R_0$ transgenic plant, wherein said transgenic plant has inherited a DNA sequence encoding a polypeptide comprising SEQ ID NO:2 from said $R_0$ transgenic plant.

17. A seed of the transgenic plant of claim 4, wherein said seed comprises a DNA sequence encoding a polypeptide comprising SEQ ID NO:2.

18. A method of producing a plant with increased tannin biosynthesis, the method comprising introducing into said plant the isolated nucleic acid molecule of claim 1, wherein the isolated nucleic acid molecule is operably linked to a promoter functional in said plant and wherein the plant comprises increased tannin biosynthesis relative to a second plant that differs from said plant only in that said isolated nucleic acid molecule is absent in the second plant.

19. The method of claim 18, wherein the coding sequence encodes a polypeptide of SEQ ID NO:2.

20. The method of claim 18, wherein the coding sequence comprises a nucleic acid sequence.

21. The method of claim 18, wherein the nucleic acid molecule is operably linked to a heterologous promoter and/or terminator.

22. The method of claim 18, wherein introducing comprises backcrossing.

23. The method of claim 18, wherein introducing comprises genetic transformation with said selected DNA.

24. The method of claim 18, wherein said nucleic acid molecule comprises an enhancer and/or a signal peptide.

25. The method of claim 18, wherein said nucleic acid molecule comprises plasmid DNA.

26. The method of claim 18, wherein the promoter is a constitutive or tissue specific promoter.

27. The method of claim 18, wherein the plant is further defined as a forage crop.

28. The method of claim 18, wherein the plant is further defined as a monocotyledonous plant.

29. The method of claim 18, wherein the plant is further defined as a dicotyledonous plant.

30. The method of claim 29 wherein said dicotyledonous plant is an alfalfa plant.

31. The method of claim 18, further comprising preparing a transgenic progeny plant of any generation comprising said selected DNA.

32. A plant prepared by the method of claim 18.

33. A plant prepared by the method of claim 31.

34. A method of making food for human or animal consumption comprising:
   (a) obtaining the plant of claim 4;
   (b) growing said plant under plant growth conditions to produce plant tissue from the plant; and
   (c) preparing food for human or animal consumption from said plant tissue.

35. The method of claim 34, wherein preparing food comprises harvesting said plant tissue.

36. The method of claim 34, wherein said food is starch, protein, meal, flour or grain.

37. A method for modifying the pigmentation of a plant, the method comprising introducing into said plant the isolated nucleic acid molecule of claim 1, wherein the nucleic acid molecule is operably linked to a heterologous promoter functional in said plant, and wherein the expression of said nucleic acid molecule results in a decrease in anthocyanin pigmentation in the plant relative to a second plant that differs from said plant only in that said nucleic acid molecule is absent in the second plant.

38. The method of claim 37, wherein the nucleic acid molecule comprises the sequence of SEQ ID NO:1.

39. The method of claim 37, wherein the nucleic acid molecule is operably linked to a heterologous promoter.

40. The method of claim 37, wherein the nucleic acid molecule is operably linked to a heterologous terminator.

41. The method of claim 37, wherein said nucleic acid molecule comprises an enhancer and/or a sequence encoding a signal peptide.

42. The method of claim 37, wherein the promoter is a constitutive or tissue specific promoter.

43. The method of claim 37, wherein the plant produces flowers with decreased anthocyanin pigmentation.

44. The method of claim 37, wherein the plant produces seeds having seed coats with decreased anthocyanin pigmentation.

45. The method of claim 37, wherein the plant produces leaves with decreased anthocyanin pigmentation.

46. The method of claim 37, wherein introducing comprises backcrossing.

47. The method of claim 37, wherein introducing comprises genetic transformation with said nucleic acid molecule.

48. The transgenic plant of claim 4, further defined as transformed with a selected DNA encoding an *Arabidopsis thaliana* TT2 polypeptide.

49. The method of claim 18, further comprising introducing into said plant a DNA encoding an *Arabidopsis thaliana* TT2 polypeptide.

50. The method of claim 37, further comprising introducing into said plant a DNA encoding an *Arabidopsis thaliana* TT2 polypeptide.

* * * * *

UNITED STATES PATENT AND TRADEMARK OFFICE
CERTIFICATE OF CORRECTION

PATENT NO. : 7,622,638 B2 Page 1 of 1
APPLICATION NO. : 10/610351
DATED : November 24, 2009
INVENTOR(S) : Dixon et al.

It is certified that error appears in the above-identified patent and that said Letters Patent is hereby corrected as shown below:

In claim 1, column 117, line 3, delete "of" and insert --of:--.

In claim 20, column 118, line 2, delete "sequence." and insert --sequence of SEQ ID NO:1.--.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,622,638 B2
APPLICATION NO. : 10/610351
DATED : November 24, 2009
INVENTOR(S) : Dixon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1715 days.

Signed and Sealed this

Twenty-sixth Day of October, 2010

David J. Kappos
*Director of the United States Patent and Trademark Office*

SEQUENCE LISTING

```
<160> NUMBER OF SEQ ID NOS: 52

<210> SEQ ID NO 1
<211> LENGTH: 1017
<212> TYPE: DNA
<213> ORGANISM: Medicago truncatula

<400> SEQUENCE: 1
atggctagta tcaaacaaat agaaatagaa aagaagaagg catgtgtgat aggtggcact      60
ggttttgtgg catcattgct gatcaagcag ttgcttgaaa agggttatgc tgttaatact     120
actgttagag acctagatag tgcaaacaaa acatctcacc tcatagcact gcaaagtttg     180
ggggaactga atctatttaa agcagaatta acaattgaag aagatttttga tgctcctata    240 tcaggatgtg aacttgtctt ccaacttgct acacctgtga actttgcttc tcaagatcct     300
gagaatgaca tgataaaacc agcaatcaaa ggtgtattga atgtgttgaa agcatgtgta     360
agagcaaaag aagtcaaaag agttatctta acatcttcag cagctgctgt gactataaac     420
gaactcgaag ggactggtca tgttatggat gaaaccaatt ggtctgatgt tgagtttttg     480
aacactgcaa agccacccac ttggggttat cctgtttcaa aagtactagc tgaaaaggct     540
gcgtggaaat ttgctgaaga aaataacatt gatctaatca ctgtgatacc tactctaaca     600
attggtcctt ctctaactca agatatccca tctagtgttg ccatgggaat gtcacttcta     660
acaggcaatg atttcctcat aaatgctttg aaaggaatgc agtttctatc gggttcaata     720
tcaattactc atgtcgagga tatttgtcgg gctcatattt ttgtggcaga gaagaatca     780 acttctggtc gatacatttg ctgtgctcac aataccagtg ttcccgagct tgcaaagttt     840
ctcagcaaac gatacccctca gtataaagtt ccaactgaat ttgatgattt ccccagcaag    900
gcaaagttga taatctcttc tggaaagctt atcaaagaag gtttcagttt caagcatagt     960
attgctgaaa cttttgacca aactgtggag tatttgaaga ctcaggggat caagtga      1017

<210> SEQ ID NO 2
<211> LENGTH: 338
<212> TYPE: PRT
<213> ORGANISM: Medicago truncatula
```

<400> SEQUENCE: 2

| Met | Ala | Ser | Ile | Lys | Gln | Ile | Glu | Ile | Glu | Lys | Lys | Ala | Cys | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ile | Gly | Gly | Thr | Gly | Phe | Val | Ala | Ser | Leu | Leu | Ile | Lys | Gln | Leu | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Glu | Lys | Gly | Tyr | Ala | Val | Asn | Thr | Thr | Val | Arg | Asp | Leu | Asp | Ser | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asn | Lys | Thr | Ser | His | Leu | Ile | Ala | Leu | Gln | Ser | Leu | Gly | Glu | Leu | Asn |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Leu | Phe | Lys | Ala | Glu | Leu | Thr | Ile | Glu | Glu | Asp | Phe | Asp | Ala | Pro | Ile |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ser | Gly | Cys | Glu | Leu | Val | Phe | Gln | Leu | Ala | Thr | Pro | Val | Asn | Phe | Ala |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ser | Gln | Asp | Pro | Glu | Asn | Asp | Met | Ile | Lys | Pro | Ala | Ile | Lys | Gly | Val |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | Asn | Val | Leu | Lys | Ala | Cys | Val | Arg | Ala | Lys | Glu | Val | Lys | Arg | Val |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Ile | Leu | Thr | Ser | Ser | Ala | Ala | Ala | Val | Thr | Ile | Asn | Glu | Leu | Glu | Gly |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Thr | Gly | His | Val | Met | Asp | Glu | Thr | Asn | Trp | Ser | Asp | Val | Glu | Phe | Leu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Asn | Thr | Ala | Lys | Pro | Pro | Thr | Trp | Gly | Tyr | Pro | Val | Ser | Lys | Val | Leu |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ala | Glu | Lys | Ala | Ala | Trp | Lys | Phe | Ala | Glu | Glu | Asn | Asn | Ile | Asp | Leu |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Ile | Thr | Val | Ile | Pro | Thr | Leu | Thr | Ile | Gly | Pro | Ser | Leu | Thr | Gln | Asp |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Ile | Pro | Ser | Ser | Val | Ala | Met | Gly | Met | Ser | Leu | Leu | Thr | Gly | Asn | Asp |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Phe | Leu | Ile | Asn | Ala | Leu | Lys | Gly | Met | Gln | Phe | Leu | Ser | Gly | Ser | Ile |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ser | Ile | Thr | His | Val | Glu | Asp | Ile | Cys | Arg | Ala | His | Ile | Phe | Val | Ala |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Glu | Lys | Glu | Ser | Thr | Ser | Gly | Arg | Tyr | Ile | Cys | Cys | Ala | His | Asn | Thr |
|-----|-----|-----|-----|-----|-----|-----|-----|-----|-----|-----|-----|-----|-----|-----|-----|
|     |     |     |     | 260 |     |     |     |     | 265 |     |     |     |     | 270 |     |

| Ser | Val | Pro | Glu | Leu | Ala | Lys | Phe | Leu | Ser | Lys | Arg | Tyr | Pro | Gln | Tyr |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Lys | Val | Pro | Thr | Glu | Phe | Asp | Asp | Phe | Pro | Ser | Lys | Ala | Lys | Leu | Ile |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Ile | Ser | Ser | Gly | Lys | Leu | Ile | Lys | Glu | Gly | Phe | Ser | Phe | Lys | His | Ser |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Ile | Ala | Glu | Thr | Phe | Asp | Gln | Thr | Val | Glu | Tyr | Leu | Lys | Thr | Gln | Gly |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Ile | Lys |
|-----|-----|

<210> SEQ ID NO 3
<211> LENGTH: 1213
<212> TYPE: DNA
<213> ORGANISM: Arabidopsis thaliana

<400> SEQUENCE: 3

| caataacaac taatctcta tctctgtaat ttcaaaagta caatcatgga ccagactctt | 60 |
| acacacaccg gatcgaagaa ggcttgtgtc attggtggca cgggaaactt agcctctatt | 120 |

-continued

```
ctcatcaagc atttgcttca aagtggctac aaagttaaca ctacagttag agatccagaa      180
aacgagaaga aaatagctca ccttaggcaa cttcaagaac ttggcgacct gaagatcttc      240
aaggcagatt tgactgatga agacagtttc gaatcctcat tctccggctg tgaatacatc      300
ttccatgtcg caactccgat caactttaaa tccgaagatc ccgagaaaga catgatcaag      360
ccggcgatac aaggagtgat caatgtgttg aaatcttgct taaaatcgaa atcagtcaag      420
cgtgtgatct acacatcttc agctgctgct gtttccatca caatctttc tggaaccgga      480 ctcgtgatga acgaagaaaa ctggactgac attgattttc tcacagagga gaagcctttt      540
aactggggtt acccaatctc gaaggtgcta gcagaaaaga agcttggga atttgcagaa      600 gagaataaga tcaatctcgt aaccgtgatt ccggcactta tagccggaaa ctctctcctc      660
tccgatcctc cgagcagttt atctctctcg atgtctttca tcaccgggaa agaaatgcat      720
gtgacgggtc tcaaggaaat gcagaagcta tctggctcga tctcgttcgt gcacgtagac      780
gatttagctc gtgcccattt gtttcttgcg gagaaagaaa ctgcttctgg tcgctacatt      840
tgctgtgctt acaacacaag tgttccagag attgcggatt ttctcataca gagatatcct      900
aagtacaatg tgttgtccga attcgaagag ggcttgtcga ttccgaaatt aacactatct      960
tcgcaaaaac ttatcaatga aggctttcga ttcgaatatg ggatcaatga gatgtatgat      1020
cagatgatag agtacttcga gtcaaaagga ttgatcaaag ctaaagaatc ttgattttt      1080 ataatgtcaa aatggattct aatagtatat gagtctttgg tctcattctc gttctataaa      1140
atggtattgt ataatattta ttatatattg gttgagttaa tgtctttga tacataaata      1200 ttacatactc tcc                                                        1213
```

<210> SEQ ID NO 4
<211> LENGTH: 342
<212> TYPE: PRT
<213> ORGANISM: Arabidopsis thaliana

<400> SEQUENCE: 4

```
Met Asp Gln Thr Leu Thr His Thr Gly Ser Lys Lys Ala Cys Val Ile
  1               5                  10                  15

Gly Gly Thr Gly Asn Leu Ala Ser Ile Leu Ile Lys His Leu Leu Gln
             20                  25                  30

Ser Gly Tyr Lys Val Asn Thr Thr Val Arg Asp Pro Glu Asn Glu Lys
         35                  40                  45

Lys Ile Ala His Leu Arg Gln Leu Gln Glu Leu Gly Asp Leu Lys Ile
     50                  55                  60

Phe Lys Ala Asp Leu Thr Asp Glu Asp Ser Phe Glu Ser Ser Phe Ser
 65                  70                  75                  80

Gly Cys Glu Tyr Ile Phe His Val Ala Thr Pro Ile Asn Phe Lys Ser
                 85                  90                  95

Glu Asp Pro Glu Lys Asp Met Ile Lys Pro Ala Ile Gln Gly Val Ile
            100                 105                 110

Asn Val Leu Lys Ser Cys Leu Lys Ser Lys Ser Val Lys Arg Val Ile
        115                 120                 125

Tyr Thr Ser Ser Ala Ala Ala Val Ser Ile Asn Asn Leu Ser Gly Thr
    130                 135                 140

Gly Leu Val Met Asn Glu Glu Asn Trp Thr Asp Ile Asp Phe Leu Thr
145                 150                 155                 160

Glu Glu Lys Pro Phe Asn Trp Gly Tyr Pro Ile Ser Lys Val Leu Ala
                165                 170                 175
```

```
Glu Lys Lys Ala Trp Glu Phe Ala Glu Glu Asn Lys Ile Asn Leu Val
            180                 185                 190
Thr Val Ile Pro Ala Leu Ile Ala Gly Asn Ser Leu Leu Ser Asp Pro
        195                 200                 205
Pro Ser Ser Leu Ser Leu Ser Met Ser Phe Ile Thr Gly Lys Glu Met
    210                 215                 220
His Val Thr Gly Leu Lys Glu Met Gln Lys Leu Ser Gly Ser Ile Ser
225                 230                 235                 240
Phe Val His Val Asp Asp Leu Ala Arg Ala His Leu Phe Leu Ala Glu
                245                 250                 255
Lys Glu Thr Ala Ser Gly Arg Tyr Ile Cys Cys Ala Tyr Asn Thr Ser
            260                 265                 270
Val Pro Glu Ile Ala Asp Phe Leu Ile Gln Arg Tyr Pro Lys Tyr Asn
        275                 280                 285
Val Leu Ser Glu Phe Glu Glu Gly Leu Ser Ile Pro Lys Leu Thr Leu
    290                 295                 300
Ser Ser Gln Lys Leu Ile Asn Glu Gly Phe Arg Phe Glu Tyr Gly Ile
305                 310                 315                 320
Asn Glu Met Tyr Asp Gln Met Ile Glu Tyr Phe Glu Ser Lys Gly Leu
                325                 330                 335
Ile Lys Ala Lys Glu Ser
            340

<210> SEQ ID NO 5
<211> LENGTH: 1331
<212> TYPE: DNA
<213> ORGANISM: Medicago truncatula

<400> SEQUENCE: 5
gccaaccaaa atcactagag aaaaaaaaat cagggaaaaa acagagaaaa taaaatatgg      60
gttctatggc cgaaactgtt tgtgtcacag gggcttcagg ttttatcggg tcatggcttg     120
tcatgagact tatggagcgc ggttacatgg ttcgagcaac agtccgcgac ccagaaaact     180
tgaagaaggt gagtcatttg ttagaactgc aggtgcaaa gggcaaactg tccctatgga     240
aggctgacct tggtgaagag ggtagttttg atgaagctat taagggtgt acaggagttt     300
ttcatgttgc tactcctatg gattttgagt ccaaggaccc tgagaatgaa atgatcaagc     360
ctaccataaa aggggtgcta gacatcatga agcatgcct caaggccaaa actgtccgta     420
gatttatttt cacatcatcg gccggaaccc taaacgttac tgaagatcaa aagcccttgt     480
gggatgaaag ctgttggagt gatgttgagt tttgtaggag agtgaagatg actggctgga     540
tgtatttgt ttcaaagaca cttgcggagc aagaagcatg gaaatttgcc aaagagcaca     600
acatggattt catcacaatc atcccacctc ttgttgttgg tccttttctt attcctacca     660
tgccacctag cctaatcact gcccttcctc tatcactgg aaatgaagct cattattcga     720
ttataaagca aggccaattc gtccacttgg atgatctttg tgaagctcac atattcttgt     780
ttgagcatat ggaagtagaa gggaggtatc tatgtagtgc atgtgaagct aatattcatg     840
acattgcaaa attaattaat acaaaatatc cagagtacaa tatccccaca aagttcaata     900
atattccaga tgaattggag cttgtgagat ttcatcaaaa gaagatcaaa gacttgggat     960
tcgagtttaa atacagcttg gaggatatgt acactgaagc aattgataca tgcatagaaa    1020
aagggcttct tcctaaattt gttaaaagca ccaataagta atggtgtcac acataaataa    1080
ataagtatag gctatgtgtc tttatgtgtg tttctgtgat ggcttaggga tcttacttaa    1140
```

-continued

```
ttccttgaga ttttctttag tagctggaat gtttgtgcaa tcctgttgaa gcccaaactt    1200
acttgaatgt tttctatctc tttcatttgt tccttattga gagctacacg aaaaaggaaa    1260
agataatgaa ttattgaata ttatttattt gcaaatgtt gaaagcttaa aaaaaaaaaa    1320
aaaaaaaaaa a                                                         1331

<210> SEQ ID NO 6
<211> LENGTH: 1248
<212> TYPE: DNA
<213> ORGANISM: Medicago truncatula

<400> SEQUENCE: 6
gcgcccatgg gttcagtctc agaaacagtt tgcgtcacag gggcttcagg tttcatcggg     60
tcgtggcttg ttatgagact tatggagcgc ggctacacag ttcgagccac cgtgcgcgac    120
ccagataaca tgaagaaggt gaagcatttg ttggaactgc caggtgcaaa tagcaaacta    180
tctctttgga aggctgacct tggggaagag ggtagttttg atgaagctat taaagggtgt    240
acaggagttt tcatgttgc tactcctatg gattttgagt ccaaggaccc cgagaaggaa    300
gtgataaacc ctacaataaa tggattacta gacataatga aagcatgtaa gaaggcaaaa    360
acagttagaa gattggtttt cacatcatca gctggaactt tggatgttac tgagcaacaa    420
aattctgtaa ttgatgaaac ttgctggagt gacgtcgaat tctgccgtag agtcaagatg    480
actggttgga tgtattttgt ttcaaaaacc ctggcagaac aagaagcatg gaagttttcc    540
aaagaacaca acatagactt tgtttccatt attccacctc ttgttgttgg tccatttatt    600
atgccttcaa tgccaccgag tctaatcact gctctttccc ttatcacagg atatgaggct    660
cattactcga tcataaagca aggccaatac atccacttag acgacctttg tcttgctcat    720
atatttctgt ttgagaaccc taaagcacat gggagataca tatgttgttc acatgaggca    780
accattcatg aagttgcaaa acttattaac aaaaaatacc ctgagttcaa tgtccctaca    840
aaattcaagg atatcccaga tgatctggaa attatcaaat tttcttcaaa gaagatcaca    900 gacttgggt ttatatttaa atacagctta gaagacatgt tcacaggagc tatagaaacc    960
tgcagagaaa aagggctact tcctaaagtt acagagactc cggttaatga taccatgaag   1020
aaataaatat gcttttgtgt ctttgatgga ttgtgtctct ttttccttttt tcatttgtgt   1080 ttttttttt aaggatcctt tttcatatgt tattaactaa ggtttatgtt atatgatgtc   1140
actcataata atattcatgt ttatgggtca cgttgtctgt taattatata agaactataa   1200
tgatatatgc tatattgctt ctaaatttac aaaaaaaaaa aaaaaaa                 1248

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gggcccatgg accagactct tacacac                                         27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer
```

-continued

```
<400> SEQUENCE: 8
cccagatcta gaatgagacc aaagact                                           27

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gatatggaaa agatctggca tcac                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
tcatactcgg ccttggagat ccac                                              24

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ggatccatgg agggttcgtc caaagggctg cg                                     32

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
tctagactcg agatcaaatt tcacagtctc tcc                                    33

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
cctcatagca ctgcaaagtt tggggg                                            26

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer
```

<400> SEQUENCE: 14
gcctgttaga agtgacattc cc                                                  22

<210> SEQ ID NO 15
<211> LENGTH: 7918
<212> TYPE: DNA
<213> ORGANISM: Arabidopsis thaliana

<400> SEQUENCE: 15

| | | | | | |
|---|---|---|---|---|---|
| ggtaccttag | attatccaaa | tttgtagctg | caaaagttgt | tcctgtgttc | aagaaagaaa | 60 |
| gacctgtaaa | atgatctgga | tgtgtttggt | tatatatata | agaagactta | aaagataatg | 120 |
| acttaatctc | gtaacgagtc | acacggacgt | gacgctgaaa | ctcacacacg | ttggtgccac | 180 |
| gtctttgtct | ttcctctttt | gctctacttt | tttctcctca | taggtgatag | gtcccataag | 240 |
| caatgaaata | aaaaaaatgg | taattgactt | ttctccaaac | attttcgaat | ctgattttct | 300 |
| ttttcaaggt | tttataacct | ctacattcca | gaatatgact | aatgacatca | ttatccaatt | 360 |
| atttttata | ctgtaaactc | attattatga | atattcttta | tttcaaaaaa | ttaccattga | 420 |
| tttataagtt | tattagtata | atatataaca | tatggaataa | aacttttatt | taaaaaaaaa | 480 |
| tattttccc | caaaaaaagt | aggattaata | acctgattaa | taaataaaaa | gtgttatatt | 540 |
| tttaagcatt | gtatgcattt | actttatcat | agttgtcttg | tttttaagag | ttaaaaaata | 600 |
| atgatgaaca | atttcacgga | caacgattcc | acgataaagc | tttccctgca | acactcagat | 660 |
| tttctaaaga | cggttttgca | ttgcgttttc | tgggattcga | aacccaaaca | tgatgtacaa | 720 |
| gtattaatga | actcttagtt | aaccattaga | ttaaaaatat | tttcactatt | aattttctct | 780 |
| taaaaatatt | aataattttt | tgaaatcaaa | aattatagtt | attttatttt | aataaacgag | 840 |
| aaacactaca | aaaaagtta | actgcattta | gataatttaa | taaactaaaa | tatccacata | 900 |
| aaaatttcaa | atttatcaaa | aataaaacat | caatttgttt | tttgtttaa | attaaagatt | 960 |
| tgctattgat | tgcataagga | agaaaacttt | acaaagccga | aaggcctaag | agcccaacac | 1020 |
| acacaaaaga | agaaccattt | tggatcaagg | gaaccgacca | tgggtattag | aagtagtggt | 1080 |
| ataaagccca | tcatatccca | acacataacc | cacgaatgtt | taatattaaa | agtttgttgt | 1140 |
| tcggctcatg | attagcgatg | atcatacaga | aagtttgtat | ctaatacgtg | ccttgaattt | 1200 |
| tatgtgtaca | acaaacaaat | taaattattc | aaaaccataa | attataaaaa | ataattacag | 1260 |
| aaataaaact | atattaagag | cgagcctacc | atccggtgtg | caactttcta | gtttatatac | 1320 |
| agtggcggat | caacgttaat | gaggcaaatt | ggttcaaatt | catctaaata | agactagagt | 1380 |
| tcacaggttc | gattcctcct | tataacaatt | tgctcccacc | aatttttttt | gctgggtccg | 1440 |
| cccctggtta | tatatatact | tctacaccag | gtttgggttc | gagtccacac | ataattaacg | 1500 |
| acacaattat | agtgcacgat | agaatgaact | aaaacagcta | gagcgtagag | ggctcattgt | 1560 |
| ctataaaaat | ccttcgttaa | cttgcaagaa | accaagagta | gagggctcac | acttaagtct | 1620 |
| cctacatgac | gattatattt | cgtcaaaaag | aagcaattag | ttagctttac | agcatatcat | 1680 |
| ttcgcctagg | ttttccatcg | tacacgtaaa | ttttcatgca | agaaagcaga | aatatacaaa | 1740 |
| tactaacttt | tagatactga | aaatgagat | cagattctag | tcaaattttg | ttaaaagtat | 1800 |
| ttataaattt | aaattgcaag | tcctcaaaaa | gtacgactaa | aaatgctttt | cttagaaaat | 1860 |
| gataataaac | cggcgtttta | tatataagtg | tttcttttc | tcttctgtcc | agaagtaaat | 1920 |
| cattaagaac | caatatggct | tttcttaaac | taatctccgt | gataatcaaa | tctttgatca | 1980 |
| ttctccacac | aatcccatca | acaacatcga | tctcactaga | tgcaccaaca | atgattctaa | 2040 |

```
tcggcactac taactataga gatagttgtc ccaaaaaaaa aaaaaaaaac taactagaga    2100
gataaatcat attcaataca tgtactattt ctactatact taagaaaatt tgtataccac    2160
tatcttaact cttaacactg aacatactat acactatctt aactcccaac tcttgtaaaa    2220
gaatatctaa ttttaagaaa agacttcaaa tgcttgttaa atttctagtg aagatgcaca    2280
ttctaaaaac tggtaaaatg gtaagaaaaa aatatataaa aaaatagcct tattaaaatt    2340
tatatctcct atttctctat ccaaactaca cggatgaagc ttattgttat tcatccaccc    2400
ttttctcaa ttctgtccta tttcttgtgc atgaaacttc tccatcttgt aatcggataa     2460
atcatacccca aattttttct ttctgaaaac atatataccc gaacattaat tactatcgtc   2520
ctttctccta atttttgttaa gaaacatgtt tgtttgtttt tagtactgaa aaaggatgga   2580
gatacttgct agatcctatg aaccttttct ctctaggaca aatcagtaac caaacaataa    2640
cttagcaaat taagcacgac agctaataca taaaatgtgg atatcaaaca tgcacgtcac    2700
ttccttttt ccgtcacgtg tttttataaa ttttctcaca tactcacact ctctataaga     2760
cctccaatca tttgtgaaac catactatat ataccctctt ccttgaccaa tttacttata    2820
cctttacaa tttgtttata tattttacgt atctatcttt gttccatgga gggttcgtcc     2880
aaagggctgc gaaaaggtgc ttggactact gaagaagata gtctcttgag acagtgcatt    2940
aataagtatg gagaaggcaa atggcaccaa gttcctgtaa gagctggtat gttatttacg    3000
aacacacaca cactaaccga cacacacaca cacaaatatg aatatctata atcactacca    3060
atagtcttcg ttctctctat tttctattca gaaaattgat taatacccgg tattaaaaaa    3120
aaaaaaaaaa atttgtttaa atgagtacaa atcattgtta caacttcttt atgctgtttt    3180
tacatgctat taaggttgt gcatgaaaat ttcttttgct gttcgtattt gttttacacc     3240
taaacgaaga ttttttactta aaattaaaga aaaaaaatta tactaatttt agttacgttg   3300
cgtattgcta gcttctccta taagtcgtt caaatttta cacgcttgtc ttcttgtaaa      3360
tgaattcgtg ggaaaatttt tgtatgaacac gtgtttctgt gttggaacag ttctttattt   3420
ttattggtgt gcatagattc ttcctgataa aatatataga aggagacaaa taaaaaacag    3480
tcttagtatg taggtataat caaagaatca attattggtt ttgtagggct aaaccggtgc    3540
aggaaaagtt gtagattaag atggttgaac tatttgaagc caagtatcaa gagaggaaaa    3600
cttagctctg atgaagtcga tcttcttctt cgccttcata ggcttctagg gaataggtat    3660
taattgttac ctcgatacta cttaactcgg agagtcgtca taagttaata ctaataacat    3720
atgtatattt tcttacaatt gttaggtggt ctttaattgc tggaagatta cctggtcgga    3780
ccgcaaatga cgtcaagaat tactggaaca ctcatctgag taagaaacat gaaccgtgtt    3840
gtaagataaa gatgaaaaag agagacatta cgcccattcc tacaacaccg gcactaaaaa    3900
acaatgttta taagcctcga cctcgatcct tcacagttaa caacgactgc aaccatctca    3960
atgccccacc aaaagttgac gttaatcctc catgccttgg acttaacatc aataatgttt    4020
gtgacaatag tatcatatac aacaaagata agaagaaaga ccaactagtg ataatttga    4080
ttgatggaga taatatgtgg ttagagaaat tcctagagga aagccaagag gtagatattt    4140
tggttcctga agcgacgaca acagaaaagg gggacacctt ggcttttgac gttgatcaac    4200
tttggagtct tttcgatgga gagactgtga aatttgatta gtgtttcgaa catttgtttg    4260
cgtttgtgta taggttttgct ttcacctttt aatttgtgtg ttttgataaa taagctaata   4320
gttttttagca ttttaatgaa atatttcaag tttccgtgtt tacattttga agaaaataaa   4380
```

```
atattaatat attctgaaga tttttgtttt tttttggtta tctacatgac aacagtaaaa    4440
atagaaaaaa aatcttattt tttgaaaaag gtatgtatcc ggtgtttaga atactttccg    4500
aaatcaaacc gcctatattt ctaatcacta tgtaaaattg taaaccaatt gggttaaaac    4560
tcaactaaca aactttctaa ataaatgtca tttttgtttt caaatatgat tgaactcgga    4620
tttaggagtt ttaccttca gtaccaaacc ttctctaccg accatgtatg gttgggcaaa     4680
tgtcatgttt tacaatgttt agattactaa acactttggt tgagaaggca atgctttatt    4740
tatatattct gaagtcatgt tttagtgtta tttttattta tttttaaatg catagattgt    4800
taacgtgcag attctcatat gggcttagtt tctggatttt gattatcaaa accgtattcc    4860
actcttaaat gattacgaca aaaaaatcaa tactactaac aaacctattt cccagttatt    4920
aattagtcaa taacaattgt caaatttaat aacgtacttg ctagtaataa agttttaacg    4980
acgatcatag ataggttttt gaaacccata ctcgcagaag ttctgataca aaaatttgta    5040
ctccctctat ttcaaaatat taaatgtttt agataaaagc acaatgttta agaaactaat    5100
taatcttgag tttcttacat tataaacata aattaatatc tattaaaaat aatttgacca    5160
atgatataac ttcagcata atataaatag ttaaaaaaaa actgtttact ttaataattt     5220
gcataacaac tagctagtct ggtccaagaa cggtagtagg atgagatttt agaaggtcgt    5280
aatgtgtaag actaataatc atgcgataga cgatcatgca tgaattattt tatgtaatac    5340
ttatatggtt ccaaaatcta taagaaccct caattataaa agtaatatct attaaatatt    5400
taaacgataa tttcatacgg aaaattaata gataaattct tctatttgtt tttaaatata    5460
tgtaaatgcg aaagtgtccc atgcaatttt atatatttaa tcaagtgaaa actcgaaaac    5520
aaaaaacttg atgtacttca aacaagtttt tttggcaagt aatacccatt ctgttccggt    5580
tggactataa atgcatggaa aagcaccaaa aaaggcatgg atactttcgc gattttgcc     5640 attttgtat ctttgttcat cgctccgttc aaaagaacct cttgtcgtta ctataataag     5700
ttatggacca acggtattgt catgtatcaa ataactatg tagcatacgt gtattgtgaa     5760
tcaatgaagc aatagagaga taacactactg aaacgtccac atctcgttta taaaaaaatc   5820
gtctacatgc ttctctttgg ctggacatcc caacttttct caccgtaacc agtgaaattg    5880
tattatttgg taagaattac ggatggagtt agatttattt tgttgtgtgt gtataaatca    5940
atacttatac agtttttacg tgtataacgg cacgcctcat gggttttgct aataaggtcc    6000
aagtagtgga cagaaaagaa cttgtgattg aatagtgttt tgtattgaaa ggttaaaacg    6060
tgtttccaaa tggattcaac caaattccaa catgttcagt gtcgtacatg cgaaaacatt    6120
atcgagtaaa ataagttcca ttatactttg attttgtatt gattccatag agtagaaatg    6180
tgtgctttag cttatagtta aacactatct tcaaaggggt aatgctggat tcgaagtatt    6240
taattagtcc tgttcgaccg aatcaaagtt caatcgattt tgaaaaacaa tcatttcggg    6300
tatagcttga aacatcccaa accacaagtt ccaaaagcac acatattatc accattcaac    6360
taaccattcg ggtttgataa ccggtagttg gatgttcaaa gatctcatca gatttggtgt    6420
caagaggata attgtgattg agttgtgaac ccttgtgatg gagatagttt ccttgtttgg    6480
atgttaagtt gaattttggg atcatccttg tttcaaaaag actggaaaac acacaaaaaa    6540
aaaaaaaaaa aaacttgcaa ataaatttaa ttttagaaa ttttatattg tagtgaaaaa     6600
tgtttgcaaa tttagctgg agatgttttt ccatttggaa ttttttttct taattttgcc     6660
ttttatttta cattgtatat tgctagcttc ttccttgacaa gaaagaacga tgtcaacctc   6720
tgatttgtct tcttataaat gaatttgttg aaaattgctg tacgagcaag tgttttttgtg   6780
```

-continued

```
ttggaacatg tctctatttc tattggtgtg catagattct tcatgataaa atatataagg    6840
agacaaataa gaaagcagtc ttattaggta ggattgccta aaatattcgt tagattcgct    6900
tggatctatt attcggttaa attgattcga aaaatctgaa tatccataat tttacgaagc    6960
aaatcaaata ttaaaaattg atattcgtta aaaacagaaa aataacaaa tattaaattt     7020 aaataggcgg atatcctctc taattcggta tacatgaata tatgtatatg tatatagata    7080
agtataaata tatatattaa taatcttact cttttatat gtaagtttta gaagtttatg     7140
ttcatcaaat tagttattta actattagtt taaaaaattg aaaagagata ttttttccaa    7200
tgaagtttta cttatttggg attaaatttc taatttttat gtttttaatt tttataattg    7260 ttttgagat atacttaaca aatcgaatat ctagcaaata actcggattt taacggaata    7320
tctggacagc cggatattcg gttactttcg aaacaaatac gaatcagaaa actaattatt    7380
ccgatatagc aaatcggatc acaaatacta ccaaaatcca tgatatatgt gtcgtgtcca    7440 ccctattag taggtataat taattgtaat tagtggtttt gtaagactaa atcagcccag     7500
gaagagttgt agactaagat gcttatacta tttgaagcca agtatcaaga gaggaagatt    7560
taggctctga tgaagttgat cttcttcttc gccttcccaa ccttctagga aatagtattt    7620
gttatacttt atactaatta attcttcgg gattcataag attattaata acatattatt     7680
cgtataatgt ttaacaactt ttagattggc tttgattgct ggtctattgg ctggtcagac    7740
cacaaacggt gtcaaaaatt acttgaacac tcaactgagt aagaaacatg aaccatgttg    7800
taagatttag ataaaaaaaa aaaaaaagca ttacttccaa tgctaccata ctgggctaaa    7860
aatggatgtt tttaatctcg accttaatcc ttctcatttta acagcagtgg cctaccaa    7918
```

<210> SEQ ID NO 16
<211> LENGTH: 248
<212> TYPE: PRT
<213> ORGANISM: Arabidopsis thaliana

<400> SEQUENCE: 16

```
Met Glu Gly Ser Ser Lys Gly Leu Arg Lys Gly Ala Trp Thr Thr Glu
 1               5                  10                  15

Glu Asp Ser Leu Leu Arg Gln Cys Ile Asn Lys Tyr Gly Glu Gly Lys
                20                  25                  30

Trp His Gln Val Pro Val Arg Ala Gly Leu Asn Arg Cys Arg Lys Ser
            35                  40                  45

Cys Arg Leu Arg Trp Leu Asn Tyr Leu Lys Pro Ser Ile Lys Arg Gly
        50                  55                  60

Lys Leu Ser Ser Asp Glu Val Asp Leu Leu Arg Leu His Arg Leu
 65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175
```

```
Asp Asn Ser Ile Ile Tyr Asn Lys Asp Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245

<210> SEQ ID NO 17
<211> LENGTH: 1851
<212> TYPE: DNA
<213> ORGANISM: Arabidopsis thaliana

<400> SEQUENCE: 17
```

| | | | | | |
|---|---|---|---|---|---|
| attttagag agagagctac cacgttttcg tatctccggg aacgatggat gaatcaagta | | | | | 60 |
| ttattccggc agagaaagtg gccggagctg agaaaaaaga gcttcaaggg ctgcttaaga | | | | | 120 |
| cggcggttca atctgtggac tggacttata gtgtcttctg gcaattttgt cctcaacaac | | | | | 180 |
| gggtcttggt gtgggggaat ggatactaca acggtgcaat aaagacgagg aagacaactc | | | | | 240 |
| aaccagcgga ggtgacggcg aagaggctgc gttagagag gagccaacag ctcagggagc | | | | | 300 |
| tttatgagac acttttagcc ggagagtcaa cgtcagaagc aagagcatgc accgcattgt | | | | | 360 |
| caccggagga tttgacggag acagaatggt tttatctaat gtgtgtgtct ttctcttttc | | | | | 420 |
| ctcctccatc tgggatgcca ggaaaagcgt atgcaaggag gaagcacgta tggctaagtg | | | | | 480 |
| gtgcaaatga agttgacagt aaaactttt ctagagctat tctcgctaag agtgctaaaa | | | | | 540 |
| ttcagacagt ggtttgcatt ccaatgcttg atggtgttgt ggaactaggc acaacgaaaa | | | | | 600 |
| aggtaagaga agatgtagag tttgttgagc tcacaaagag tttcttctat gaccactgca | | | | | 660 |
| agacgaaccc aaagccggct ctttctgaac actccaccta cgaagtgcat gaagaagccg | | | | | 720 |
| aagacgaaga agaagtagaa gaagagatga caatgtcaga ggaaatgagg cttggctctc | | | | | 780 |
| ctgatgatga agatgttccc aatcaaaatc tacactctga tcttcatatt gaatcaaccc | | | | | 840 |
| atacgttaga cacacatatg gacatgatga atctaatgga ggaaggtgga aactattctc | | | | | 900 |
| agacagtaac aacacttctc atgtcacacc ccacaagtct tctttcagat tcagtttcca | | | | | 960 |
| catattctta catccaatca tcgtttgcca cgtggagggt tgagaatggc aaagagcatc | | | | | 1020 |
| agcaagtgaa aacggcgccg tcgtcacaat gggtgctcaa acaaatgatc ttcagagttc | | | | | 1080 |
| ctttcctcca tgacaacact aaagataaga ggctaccgcg ggaagatctg agccacgtag | | | | | 1140 |
| tagcagagcg acgcaggagg gagaagctga cgagaaatt cataacgttg agatcaatgg | | | | | 1200 |
| ttccatttgt gaccaagatg gataaagtct caatccttgg agacaccatt gcgtacgtaa | | | | | 1260 |
| atcatcttcg aaagagggtc catgagcttg agaatactca tcatgagcaa cagcataagc | | | | | 1320 |
| ggacgcgtac ttgtaagaga aaacatcgg aggaggtgga ggtttccatc atagagaatg | | | | | 1380 |
| atgttttgtt agagatgaga tgtgagtacc gagatggttt gttgcttgac attcttcagg | | | | | 1440 |
| ttcttcatga gcttggtata gagactacgg cagttcatac ctcggtgaac gaccatgatt | | | | | 1500 |
| tcgaggcgga gataagggcg aaagtaagag ggaagaaagc aagcatcgct gaggtcaaaa | | | | | 1560 |
| gagccatcca ccaagtcata atacatgata ctaatctata gaccctaact ttattgatgc | | | | | 1620 |
| caactctaga gaaggataat taagcgtatt tttgttttag cctcacatgt attaagacat | | | | | 1680 |

```
cagttacata tatagccgga tgcaacatat aaatgaaaat gtactagatg atattgttca    1740
tttgtccaat gtagtacttg tgtatgatgc aattgcaaca tataaatgca aatgtactag    1800
atgacgatgt tgttcgttgt ccaatttagt actaaaaaaa aaaaaaaaaa a             1851
```

<210> SEQ ID NO 18
<211> LENGTH: 518
<212> TYPE: PRT
<213> ORGANISM: Arabidopsis thaliana

<400> SEQUENCE: 18

```
Met Asp Glu Ser Ser Ile Ile Pro Ala Glu Lys Val Ala Gly Ala Glu
  1               5                  10                  15

Lys Lys Glu Leu Gln Gly Leu Leu Lys Thr Ala Val Gln Ser Val Asp
             20                  25                  30

Trp Thr Tyr Ser Val Phe Trp Gln Phe Cys Pro Gln Gln Arg Val Leu
         35                  40                  45

Val Trp Gly Asn Gly Tyr Tyr Asn Gly Ala Ile Lys Thr Arg Lys Thr
     50                  55                  60

Thr Gln Pro Ala Glu Val Thr Ala Glu Ala Ala Leu Glu Arg Ser
 65                  70                  75                  80

Gln Gln Leu Arg Glu Leu Tyr Glu Thr Leu Leu Ala Gly Glu Ser Thr
                 85                  90                  95

Ser Glu Ala Arg Ala Cys Thr Ala Leu Ser Pro Glu Asp Leu Thr Glu
            100                 105                 110

Thr Glu Trp Phe Tyr Leu Met Cys Val Ser Phe Ser Phe Pro Pro Pro
        115                 120                 125

Ser Gly Met Pro Gly Lys Ala Tyr Ala Arg Arg Lys His Val Trp Leu
    130                 135                 140

Ser Gly Ala Asn Glu Val Asp Ser Lys Thr Phe Ser Arg Ala Ile Leu
145                 150                 155                 160

Ala Lys Ser Ala Lys Ile Gln Thr Val Val Cys Ile Pro Met Leu Asp
                165                 170                 175

Gly Val Val Glu Leu Gly Thr Thr Lys Lys Val Arg Glu Asp Val Glu
            180                 185                 190

Phe Val Glu Leu Thr Lys Ser Phe Phe Tyr Asp His Cys Lys Thr Asn
        195                 200                 205

Pro Lys Pro Ala Leu Ser Glu His Ser Thr Tyr Glu Val His Glu Glu
    210                 215                 220

Ala Glu Asp Glu Glu Glu Val Glu Glu Glu Met Thr Met Ser Glu Glu
225                 230                 235                 240

Met Arg Leu Gly Ser Pro Asp Asp Glu Asp Val Ser Asn Gln Asn Leu
                245                 250                 255

His Ser Asp Leu His Ile Glu Ser Thr His Thr Leu Asp Thr His Met
            260                 265                 270

Asp Met Met Asn Leu Met Glu Glu Gly Gly Asn Tyr Ser Gln Thr Val
        275                 280                 285

Thr Thr Leu Leu Met Ser His Pro Thr Ser Leu Leu Ser Asp Ser Val
    290                 295                 300

Ser Thr Tyr Ser Tyr Ile Gln Ser Ser Phe Ala Thr Trp Arg Val Glu
305                 310                 315                 320

Asn Gly Lys Glu His Gln Gln Val Lys Thr Ala Pro Ser Ser Gln Trp
                325                 330                 335

Val Leu Lys Gln Met Ile Phe Arg Val Pro Phe Leu His Asp Asn Thr
```

```
                340             345             350
Lys Asp Lys Arg Leu Pro Arg Glu Asp Leu Ser His Val Ala Glu
            355                 360                 365

Arg Arg Arg Arg Glu Lys Leu Asn Glu Lys Phe Ile Thr Leu Arg Ser
370                 375                 380

Met Val Pro Phe Val Thr Lys Met Asp Lys Val Ser Ile Leu Gly Asp
385                 390                 395                 400

Thr Ile Ala Tyr Val Asn His Leu Arg Lys Arg Val His Glu Leu Glu
                405                 410                 415

Asn Thr His His Glu Gln Gln His Lys Arg Thr Arg Thr Cys Lys Arg
            420                 425                 430

Lys Thr Ser Glu Glu Val Glu Val Ser Ile Ile Glu Asn Asp Val Leu
            435                 440                 445

Leu Glu Met Arg Cys Glu Tyr Arg Asp Gly Leu Leu Leu Asp Ile Leu
            450                 455                 460

Gln Val Leu His Glu Leu Gly Ile Glu Thr Thr Ala Val His Thr Ser
465                 470                 475                 480

Val Asn Asp His Asp Phe Glu Ala Glu Ile Arg Ala Lys Val Arg Gly
                485                 490                 495

Lys Lys Ala Ser Ile Ala Glu Val Lys Arg Ala Ile His Gln Val Ile
            500                 505                 510

Ile His Asp Thr Asn Leu
            515

<210> SEQ ID NO 19
<211> LENGTH: 5777
<212> TYPE: DNA
<213> ORGANISM: Arabidopsis thaliana

<400> SEQUENCE: 19
gatctttttc atgttttgtt tttattcata catatccaag agactttaaa tatttgttta      60
tcaatattac aaattatcac ataatatatt cgtgttttgc ttttattcat atgattccaa     120
aaatcactta ttaaaagcta ttcattttaa acttgttcca acctaaacat ctttattttt     180
aaagtctttt cagaatatta gaccaaaaat ataaatacat tttaataata tatgaccaa      240 aattaattat ttaaaacttt tgcagatgca tcatctatat atacatttttt gcagccactt    300 tgtgaaataa atcctggagt tgggatttat ttacagcggc tgccactgga atttaataat     360 tattttgat aattagaaag aaaatcttct aattaaatat ttgacattta acaatcttcc      420
caaaatctct ctaccttaac tacacgatta attactaaaa taaaacttcc aaaatattta     480 atattttta attactacaa aattatcatt tttgatattg cttttctaca tgattataat      540
catcaaaccg tagagatctt tgatagcatt taattactac aaaattacaa atatttaga      600 caataattca taaacatatc ataaataaga tcaacattaa taaaataaat gagttttttt     660
tagaggacgg gttggcggga cgggtttggc aggacgttac ttaataacaa ttgtaaacta     720
taaaataaaa acattttata actatataca atttacaaac ttttatatat attaatttaa     780
aaaataaatt gttcccgcgg tgtaccgcgg gttaaaatct agttatattt taaaaatcga     840
gatgttacat atgtgttaaa ctttcttttt tgtcttctta tgtgatatca aattttatga     900
tcttatcgat tttaatcagg tatatcttgg tatagcctta gatttcataa tcgcatataa     960
aaatcataaa ttatgtagaa actagttata atcaaataat atttatttca tatggtatac    1020
caaaattaag tattcaattg ctacgtggat attaataatt tgaattcggt aacatactct    1080
```

-continued

```
ttttcttttt gttaaaccaa agaatctcaa acaaaagttt ttgatcatag ttactaaatc      1140 attttttggtg aataaccgag agaatgtctc ccgacttcta ttaaaaaaca aaaataacaa     1200
ttacacaatc actcgtcttg aacaaacagg tctagaaaca tcatcccgta agatttcatc     1260
cgcacaccgg agaacataaa caagagcata aaagcttaaa gacaagcata gtttgttaac     1320
atgtccgtaa aatgattagc ctctctatat gtgaaacacg gtcaatctag ttttttcgata    1380 aaaaactata gcgcaaacgt actagaaatg atagcagatg agagtcccat aactttgtct     1440
tcaaaatctc aaccaccatt taccacaaat atggggatga aaacaggcaa acggtctcat     1500
acgtcgtaaa taagcattct taatgtcaag ttggtagata ggccataaaa taagcatcct     1560
tatgtttagc gcatagcctc cacaccattc accctcctca ttacgtatca gaccaccacc     1620
agccgcgagt ctcgaattgc cataaaatac cccatcagta tttaatttaa accagcccat     1680
agacgagata agccatttta tcagcttctc aacccgacca gcccttttgtg ttgccttttcc    1740 gctactagct ctcgcctcca atacctcctt agctaactct cttatgaacc gcaccctatt     1800
cttccatact ttattctccc caaaaactag ctaattgaat taccaacatt tgatcaagat     1860
aatatactag gtagctaatt aatgagctca ttttttttttt gtcgtcaatg ggctaattta     1920
ttaattacag tatgaactat tgactattat tctaaataag tgaatatcac gagtatgtac     1980
gaattattgg atgtatctat ttgtattgat tgatgtaata tcaaatagta agaattgga     2040 gtaaacgtgg gtttgggtt gaagcaggta gggcatgtca agtagggcg tctttcgtta      2100 tgtccccttc ctctaaattt gaacctctgt cattgtttac agaaaaatcg taataaccca     2160
taaatgtgtt ttaaaaaaca ttatttcgag ttttctacac atattctagt catgtttaat     2220 ttgaatctttt tcttatttaa gtaagcttta gacattttta acctaagttt tcttctccct     2280
tcataaattt tgagatctat ataatgttct tacatttttgg atcaagatct tcatattctc     2340
attccaatta gtaaaagatt ttttcacctt ttaatctctt atctttatt tatattctttt     2400 agttatgttt atgcttttca tcatatttag tggttagttt ttattattta tttattgatt     2460
catgacttat gctagattat gataagaatt tatgttacca cttgataaat cctccatttg     2520
acatgtgttt aatgctagat ttatattgtc tccaaattta caactttgat gtcttatgat     2580
aaatgccaac aaccaaattt cagataaaga ttagcagact aactaagctt attattcact     2640
tgcaaggtgg agtgatgttg aaagaaccct cacagacacg tcatgggaa gactaaatct      2700 ctttttagca cgttacacct ttgagatcgc gtttattcca tatggagaga gagcaacaat     2760
acgagacatg gagaggcacc attaccgccg gcgcaactgc ttccaaatat tgacaaacaa     2820
atttgaatct ggatcttctc tattcgtgaa caaggagata gaagctacga tgaatgcatg     2880
gaagcttggt ttgctttaat ataaacacta aaggggagta gaactttctt gaaaaattgt     2940
atgcaaatta tttaccgaat gttaaaagct tttttcgaat aaattttaca ttttcttaat     3000
aataataata aaaaggatt gttgattatc ttaatcacaa acaatttatt ttagctgaat     3060
tagacaattg ttagtaaaat gattagagtg tcacatatta atgttgttag tgtttcatgt     3120
catcctagtg atccaataat taggccattc tatagctcgt aacgttaaaa taaaggccc      3180 attatctgaa tatacagaag cccattatca atagatacat taaaagatac tgattaatcc     3240
agagggttta tatctacgcc gtctccattg attatttctc cgtctcttga aaaatccgac     3300
tgacactgac ctcaaaactc tcctctcact ttcgtcgtga agaagccaaa tctcgaatcg     3360
aatcagcacc acacatttcc atggataatt cagctccaga ttcgttatcc agatcggaaa     3420
ccgccgtcac atacgactca ccatatccac tctacgccat ggctttctct tctctccgct     3480
```

```
catcctccgg tcacagaatc gccgtcggaa gcttcctcga agattacaac aaccgcatcg   3540
acattctctc tttcgattcc gattcaatga ccgttaagcc tctcccgaat ctctccttcg   3600
agcatcctta tcctccaaca aagctaatgt tcagtcctcc ttctctccgt cgtccttcct   3660
ccggagatct cctcgcttcc tccggcgatt tcctccgtct ttgggaaatt aacgaagatt   3720
catcaaccgt cgagccaatc tcggttctca acaacagcaa aacgagcgag ttttgtgcgc   3780
cgttgacttc cttcgattgg aacgatgtag agccgaaacg tctcggaact tgtagtattg   3840
atacgacgtg tacgatttgg gatattgaga agtctgttgt tgagactcag cttatagctc   3900
atgataaaga ggttcatgac attgcttggg gagaagctag ggttttcgca tcagtctctg   3960
ctgatggatc cgttaggatc tttgatttac gtgataagga acattctaca atcatttacg   4020
agagtcctca gcctgatacg cctttgttaa gacttgcttg gaacaaacaa gatcttagat   4080
atatggctac gattttgatg gattctaata aggttgtgat tctcgatatt cgttcgccga   4140
ctatgcctgt tgctgagctt gaaagacatc aggctagtgt gaatgctata gcttgggcgc   4200
ctcagagctg taaacatatt tgttctggtg gtgatgatac acaggctctt atttgggagc   4260
ttcctactgt tgctggaccc aatgggattg atccgatgtc ggtttattcg gctggttcgg   4320
agattaatca gttgcagtgg tcttcttcgc agcctgattg gattggtatt gcttttgcta   4380
acaaaatgca gctccttaga gtttgaggtg agagtttctc tttcgctaca taattctcat   4440
ttgctaggcc tagattctaa tgaggaagca ttgattattg gtttagattg tgttgcatta   4500
cagatagttc tctaggtttg gtaactaaac gttttttcga ttcttgataa caaagccact   4560
agagatttga cactaactcg ttttagattt acctgaatca atatctctgt taaaatcaat   4620
tactttgtta tgcatacata aatcacagtt tagtagtcat atatattggc tcttattagc   4680
gacaggtctc acacttgctg taatggctga tagtgtagta gtcatatgtt ggctttcatc   4740
taagttgatg tatcatatga tgaatagttg tacactcgtc aggttctaat ttttacccat   4800
aattcttcag tctattttt tttgagacaa tctattctta atttaacgaa gccactagct   4860
acgtatacaa atattgttaa tttaacgaag tatctgagaa ttgtttactg ctgactctgc   4920
tgtatgccct cagaaacata tagaagtgga attggaaact tcatgctggt ttgaacatct   4980
ttgtatgtgt gcttcaggtt tttgtaactc atttagacaa cagcattgca tatatacacg   5040
cacatatgca acctagaaaa tcaaataacc tttccttata attactatcc atttcacttg   5100
atgtcaggtg cagatgtgaa gtgatcaata aggattttag catagacccg tataatcgtc   5160
atgtgcgtaa gtaggtttgg tttgcgctcc ctctcgcttt taggtccgca atgactctgt   5220
atctatctga ttgtaactaa aactgaattc atttgatgaa ccaaatgata ctattatctt   5280
atgttgtgta taaaacccaa ccaggatata ttgcggtttc tggtgtttag atttggtaat   5340
tggagcttag tacaatgcaa ccctgtcttg ctttattgga cgtctctaag ataaatcagc   5400
ttgcaatgaa ttccaatgga gtttgtcagt ttgaattaac ttctttgcat aattaacaca   5460
aagatttgca gtataaattc cattggaaga cttatttgtt tatttgacac agatttaaat   5520
tgaatttcaa tggagtttca gtcgactatg tgacacaaag atttgaaatg aactccaatg   5580
ggaatttgat gagtaaatta ttataaacaa tccaatgttt gacacaaata ttttagaatc   5640
ttcacatctg aagtcttata atcgtagca aaattttcaa tcttgaaaat tataaaaaat   5700
gagaattaat ttaaatcact gatccgataa tctcctctag aaatataaga atctataaac   5760
cattaatagt agaattc                                                 5777
```

<210> SEQ ID NO 20
<211> LENGTH: 341
<212> TYPE: PRT
<213> ORGANISM: Arabidopsis thaliana

<400> SEQUENCE: 20

Met Asp Asn Ser Ala Pro Asp Ser Leu Ser Arg Ser Glu Thr Ala Val
1               5                   10                  15

Thr Tyr Asp Ser Pro Tyr Pro Leu Tyr Ala Met Ala Phe Ser Ser Leu
            20                  25                  30

Arg Ser Ser Ser Gly His Arg Ile Ala Val Gly Ser Phe Leu Glu Asp
        35                  40                  45

Tyr Asn Asn Arg Ile Asp Ile Leu Ser Phe Asp Ser Asp Ser Met Thr
    50                  55                  60

Val Lys Pro Leu Pro Asn Leu Ser Phe Glu His Pro Tyr Pro Pro Thr
65                  70                  75                  80

Lys Leu Met Phe Ser Pro Ser Leu Arg Arg Pro Ser Ser Gly Asp
                85                  90                  95

Leu Leu Ala Ser Ser Gly Asp Phe Leu Arg Leu Trp Glu Ile Asn Glu
            100                 105                 110

Asp Ser Ser Thr Val Glu Pro Ile Ser Val Leu Asn Asn Ser Lys Thr
        115                 120                 125

Ser Glu Phe Cys Ala Pro Leu Thr Ser Phe Asp Trp Asn Asp Val Glu
    130                 135                 140

Pro Lys Arg Leu Gly Thr Cys Ser Ile Asp Thr Thr Cys Thr Ile Trp
145                 150                 155                 160

Asp Ile Glu Lys Ser Val Val Glu Thr Gln Leu Ile Ala His Asp Lys
                165                 170                 175

Glu Val His Asp Ile Ala Trp Gly Glu Ala Arg Val Phe Ala Ser Val
            180                 185                 190

Ser Ala Asp Gly Ser Val Arg Ile Phe Asp Leu Arg Asp Lys Glu His
        195                 200                 205

Ser Thr Ile Ile Tyr Glu Ser Pro Gln Pro Asp Thr Pro Leu Leu Arg
    210                 215                 220

Leu Ala Trp Asn Lys Gln Asp Leu Arg Tyr Met Ala Thr Ile Leu Met
225                 230                 235                 240

Asp Ser Asn Lys Val Val Ile Leu Asp Ile Arg Ser Pro Thr Met Pro
                245                 250                 255

Val Ala Glu Leu Glu Arg His Gln Ala Ser Val Asn Ala Ile Ala Trp
            260                 265                 270

Ala Pro Gln Ser Cys Lys His Ile Cys Ser Gly Gly Asp Asp Thr Gln
        275                 280                 285

Ala Leu Ile Trp Glu Leu Pro Thr Val Ala Gly Pro Asn Gly Ile Asp
    290                 295                 300

Pro Met Ser Val Tyr Ser Ala Gly Ser Glu Ile Asn Gln Leu Gln Trp
305                 310                 315                 320

Ser Ser Ser Gln Pro Asp Trp Ile Gly Ile Ala Phe Ala Asn Lys Met
                325                 330                 335

Gln Leu Leu Arg Val
            340

<210> SEQ ID NO 21
<211> LENGTH: 1639
<212> TYPE: DNA
<213> ORGANISM: Arabidopsis thaliana

<400> SEQUENCE: 21

```
agggaaaaaa aaaacagagg aactaataaa cggaccatga gctccacaga gacatacgag      60
ccgttattga cacgactcca ctcggattct cagataactg aacggtcttc gccagagata     120
gaggagtttc tccgccgtcg tggatccaca gtgacaccac ggtggtggct aaagctggca     180
gtgtgggagt caaagcttct atggacactc tctggagcct ctatagtggt ctctgttctg     240
aattacatgc tcagcttcgt caccgtcatg ttcaccggtc atctcggttc tcttcagctc     300
gccggcgctt ccatcgccac cgtcggaatc caaggcctag cttacggtat catgttagga     360
atggcgagcg cggtccaaac agtgtgtggt caagcgtacg gagcgagaca gtactcatca     420
atgggaataa tctgccaacg agccatggtc ttgcaccttg cagctgcagt cttcctcacg     480
ttcctctact ggtactcggg tccaatcctt aaaacaatgg ccaatccgt agccatagca      540
cacgagggtc agatctttgc acgtggaatg attccacaaa tttacgcatt gccctcgct     600
tgcccgatgc agaggtttct tcaggctcag aacatagtga acccttggc ttacatgtcc      660
ttaggagttt tcttgctcca cacgttactc acgtggctgg ttaccaacgt gctggatttc     720
ggcttgcttg gggcggctct gattctcagt ttctcatggt ggctgctagt agctgtgaat     780
ggtatgtata tcttgatgag cccgaattgt aaggagacat ggacagggtt ttcaacgagg     840
gcatttagag ggatatggcc ttacttcaag ctcacggtag cttcagcagt tatgctatgt     900
ttggagatat ggtacaacca agggctagtg attatctctg gtttactctc caatccgaca     960
atttctctag acgctatttc gatttgcatg tattacttga attgggatat gcagttcatg    1020
cttggtctaa gtgcagcaat cagtgtgcga gtgagcaatg agctaggagc gggaaatcca    1080
cgagtggcta tgttatcagt agtggttgtc aacatcacga ctgttctcat cagctcagtt    1140
ctctgtgtca tcgtgcttgt gttccgcgtt ggccttagca aagccttcac cagcgatgca    1200
gaagttatag cagccgtctc tgacctcttt cctcttctcg ccgtttccat tttcttaaac    1260
ggaatccagc caattctctc tggggttgct attgggagtg ggtggcaagc agtggtggct    1320
tatgtgaatc ttgttacgta ctatgtcatt ggtcttccta ttggctgtgt ccttggcttc    1380
aaaaccagtc ttggagttgc tgggatctgg tggggatga ttgcaggagt catacttcaa     1440
accctaactt tgattgttct tacacttaaa actaattgga cttccgaggt agaaaatgca    1500
gctcagagag taaagacttc ggcaactgag aatcaagaga tggctaacgc aggtgtttaa    1560
gataacagca acagtgactc tgttttttttt cccctctttt ggtgaaaaga gatataagat    1620
gaaaaaaaaa aaaaaaaa                                                   1639
```

<210> SEQ ID NO 22
<211> LENGTH: 507
<212> TYPE: PRT
<213> ORGANISM: Arabidopsis thaliana

<400> SEQUENCE: 22

```
Met Ser Ser Thr Glu Thr Tyr Glu Pro Leu Leu Thr Arg Leu His Ser
 1               5                  10                  15

Asp Ser Gln Ile Thr Glu Arg Ser Ser Pro Glu Ile Glu Glu Phe Leu
            20                  25                  30

Arg Arg Arg Gly Ser Thr Val Thr Pro Arg Trp Leu Lys Leu Ala
        35                  40                  45

Val Trp Glu Ser Lys Leu Leu Trp Thr Leu Ser Gly Ala Ser Ile Val
    50                  55                  60
```

-continued

```
Val Ser Val Leu Asn Tyr Met Leu Ser Phe Val Thr Val Met Phe Thr
 65                  70                  75                  80

Gly His Leu Gly Ser Leu Gln Leu Ala Gly Ala Ser Ile Ala Thr Val
                 85                  90                  95

Gly Ile Gln Gly Leu Ala Tyr Gly Ile Met Leu Gly Met Ala Ser Ala
            100                 105                 110

Val Gln Thr Val Cys Gly Gln Ala Tyr Gly Ala Arg Gln Tyr Ser Ser
        115                 120                 125

Met Gly Ile Ile Cys Gln Arg Ala Met Val Leu His Leu Ala Ala Ala
    130                 135                 140

Val Phe Leu Thr Phe Leu Tyr Trp Tyr Ser Gly Pro Ile Leu Lys Thr
145                 150                 155                 160

Met Gly Gln Ser Val Ala Ile Ala His Glu Gly Gln Ile Phe Ala Arg
                165                 170                 175

Gly Met Ile Pro Gln Ile Tyr Ala Phe Ala Leu Ala Cys Pro Met Gln
            180                 185                 190

Arg Phe Leu Gln Ala Gln Asn Ile Val Asn Pro Leu Ala Tyr Met Ser
        195                 200                 205

Leu Gly Val Phe Leu Leu His Thr Leu Leu Thr Trp Leu Val Thr Asn
210                 215                 220

Val Leu Asp Phe Gly Leu Leu Gly Ala Ala Leu Ile Leu Ser Phe Ser
225                 230                 235                 240

Trp Trp Leu Leu Val Ala Val Asn Gly Met Tyr Ile Leu Met Ser Pro
                245                 250                 255

Asn Cys Lys Glu Thr Trp Thr Gly Phe Ser Thr Arg Ala Phe Arg Gly
            260                 265                 270

Ile Trp Pro Tyr Phe Lys Leu Thr Val Ala Ser Ala Val Met Leu Cys
        275                 280                 285

Leu Glu Ile Trp Tyr Asn Gln Gly Leu Val Ile Ile Ser Gly Leu Leu
    290                 295                 300

Ser Asn Pro Thr Ile Ser Leu Asp Ala Ile Ser Ile Cys Met Tyr Tyr
305                 310                 315                 320

Leu Asn Trp Asp Met Gln Phe Met Leu Gly Leu Ser Ala Ala Ile Ser
                325                 330                 335

Val Arg Val Ser Asn Glu Leu Gly Ala Gly Asn Pro Arg Val Ala Met
            340                 345                 350

Leu Ser Val Val Val Asn Ile Thr Thr Val Leu Ile Ser Ser Val
        355                 360                 365

Leu Cys Val Ile Val Leu Val Phe Arg Val Gly Leu Ser Lys Ala Phe
    370                 375                 380

Thr Ser Asp Ala Glu Val Ile Ala Ala Val Ser Asp Leu Phe Pro Leu
385                 390                 395                 400

Leu Ala Val Ser Ile Phe Leu Asn Gly Ile Gln Pro Ile Leu Ser Gly
                405                 410                 415

Val Ala Ile Gly Ser Gly Trp Gln Ala Val Ala Tyr Val Asn Leu
            420                 425                 430

Val Thr Tyr Tyr Val Ile Gly Leu Pro Ile Gly Cys Val Leu Gly Phe
        435                 440                 445

Lys Thr Ser Leu Gly Val Ala Gly Ile Trp Trp Gly Met Ile Ala Gly
    450                 455                 460

Val Ile Leu Gln Thr Leu Thr Leu Ile Val Leu Thr Leu Lys Thr Asn
465                 470                 475                 480

Trp Thr Ser Glu Val Glu Asn Ala Ala Gln Arg Val Lys Thr Ser Ala
```

```
                485               490               495
Thr Glu Asn Gln Glu Met Ala Asn Ala Gly Val
        500               505

<210> SEQ ID NO 23
<211> LENGTH: 1102
<212> TYPE: DNA
<213> ORGANISM: Arabidopsis thaliana

<400> SEQUENCE: 23
aaaacatttc atctctctcc aacaactatt caccacattc aatggagtca ccaccactat     60
acgagatatc ctcaagctct tcttctgaaa acctagaca ccatttccaa tcccttgatc    120
tcttccctaa cctcaaccaa aactcttgta tcaacaatac cctaattgag cctttaccgc    180
ttattgatcg cataaacttg aactcaaacc tagacctaaa ccctaatccc ttgtatgcgg    240
aagaaggaga gcaagaggag gaagaagaag aagaagaaga ccgtgaagtg gacgtggact    300
tacacatcgg ccttcctggt tttggtaaac caagcaatga tgctaaacag ctgaagaaga    360
gaaatgggaa ggagatcgcc acatatgacg ccggaaaagg catcgagaat gaactttccg    420
gaaaggcata ctggatcccg gcgccggagc aaattctcat agggttcact cattttctt    480
gccatgtatg cttcaagaca ttcaatcgct acaacaatct tcagatgcac atgtggggac    540
atggttcaca atacaggaaa ggaccggagt cactgaaagg cacacagcca cgagccatgt    600
tagggatccc ttgttactgc tgcgttgaag ggtgcaggaa ccacattgac catcctcgtt    660
ccaagccact gaaagacttt aggacgctcc aaacgcacta caaacgcaaa cacggacaca    720
aacccttctc gtgtcgcctt tgcggtaagc ttttggctgt caagggcgat tggcgaacac    780
atgagaagaa ttgtggaaaa cgttgggttt gcgtttgcgg ttctgatttt aaacacaaac    840
gttctcttaa ggaccatgtt aaggcgtttg ggtctggtca tgggccttat ccaactggtt    900
tgtttgaaga gcaggcttct aattcatctg tctccgagac tttgtttttt taaatttggg    960
catcttttc tttcgcttat gaaatatcta tttactttag aaaaataata atgtggtatc   1020
taattgttcc aaattaggaa cacgaagtgt accattatat ttttcatcac tacaaatgtt   1080
attcagagaa aattatcatt aa                                            1102

<210> SEQ ID NO 24
<211> LENGTH: 303
<212> TYPE: PRT
<213> ORGANISM: Arabidopsis thaliana

<400> SEQUENCE: 24

Met Glu Ser Pro Pro Leu Tyr Glu Ile Ser Ser Ser Ser Ser Glu
 1               5                  10                  15

Lys Pro Arg His His Phe Gln Ser Leu Asp Leu Phe Pro Asn Leu Asn
                20                  25                  30

Gln Asn Ser Cys Ile Asn Asn Thr Leu Ile Glu Pro Leu Pro Leu Ile
            35                  40                  45

Asp Arg Ile Asn Leu Asn Ser Asn Leu Asp Leu Asn Pro Asn Pro Leu
        50                  55                  60

Tyr Ala Glu Glu Gly Glu Gln Glu Glu Glu Glu Glu Glu Glu Asp
 65                  70                  75                  80

Arg Glu Val Asp Val Asp Leu His Ile Gly Leu Pro Gly Phe Gly Lys
                85                  90                  95

Pro Ser Asn Asp Ala Lys Gln Leu Lys Lys Arg Asn Gly Lys Glu Ile
            100                 105                 110
```

```
Ala Thr Tyr Asp Ala Gly Lys Gly Ile Glu Asn Glu Leu Ser Gly Lys
        115                 120                 125

Ala Tyr Trp Ile Pro Ala Pro Glu Gln Ile Leu Ile Gly Phe Thr His
        130                 135                 140

Phe Ser Cys His Val Cys Phe Lys Thr Phe Asn Arg Tyr Asn Asn Leu
145                 150                 155                 160

Gln Met His Met Trp Gly His Gly Ser Gln Tyr Arg Lys Gly Pro Glu
                165                 170                 175

Ser Leu Lys Gly Thr Gln Pro Arg Ala Met Leu Gly Ile Pro Cys Tyr
            180                 185                 190

Cys Cys Val Glu Gly Cys Arg Asn His Ile Asp His Pro Arg Ser Lys
        195                 200                 205

Pro Leu Lys Asp Phe Arg Thr Leu Gln Thr His Tyr Lys Arg Lys His
        210                 215                 220

Gly His Lys Pro Phe Ser Cys Arg Leu Cys Gly Lys Leu Leu Ala Val
225                 230                 235                 240

Lys Gly Asp Trp Arg Thr His Glu Lys Asn Cys Gly Lys Arg Trp Val
                245                 250                 255

Cys Val Cys Gly Ser Asp Phe Lys His Lys Arg Ser Leu Lys Asp His
            260                 265                 270

Val Lys Ala Phe Gly Ser Gly His Gly Pro Tyr Pro Thr Gly Leu Phe
        275                 280                 285

Glu Glu Gln Ala Ser Asn Ser Ser Val Ser Glu Thr Leu Phe Phe
        290                 295                 300

<210> SEQ ID NO 25
<211> LENGTH: 950
<212> TYPE: DNA
<213> ORGANISM: Medicago sativa

<400> SEQUENCE: 25
gaattcccat agctaaacaa aaaaaattaa gaacaagaat atggctgcat caatcaccgc     60
aatcactgtg gagaaccttg aatacccagc ggtggttacc tctccggtca ccggcaaatc    120
atatttcctc ggtggcgctg gggagagagg attgaccatt gaaggaaact tcatcaagtt    180
cactgccata ggtgtttatt tggaagatat agcagtggct tcactagctg ccaaatggaa    240
gggtaaatca tctgaagagt tacttgagac ccttgacttt tacagagaca tcatctcagg    300
tccctttgaa aagttaatta gagggtcaaa gattagggaa ttgagtggtc ctgagtactc    360
aaggaaggtt atggagaact gtgtggcaca cttgaaatca gttggaactt atggagatgc    420
agaagctgaa gctatgcaaa aatttgctga agctttcaag cctgttaatt ttccacctgg    480
tgcctctgtt ttctacaggc aatcacctga tggaatatta gggcttagtt tctctccgga    540
tacaagtata ccagaaaagg aggctgcact catagagaac aaggcagttt catcagcagt    600
gttggagact atgatcggcg agcacgctgt ttcccctgat cttaagcgct gtttagctgc    660
aagattacct gcgttgttga acgagggtgc tttcaagatt ggaaactgat gatgattata    720
ctcctatatc actgcatttc caaaagcgtt gcagcacaag aatgagacca tgaacttttt    780
taagtctaca cgtttaattt tttgtatatc tatttacctt cttattagta tcaataatat    840
gaaatgaaag atcttgcttt ctactcttgt actatttctg tgatagataa tgttaatgag    900
tatcttcatc aataaagtg atttgttttg tttgttcaaa aaaaaaaaa                 950

<210> SEQ ID NO 26
```

<211> LENGTH: 836
<212> TYPE: DNA
<213> ORGANISM: Medicago sativa

<400> SEQUENCE: 26

```
caaatcatat ttcctcggtg gcgctggggga gagaggattg accattgaag gaaacttcat      60
caagttcact gccataggtg tttatttgga agatatagca gtggcttcac tagctgccaa     120
atggaagggt aaatcatctg aagagttact tgagacccct tgactttttaca gagacatcat   180
ctcaggtccc tttgaaaagt taattagagg gtcaaagatt agggaattga gtggtcctga     240
gtactcaagg aaggttatgg agaactgtgt ggcacacttg aaatcagttg gaacttatgg     300
agatgcagaa gctgaagcta tgcaaaaatt tgctgaagct ttcaagcctg ttaattttcc     360
acctggtgcc tctgttttct acaggcaatc acctgatgga atattagggc ttagtttctc     420
tccggataca agtataccag aaaaggaggc tgcactcata gagaacaagg cagtttcatc     480
agcagtgttg gagactatga tcggcgaaca cgctgtttcc cctgatctta agcgctgttt     540
ggctgcaaga ttacctgcgt tgttgaacga gggtgctttc aagattggaa actgatgatg     600
attatactct tatataaaaa catttccaaa agcgttgcag cacaagaatg agaccatgga     660
cttttttaag tctacacgtt taatttttttg tatatctatt taccttctta ttagtatcaa    720
tagtatgaaa tgaaagatct tgctttctac tcttgtacta tttctgtgat agataatgtt     780
aatgagtatc ttcatcaata aaagtgattt gttttgtttg ttcaaaaaaa aaaaaa         836
```

<210> SEQ ID NO 27
<211> LENGTH: 1380
<212> TYPE: DNA
<213> ORGANISM: Medicago sativa

<400> SEQUENCE: 27

```
gaattcccaa caaacaagta ctgcaaacca attgagtatt acatagaaac tactagagat      60
accaagatgg tgagtgtatc tgaaattcgc aaggctcaga gggcagaagg tcctgcaacc     120
attttggcca ttggcactgc aaatccagca aattgtgttg aacaaagtac atatcctgat     180
ttttactta aaatcacaaa tagcgagcac aagactgaac tcaaagagaa attccaacgc      240
atgtgtgata atctctatga tcaagaggaga tacatgtacc taacagagga gatttttgaaa 300
gagaatccta gtgtttgtga atatatggca ccttcattgg atgccaggca agacatggtg     360
gtggtagagg tacctagact agggaaggag gctgcagtga aggctataaa agaatggggt     420
caaccaaagt caaagattac tcacttaatt gtttgcacta caagtggtgt agacatgcct     480
ggagctgatt accaactcac aaaactcttg ggtcttcgcc catatgtgaa aaggtatatg     540
atgtaccaac aaggttgctt tgcaggaggc acggtgcttc gtttggctaa agatttggct     600
gagaacaaca aaggtgcccg tgtattggtt gtttgttctg aagtcactgc agtcacattc     660
cgcggcccta gtgatactca cttggacagc cttgttggac aagcactatt tggagacgga    720
gctgctgcac taattgttgg ttctgatcca gtaccagaaa ttgagaaacc tatatttgag     780
atggtttgga ctgcacaaac aattgctcca gatagtgaag gagccattga tggtcacctt     840
cgtgaagctg gactaacatt ccaccttctt aaagatgttc ctgggattgt ttcaaagaac     900
attgataaag cattagttga agctttccaa ccattgggaa tttctgatta caactcaatc     960
ttttggattg cacaccctgg tggccctgca attttagatc aagtagagca aaagttagcc    1020
ttgaagcctg aaaagatgag agccactaga gaagtgctta gtgaatatgg aaatatgtca    1080
agtgcatgtg ttttgtttat cttagatgaa atgagaaaga aatcaactca agatggactg    1140
```

```
aagacaacag gagaaggact tgaatggggt gtgttatttg gctttggacc aggacttacc    1200
atagaaactg ttgttttgcg cagtgtcgct atatgaaatg cttaattatt ttattttttat   1260 ttatcacttt caaatttgct tgattttttat gtaaggatga aaaactcgtc tacagttcaa   1320
catttactgt catattaaaa ataatacaat tgtgattccc tttaaaaaaa aaggaattc     1380

<210> SEQ ID NO 28
<211> LENGTH: 1423
<212> TYPE: DNA
<213> ORGANISM: Medicago sativa

<400> SEQUENCE: 28
cgaattccca actaagtact gtaaaccata gagttcaaat tacagtactt tactttcatt     60
tgataccaac ctaccatatc attgctacac agaaactata tcaagatggt gagtgtatct    120
gaaattcgtc aggctcaaag ggcagaaggc cctgcaacca tcatggccat tggcactgca    180
aatccatcca actgtgttga acaaagcaca tatcctgatt tctacttcaa atcacaaac     240 agtgagcaca aagttgaact caaagagaaa tttcaacgca tgtgtgataa atccatgatc    300
aagaggagat acatgtatct taccgaagag attttgaaag aaaatccaag tgtatgtgaa    360
tacatggcac cttcattgga tgctaggcag gacatggtgg tggtagaggt acctagactt    420
ggaaaggagg ctgcagtgaa ggctataaaa gaatggggcc aaccaaaatc aaagattaca    480
cacttaatat tttgtaccac aagtggtgta gacatgcctg gtgccgatta ccaactcaca    540
aaactcttag gtcttcgtcc atatgtgaaa aggtatatga tgtaccaaca agggtgcttt    600
gcaggtggga cggtccttcg tttggccaag gacttggctg agaacaataa aggtgctcgt    660
gtgttggttg tttgttctga agttactgcg gtgacattcc gtggtcctag tgatactcat    720
ttagacagtc ttgttggaca agcactcttt ggagatggtg ctgctgcact cattgttggt    780
tctgacccaa taccagaaat tgagaaacct atatttgaga tggtttggac tgcacaaaca    840
attgctccag acagtgaagg agccattgat ggtcaccttg tcgaagctgg tctaacattt    900
caccttctta aagatgttcc tgggattgtt tcaaagaaca ttgataaagc attgattgag    960
gctttccaac cattaaacat ctctgattac aattcaatct tctggattgc tcacccaggt   1020
ggacccgcaa ttctagacca agttgaagaa aagttaggct taaaacctga aaagatgaag   1080
gccactaggg aagtacttag tgaatatggt aacatgtcaa gtgcatgtgt attgttcatc   1140
ttagatgaga tgaaaagaa atcggcacaa gcgggactta aaaccacagg agaaggcctt   1200
gactggggtg tgttgtttgg cttcggacct ggacttacca ttgaaaccgt tgttctccat   1260
agcgtggcta tatgaaatga ttgattgttt tattttattg tattactttt aaacttgctt   1320
gaaattccat gtaagaataa atacagagtt catgtaccat ggatgttaaa acgaatatac   1380
catttgtagc ttcttctttt tctcgcaaaa aaaaaaggaa ttc                     1423

<210> SEQ ID NO 29
<211> LENGTH: 1034
<212> TYPE: DNA
<213> ORGANISM: Hordeum vulgare

<400> SEQUENCE: 29
atgtcggcgg gcgaggggag gaagacggcg tgcgtcacgg gagggagcgg ctacatcgct     60
tcggcgctca tcaagctgct gctcgagaag ggctacgccg tcaagaccac cgtcagaaac    120
cccgatgaca tggagaagaa ctcccacctc aaagacctgc agcaaacgct tgggcccttg    180
```

-continued

```
gagatcatcc gtgccgatct gaatgaagaa ggcagcttcg acgaagctgt ttctggctgc    240
gactacgtct tcctcgtcgc cgctccggtg aacatgttgt ctgaagatcc tgagagagat    300
gtgatcgaac cgcgggttca aggaacgctc aacgtgatga ggtcgtgcgc gagagcaggc    360
acggtgaagc gcgtgatcct gacgtcgtcg aacgccgggg tgtccaggag gccgctgcag    420
ggcggcggcc acgtgctgga cgagagctcc tggtccgacg tcgagtatct cagagccaac    480
aagccaccaa cttgggcata cggggtgtcg aaggtgcttc tggagaaggc ggcgagcgaa    540
ttcgcggagg agaagggcat cagcctcgtc accgtgttgc ccgtgaccac actgggcgcg    600
gcgccggtcg ccaaagcaag atccagcgtt cccgtcgtcc tctccttgtt gtctggcgac    660
gaagcgcggc tgacaatcct gaaaggcgtg cagtctgtca ccggttccgt gtcgataatt    720
cacgtggagg atctctgccg cgccgaggtg ttcgtcgcgg agaacgagac ctcgtcgggg    780
aggtacatgt gctgcagcca acaccaccc gtcgtgcaga tcacccgtct cctggcagaa    840
aaattcccgc agtacaacgt gaatgcccaa cgattcgctg gatgcccga ggaaccgaga    900 gtgcgcatgt cgtctcagaa gctcgtcgga aagggtttg ccttcaagca tgagtgcctt    960
ggtgagatat tcgatgacgt tgtcgagtat ggaaggagca ccgggatttt gcgccattga   1020
catgttctag atct                                                    1034
```

<210> SEQ ID NO 30
<211> LENGTH: 338
<212> TYPE: PRT
<213> ORGANISM: Hordeum vulgare

<400> SEQUENCE: 30

Met Ser Ala Gly Glu Gly Arg Lys Thr Ala Cys Val Thr Gly Gly Ser
1               5                   10                  15

Gly Tyr Ile Ala Ser Ala Leu Ile Lys Leu Leu Leu Glu Lys Gly Tyr
                20                  25                  30

Ala Val Lys Thr Thr Val Arg Asn Pro Asp Met Glu Lys Asn Ser His
            35                  40                  45

Leu Lys Asp Leu Gln Gln Thr Leu Gly Pro Leu Glu Ile Ile Arg Ala
        50                  55                  60

Asp Leu Asn Glu Glu Gly Ser Phe Asp Glu Ala Val Ser Gly Cys Asp
65                  70                  75                  80

Tyr Val Phe Leu Val Ala Ala Pro Val Asn Met Leu Ser Glu Asp Pro
                85                  90                  95

Glu Arg Asp Val Ile Glu Pro Ala Val Gln Gly Thr Leu Asn Val Met
            100                 105                 110

Arg Ser Cys Ala Arg Ala Gly Thr Val Lys Arg Val Ile Leu Thr Ser
        115                 120                 125

Ser Asn Ala Gly Val Ser Arg Arg Pro Leu Gln Gly Gly His Val
    130                 135                 140

Leu Asp Glu Ser Ser Trp Ser Asp Val Glu Tyr Leu Arg Ala Asn Lys
145                 150                 155                 160

Pro Pro Thr Trp Ala Tyr Gly Val Ser Lys Val Leu Leu Glu Lys Ala
                165                 170                 175

Ala Ser Glu Phe Ala Glu Glu Lys Gly Ile Ser Leu Val Thr Val Leu
            180                 185                 190

Pro Val Thr Thr Leu Gly Ala Ala Pro Val Ala Lys Ala Arg Ser Ser
        195                 200                 205

Val Pro Val Val Leu Ser Leu Leu Ser Gly Asp Glu Ala Arg Leu Thr
    210                 215                 220

```
Ile Leu Lys Gly Val Gln Ser Val Thr Gly Ser Val Ser Ile Ile His
225                 230                 235                 240

Val Glu Asp Leu Cys Arg Ala Glu Val Phe Val Ala Glu Asn Glu Thr
            245                 250                 255

Ser Ser Gly Arg Tyr Met Cys Cys Ser His Asn Thr Thr Val Val Gln
        260                 265                 270

Ile Thr Arg Leu Leu Ala Glu Lys Phe Pro Gln Tyr Asn Val Asn Ala
    275                 280                 285

Gln Arg Phe Ala Gly Cys Pro Glu Glu Pro Arg Val Arg Met Ser Ser
290                 295                 300

Gln Lys Leu Val Gly Glu Gly Phe Ala Phe Lys His Glu Cys Leu Gly
305                 310                 315                 320

Glu Ile Phe Asp Asp Val Val Glu Tyr Gly Arg Ser Thr Gly Ile Leu
                325                 330                 335

Arg His

<210> SEQ ID NO 31
<211> LENGTH: 1053
<212> TYPE: DNA
<213> ORGANISM: Hordeum vulgare

<400> SEQUENCE: 31
atggcggcgg cggctggtga tgggacgacg aggaggaaga cggcgtgcgt caccggaggg      60
agcgggtaca tcgcgtcggc tctcgtcaag atgctgctgg agaagggcta cgccgtgaag     120
acgacggtca ggaaccccga tgacggggag aagaacgcgc atctcaagac cctggcggcg     180
ctcggccccc tggaggtctt ccgcgccgac ctgaacgaag agggcagctt cgacgacgcc     240
gtcgccggct gcgactacgc cttcctcgtc gccgctccgg tggccctcat gccagagaac     300
gccgaggaag aagtgatcca gccggcgatt caaggaaccc tcaacgtgat gaggtcatgc     360
gtgaaggcgg ggacggtgaa gcgcgtggtc ctcacatcgt cgacggccgc gatctccagc     420
cggccgctgg aaggcgacgg ccatgtcctg gacgaggatt cctggtccga cgtcgagtac     480
ctcagggcca ccaagagcgg tacctgggcg taccctgcct cgaaggtgct ggcggagaag     540
gcggcgatgg cgctcgcgga ggagaagggc ctcagcctgg tgaccgtgtg ccccgtggtc     600
gtcgtcggcg gggcaccggt cagcaaggtc aagaccagcg tccccgaggt cctctccttg     660
ctctccggcg acgacgacat ggtggacaac ctggagctca tcgagaaggc atcggggtcg     720
atcccgctgg tgcacatcga cgacgtgagc cgcgccgaga tattcgccgc cgaggaggcc     780
acgtcggggc ggtacatcgt gtgcacccct aacaccaccg ccgtggcgct cgcccacttc     840
ctggcggcca agtacccgca gtacgagatc aacgacgacc gcattggtca tcttccggag     900
aagccgaggg tgagcatctg gtcggacaag ctcatcaagg aggggttcga gtacaagtac     960
aagaacctgg acgagatata cgacgacctc gtcgtctacg caggaccct gggactcctt    1020
aaatactgat ataacaggct cttctctaga tct                                 1053

<210> SEQ ID NO 32
<211> LENGTH: 342
<212> TYPE: PRT
<213> ORGANISM: Hordeum vulgare

<400> SEQUENCE: 32

Met Ala Ala Ala Ala Gly Asp Gly Thr Thr Arg Arg Lys Thr Ala Cys
1               5                   10                  15
```

```
Val Thr Gly Gly Ser Gly Tyr Ile Ala Ser Ala Leu Val Lys Met Leu
            20                  25                  30

Leu Glu Lys Gly Tyr Ala Val Lys Thr Thr Val Arg Asn Pro Asp Asp
        35                  40                  45

Gly Glu Lys Asn Ala His Leu Lys Thr Leu Ala Ala Leu Gly Pro Leu
        50                  55                  60

Glu Val Phe Arg Ala Asp Leu Asn Glu Glu Gly Ser Phe Asp Asp Ala
65                  70                  75                  80

Val Ala Gly Cys Asp Tyr Ala Phe Leu Val Ala Pro Val Ala Leu
                85                  90                  95

Met Pro Glu Asn Ala Glu Glu Val Ile Gln Pro Ala Ile Gln Gly
                100                 105                 110

Thr Leu Asn Val Met Arg Ser Cys Val Lys Ala Gly Thr Val Lys Arg
            115                 120                 125

Val Val Leu Thr Ser Ser Thr Ala Ala Ile Ser Ser Arg Pro Leu Glu
130                 135                 140

Gly Asp Gly His Val Leu Asp Glu Asp Ser Trp Ser Asp Val Glu Tyr
145                 150                 155                 160

Leu Arg Ala Thr Lys Ser Gly Thr Trp Ala Tyr Pro Ala Ser Lys Val
                165                 170                 175

Leu Ala Glu Lys Ala Ala Met Ala Leu Ala Glu Glu Lys Gly Leu Ser
                180                 185                 190

Leu Val Thr Val Cys Pro Val Val Val Gly Gly Ala Pro Val Ser
                195                 200                 205

Lys Val Lys Thr Ser Val Pro Glu Val Leu Ser Leu Leu Ser Gly Asp
        210                 215                 220

Asp Asp Met Val Asp Asn Leu Glu Leu Ile Glu Lys Ala Ser Gly Ser
225                 230                 235                 240

Ile Pro Leu Val His Ile Asp Asp Val Ser Arg Ala Glu Ile Phe Ala
                245                 250                 255

Ala Glu Glu Ala Thr Ser Gly Arg Tyr Ile Val Cys Thr Leu Asn Thr
                260                 265                 270

Thr Ala Val Ala Leu Ala His Phe Leu Ala Ala Lys Tyr Pro Gln Tyr
                275                 280                 285

Glu Ile Asn Asp Asp Arg Ile Gly His Leu Pro Glu Lys Pro Arg Val
                290                 295                 300

Ser Ile Trp Ser Asp Lys Leu Ile Lys Glu Gly Phe Glu Tyr Lys Tyr
305                 310                 315                 320

Lys Asn Leu Asp Glu Ile Tyr Asp Asp Leu Val Val Tyr Gly Arg Thr
                325                 330                 335

Leu Gly Leu Leu Lys Tyr
            340
```

<210> SEQ ID NO 33
<211> LENGTH: 1053
<212> TYPE: DNA
<213> ORGANISM: Hordeum vulgare
<220> FEATURE:
<221> NAME/KEY: modified_base
<222> LOCATION: (1022)
<223> OTHER INFORMATION: N = A, C, G OR T/U

<400> SEQUENCE: 33
atggcggcgg cggctggtga tgggacgacg aggaggaaga cggcgtgcgt caccggaggg    60
agcgggtaca tcgcgtcggc tctcgtcaag atgctgctgg agaagggcta cgccgtgaag    120

-continued

| | |
|---|---|
| acgacggtca ggaaccccga tgacgggag aagaacgcgc atctcaagac cctggcggcg | 180 |
| ctcggccccc tggaggtctt ccgcgccgac ctgaacgaag agggcagctt cgacgacgcc | 240 |
| gtcgccggct gcgactacgc cttcctcgtc gccgctccgg tggccctcat gccagagaac | 300 |
| gccgaggaag aagtgatcca gccggcgatt caaggaaccc tcaacgtgat gaggtcgtgc | 360 |
| gtgaaggcgg ggacggtgaa gcgcgtggtc ctcacatcgt cgacggccgc gatctccagc | 420 |
| cggccgctgg aaggcgacgg ccatgtcctg gacgaggatt cctggtccga cgtcgagtac | 480 |
| ctcagggcca ccaagagcgg tacctgggcg taccctgcct cgaaggtgct ggcggagaag | 540 |
| gcggcgatgg cgttcgcgga ggagaatggc ctcagcctgg tgaccgtgtg ccccgtggtc | 600 |
| gtcgtcggcg gggcaccggc cagcaaggtc aagaccagcg tccccgaggt cctctccttg | 660 |
| ctctccggcg acgacgacat ggtggacaac ctggagctca tcgagaaggc gacggggtcg | 720 |
| atcccgctgg tgcacatcga cgacgtgagc cgcgccgaga tattcgccga cgaagaggcc | 780 |
| aaatcggggc ggtacatcgt gtgcaccctc aacaccaccg ccgtggcgct cgcccacttc | 840 |
| ctggcggcca agtacccgca gtacgagatc aacgacgacc gcattggtca tcttccggag | 900 |
| aagccgaggg tgagcatctg gtcggacaag ctcatcaagg aggggttcga atacaagtac | 960 |
| aagaacctgg acgagatata cgacgacctc gtcgtctacg gcaggaccct gggactcctt | 1020 |
| anatactgat ataacaggct cttctctaga tct | 1053 |

<210> SEQ ID NO 34
<211> LENGTH: 342
<212> TYPE: PRT
<213> ORGANISM: Hordeum vulgare
<220> FEATURE:
<221> NAME/KEY: MOD_RES
<222> LOCATION: (341)
<223> OTHER INFORMATION: X = ANYTHING

<400> SEQUENCE: 34

```
Met Ala Ala Ala Ala Gly Asp Gly Thr Thr Arg Arg Lys Thr Ala Cys
  1               5                  10                  15

Val Thr Gly Gly Ser Gly Tyr Ile Ala Ser Ala Leu Val Lys Met Leu
             20                  25                  30

Leu Glu Lys Gly Tyr Ala Val Lys Thr Thr Val Arg Asn Pro Asp Asp
         35                  40                  45

Gly Glu Lys Asn Ala His Leu Lys Thr Leu Ala Ala Leu Gly Pro Leu
     50                  55                  60

Glu Val Phe Arg Ala Asp Leu Asn Glu Glu Gly Ser Phe Asp Asp Ala
 65                  70                  75                  80

Val Ala Gly Cys Asp Tyr Ala Phe Leu Val Ala Ala Pro Val Ala Leu
                 85                  90                  95

Met Pro Glu Asn Ala Glu Glu Val Ile Gln Pro Ala Ile Gln Gly
            100                 105                 110

Thr Leu Asn Val Met Arg Ser Cys Val Lys Ala Gly Thr Val Lys Arg
        115                 120                 125

Val Val Leu Thr Ser Ser Thr Ala Ala Ile Ser Arg Pro Leu Glu
    130                 135                 140

Gly Asp Gly His Val Leu Asp Glu Asp Ser Trp Ser Asp Val Glu Tyr
145                 150                 155                 160

Leu Arg Ala Thr Lys Ser Gly Thr Trp Ala Tyr Pro Ala Ser Lys Val
                165                 170                 175

Leu Ala Glu Lys Ala Ala Met Ala Phe Ala Glu Glu Asn Gly Leu Ser
            180                 185                 190
```

Leu Val Thr Val Cys Pro Val Val Val Gly Gly Ala Pro Ala Ser
            195                 200                 205

Lys Val Lys Thr Ser Val Pro Glu Val Leu Ser Leu Leu Ser Gly Asp
        210                 215                 220

Asp Asp Met Val Asp Asn Leu Glu Leu Ile Glu Lys Ala Thr Gly Ser
225                 230                 235                 240

Ile Pro Leu Val His Ile Asp Asp Val Ser Arg Ala Glu Ile Phe Ala
                245                 250                 255

Asp Glu Glu Ala Lys Ser Gly Arg Tyr Ile Val Cys Thr Leu Asn Thr
            260                 265                 270

Thr Ala Val Ala Leu Ala His Phe Leu Ala Ala Lys Tyr Pro Gln Tyr
        275                 280                 285

Glu Ile Asn Asp Asp Arg Ile Gly His Leu Pro Glu Lys Pro Arg Val
    290                 295                 300

Ser Ile Trp Ser Asp Lys Leu Ile Lys Glu Gly Phe Glu Tyr Lys Tyr
305                 310                 315                 320

Lys Asn Leu Asp Glu Ile Tyr Asp Asp Leu Val Val Tyr Gly Arg Thr
                325                 330                 335

Leu Gly Leu Leu Xaa Tyr
            340

<210> SEQ ID NO 35
<211> LENGTH: 1034
<212> TYPE: DNA
<213> ORGANISM: Hordeum vulgare

<400> SEQUENCE: 35
atgtcggcgg gcgaggggag gaagacggcg tgcgtcacgg gagggagcgg ctacatcgct      60
tcggcgctca tcaagctgct gctcgagaag ggctacgccg tcaagaccac cgtcagaaac     120
cccgatgaca tggagaagaa ctcccacctc aaagacctgc agcaaacgct gggcccttg      180
gagatcatcc gtgccgatct gaatgaagaa ggcagcttcg acgaagctgt ttctggctgc     240
gactacgtct cctcgttgc cgctccggtg aacatgttgt ctgaagatcc tgagagagat     300
gtgatcgaac cgctgtgca aggaacgctc aacgtgatga ggtcgtgcgc gagagcaggc     360
acggtgaagc gcgtgatcct gacgtcgtcg aacgccgggg tgtccaggag gccgctgcag     420
ggcggcggcc acgtgctgga cgagagctcc tggtccgacg tcgagtatct cagagccaac     480
aagccaccaa cttgggcata cggggtgtcg aaggtgcttc tggagaaggc ggcgagcgaa     540
ttcgcggagg agaagggcat cagcctcgtc accgtgttgc ccgtgaccac actgggcgcg     600
gcgccggtcg ccaaagcaag atccagcgtt ccgtcgtcc tctccttgtt gtctggcgac     660
gaagcgcggc tgacaatcct gaaaggcgtg cagtctgtca ccggttccgt gtcgataatt     720
cacgtggagg atctctgccg cgccgaggtg ttcgtcgcgg agaacgagac ctcgtcgggg     780
aggtacatgt gctgcagcca caactccacc gtcgtgcaga tcacccgtct tctggcggaa     840
aaattcccgc agtacaacgt gaatgcccaa cgattcgctg gatgccccga ggaaccgaga     900
gtgcgcatgt cgtctcagaa gctcgtcgga gaagggtttg tcttcaagca tgagtgcctt     960
ggtgagatat cgatgacgt tgtcgagtat ggaaggagca ccgggatttt gcgccattga    1020
catgttctag atct                                                      1034

<210> SEQ ID NO 36
<211> LENGTH: 288
<212> TYPE: PRT

<213> ORGANISM: Hordeum vulgare

<400> SEQUENCE: 36

```
Met Ser Ala Gly Glu Gly Arg Lys Thr Ala Cys Val Thr Gly Gly Ser
 1               5                  10                  15
Gly Tyr Ile Ala Ser Ala Leu Ile Lys Leu Leu Leu Glu Lys Gly Tyr
             20                  25                  30
Ala Val Lys Thr Thr Val Arg Asn Pro Asp Asp Met Glu Lys Asn Ser
         35                  40                  45
His Leu Lys Asp Leu Gln Gln Thr Leu Gly Pro Leu Glu Ile Ile Arg
     50                  55                  60
Ala Asp Leu Asn Glu Glu Gly Ser Phe Asp Glu Ala Val Ser Gly Cys
 65                  70                  75                  80
Asp Tyr Val Phe Leu Val Ala Ala Pro Val Asn Met Leu Ser Glu Asp
                 85                  90                  95
Pro Glu Arg Asp Val Ile Glu Pro Ala Val Gln Gly Thr Leu Asn Val
            100                 105                 110
Met Arg Ser Cys Ala Arg Ala Gly Thr Val Lys Arg Val Ile Leu Thr
        115                 120                 125
Ser Ser Asn Ala Gly Val Ser Arg Arg Pro Leu Gln Gly Gly His
    130                 135                 140
Val Leu Asp Glu Ser Ser Trp Ser Asp Val Glu Tyr Leu Arg Ala Asn
145                 150                 155                 160
Lys Pro Pro Thr Trp Ala Tyr Gly Val Ser Lys Val Leu Leu Glu Lys
                165                 170                 175
Ala Ala Ser Glu Phe Ala Glu Glu Lys Gly Ile Ser Leu Val Thr Val
            180                 185                 190
Leu Pro Val Thr Thr Leu Gly Ala Ala Pro Val Ala Lys Ala Arg Ser
        195                 200                 205
Ser Val Pro Val Leu Ser Leu Leu Ser Gly Asp Glu Ala Arg Leu
    210                 215                 220
Thr Ile Leu Lys Gly Val Gln Ser Val Thr Gly Ser Val Ser Ile Ile
225                 230                 235                 240
His Val Glu Asp Leu Cys Arg Ala Glu Val Phe Val Ala Glu Asn Glu
                245                 250                 255
Thr Ser Ser Gly Arg Tyr Met Cys Cys Ser His Asn Ser Thr Val Val
            260                 265                 270
Gln Ile Thr Arg Leu Leu Ala Glu Lys Phe Pro Gln Tyr Asn Val Asn
        275                 280                 285
```

<210> SEQ ID NO 37
<211> LENGTH: 780
<212> TYPE: DNA
<213> ORGANISM: Brassica napus

<400> SEQUENCE: 37

```
atcttccatg tcgcaactcc aatcagcttt acatctcaag atcccgaggt caaggtccta      60
aacatatatg tgcatgcttt ttatataaac attttgaatt atcttgtttg tgtttaaata     120
aatgtacaga aagacatgat caaaccagcg gtacaaggag tgatcaacgt gttgaaatct     180
tgcttaaaat cgaactcaat caagcgcgtg atctacactt cttcagctgc tgcggtttct     240
atcaacaacc tttcggaacc tggacttgtg atgaccgaag aaaactggtc tgacgttgat     300
tttctcacaa aggagaagcc gtttaactgg gtaataacaa tttcttgctg cacaagatag     360
gttttttttcc cgactaagtt cagttacctc tctctgtttt atttctaggg ttacccagtc     420
```

```
tcaaagactt tagcagaaaa ggaagcttat aaatttgcgg aagagaataa gattgatctc    480
gttactgtgg ttccagcact catagccgga aactctctcc tctctgatcc tccgagcagt    540
ttatctctct cgatgtcttt aatcactggt aaacatgaat cataatacta tttgaccact    600
tctgttaaag tttcacaatc aagatgattg gttttgttg ttagggaaag aaatgcatct     660
gagcggtctc aaggaaatgc agaagctatc tggatccatc tcgttcatcc acgtggacga    720
cctagctcgt gcacatatgt ttcttgcgga gaaagaaaca gcttctggtc gctacatttg    780

<210> SEQ ID NO 38
<211> LENGTH: 181
<212> TYPE: PRT
<213> ORGANISM: Brassica napus

<400> SEQUENCE: 38

Ile Phe His Val Ala Thr Pro Ile Ser Phe Thr Ser Gln Asp Pro Glu
  1               5                  10                  15

Lys Asp Met Ile Lys Pro Ala Val Gln Gly Val Ile Asn Val Leu Lys
             20                  25                  30

Ser Cys Leu Lys Ser Asn Ser Ile Lys Arg Val Ile Tyr Thr Ser Ser
         35                  40                  45

Ala Ala Ala Val Ser Ile Asn Asn Leu Ser Glu Pro Gly Leu Val Met
     50                  55                  60

Thr Glu Glu Asn Trp Ser Asp Val Asp Phe Leu Thr Lys Leu Lys Pro
 65                  70                  75                  80

Phe Asn Trp Gly Tyr Pro Val Ser Lys Thr Leu Ala Glu Lys Glu Ala
                 85                  90                  95

Tyr Lys Phe Ala Glu Glu Asn Lys Ile Asp Leu Val Thr Val Val Pro
            100                 105                 110

Ala Leu Ile Ala Gly Asn Ser Leu Leu Ser Asp Pro Pro Ser Ser Leu
        115                 120                 125

Ser Leu Ser Met Ser Leu Ile Thr Gly Lys Glu Met His Leu Ser Gly
    130                 135                 140

Leu Lys Glu Met Gln Lys Leu Ser Gly Ser Ile Ser Phe Ile His Val
145                 150                 155                 160

Asp Asp Leu Ala Arg Ala His Met Phe Leu Ala Glu Lys Glu Thr Ala
                165                 170                 175

Ser Gly Arg Tyr Ile
            180

<210> SEQ ID NO 39
<211> LENGTH: 964
<212> TYPE: DNA
<213> ORGANISM: Gossypium arboreum

<400> SEQUENCE: 39
atggccagcc agctcgtagg aacaaagaga gcttgtgtcg tgggtggcag cggattcgtt     60
gcgtcattgc tggtcaagtt gttgctcgaa gatctctcac cttgtaacac tacaagagtt    120
gggagacttg aagatctttc aggcggattt aactgatgaa gggagctttg atgccctat    180 tgctggttgt gaccttgtct tccatgttgc gacacccgtt aactttgctt ctgaagatcc    240
agagaatgac atgatcaaac cagcgactca aggagtggtg aacgttttga agcttgtgc     300 caaagcaaaa acagttaaac gagtggtctt gacatctcgt catgacagag aaagactgga    360
ccgatatcga gttcttatca tcagcaaagc caccaacttg ggggtaccct gcatccaaga    420
```

```
cgttggctga aaaggcagct tggaaatttg ctgaagaaaa caacattgat ctcattacag    480
ttatcccttc tctcatgact ggtccttccc tcaccccaat tgtccccagc agcataggcc    540
ttgctacatc tttgatttca ggcaatgaat tcctcataaa tgctttgaaa ggaatgcaga    600
tgctgtcagg ttcgatctct atcacacatg tggaagacgt atgccgagcc catgtttttc    660
tggctgaaaa agaatctgca tcgggtcgat atatatgcag tgctgtcaat accagtgtgc    720
cagaactagc aaagttcctc aacaaaagat accctgactt caaagtccct accgattttg    780
gagatttccc ctccaaaccc aagttgatca tttcctcaga aagcttatt agcgaaggat     840 tcagctttaa gtatgggatc gaggaaatct acgaccaaac cgtggaatat ttgaagtcta    900
aggggctgct caagtgaagc gctctgacgc ttccccaatg attatggtgt tgactctag    960 atct                                                                 964

<210> SEQ ID NO 40
<211> LENGTH: 338
<212> TYPE: PRT
<213> ORGANISM: Gossypium arboreum

<400> SEQUENCE: 40

Met Ala Ser Gln Leu Val Gly Thr Lys Arg Ala Cys Val Val Gly Gly
  1               5                  10                  15

Ser Gly Phe Val Ala Ser Leu Leu Val Lys Leu Leu Glu Lys Gly
                 20                  25                  30

Phe Ala Val Asn Thr Thr Val Arg Asp Pro Asp Asn Gln Lys Lys Ile
             35                  40                  45

Ser His Leu Val Thr Leu Gln Glu Leu Gly Asp Leu Lys Ile Phe Gln
         50                  55                  60

Ala Asp Leu Thr Asp Glu Gly Ser Phe Asp Ala Pro Ile Ala Gly Cys
 65                  70                  75                  80

Asp Leu Val Phe His Val Ala Thr Pro Val Asn Phe Ala Ser Glu Asp
                 85                  90                  95

Pro Glu Asn Asp Met Glu Thr Ile Lys Pro Ala Thr Gln Gly Val Val
            100                 105                 110

Asn Val Leu Lys Ala Cys Ala Lys Ala Lys Thr Val Lys Arg Val Val
        115                 120                 125

Leu Thr Ser Ser Ala Ala Ala Val Ser Ile Asn Thr Leu Asp Gly Thr
    130                 135                 140

Asp Leu Val Met Thr Glu Lys Asp Trp Thr Asp Ile Glu Phe Leu Ser
145                 150                 155                 160

Ser Ala Lys Pro Pro Thr Trp Gly Tyr Pro Ala Ser Lys Thr Leu Ala
                165                 170                 175

Glu Lys Ala Ala Trp Lys Phe Ala Glu Glu Asn Ile Asp Leu Ile
            180                 185                 190

Thr Val Ile Pro Ser Leu Met Thr Gly Pro Ser Leu Thr Pro Ile Val
        195                 200                 205

Pro Ser Ser Ile Gly Leu Ala Thr Ser Leu Ile Ser Gly Asn Glu Phe
    210                 215                 220

Leu Ile Asn Ala Leu Lys Gly Met Gln Met Leu Ser Gly Ser Ile Ser
225                 230                 235                 240

Ile Thr His Val Glu Asp Val Cys Arg Ala His Val Phe Leu Ala Glu
                245                 250                 255

Lys Glu Ser Ala Ser Gly Arg Tyr Ile Cys Ser Ala Val Asn Thr Ser
            260                 265                 270
```

```
Val Pro Glu Leu Ala Lys Phe Leu Asn Lys Arg Tyr Pro Asp Phe Lys
        275                 280                 285

Val Pro Thr Asp Phe Gly Asp Phe Pro Ser Lys Pro Lys Leu Ile Ile
        290                 295                 300

Ser Ser Glu Lys Leu Ile Ser Glu Gly Phe Ser Phe Lys Tyr Gly Ile
305                 310                 315                 320

Glu Glu Ile Tyr Asp Gln Thr Val Glu Tyr Leu Lys Ser Lys Gly Leu
                325                 330                 335

Leu Lys

<210> SEQ ID NO 41
<211> LENGTH: 1016
<212> TYPE: DNA
<213> ORGANISM: Vitis vinifera

<400> SEQUENCE: 41
atggccaccc agcaccccat cggaaagaag accgcatgtg tcgtcggcgg caccggattt      60
gttgcatctt tgctggttaa gcttttgctg cagaagggct atgctgtcaa caccactgtc     120
agggaccctg acaatcagaa aaagtctctc acctcctag aactacagga gttgggtgac      180
ctaaaaatct ttcgagcaga tctaactgac gaattgagct ttgaggcccc tatagcaggt     240
tgcgactttg tcttccatgt tgctacgccc gtccactttg cttctgaaga tccagagaat     300
gacatgatca agccagcaat tcaaggagta gtgaatgtca tgaaagcttg tacaagggca     360
aaatcagtta acgagtcat tttgacatcc tctgcagctg ctgttaccat caatcagctt      420
gatgggacag gtctggttgt ggatgagaag aactggactg atattgagtt cttgacttcc     480
gcgaagccac tacttgggg ctatcctgcc tccaagacac tagctgagaa gcagcttgg      540 aaatttgccg aagaaaataa cattgatctg atcactgtca tccctactct gatggccggt     600
tcctctctta cttcagatgt ccccagcagc attggacttg caatgtcctt gattacaggg     660
aatgaattcc tcataaacgg tatgaagggt atgcagatgc tgtcaggttc agtctccatt     720
gcacatgtgg aagatgtttg ccaggcacat atatttgtag ctgagaaaga atcagcttct     780
ggccgataca tctgctgtgc tgccaatacc agtgttcctg agctagcaaa gttcctgagc     840
aaaagatacc ctcagtacaa agtcccaact gattttggag acttccccc taaatcgaag      900 ttgataatct cctcagagaa gcttgtgaaa gaggggttca gttttaagta cgggattgaa     960
gaaatttatg atgaaagtgt ggagtatttc aaggccaagg gctattgca gaattg       1016

<210> SEQ ID NO 42
<211> LENGTH: 338
<212> TYPE: PRT
<213> ORGANISM: Vitis vinifera

<400> SEQUENCE: 42

Met Ala Thr Gln His Pro Ile Gly Lys Lys Thr Ala Cys Val Val Gly
  1               5                  10                  15

Gly Thr Gly Phe Val Ala Ser Leu Leu Val Lys Leu Leu Leu Gln Lys
                 20                  25                  30

Gly Tyr Ala Val Asn Thr Thr Val Arg Asp Pro Asp Asn Gln Lys Lys
             35                  40                  45

Val Ser His Leu Leu Glu Leu Gln Glu Leu Gly Asp Leu Lys Ile Phe
         50                  55                  60

Arg Ala Asp Leu Thr Asp Glu Leu Ser Phe Glu Ala Pro Ile Ala Gly
 65                  70                  75                  80
```

```
Cys Asp Phe Val Phe His Val Ala Thr Pro Val His Phe Ala Ser Glu
                85                  90                  95
Asp Pro Glu Asn Asp Met Ile Lys Pro Ala Ile Gln Gly Val Val Asn
            100                 105                 110
Val Met Lys Ala Cys Thr Arg Ala Lys Ser Val Lys Arg Val Ile Leu
        115                 120                 125
Thr Ser Ser Ala Ala Val Thr Ile Asn Gln Leu Asp Gly Thr Gly
130                 135                 140
Leu Val Val Asp Glu Lys Asn Trp Thr Asp Ile Glu Phe Leu Thr Ser
145                 150                 155                 160
Ala Lys Pro Pro Thr Trp Gly Tyr Pro Ala Ser Lys Thr Leu Ala Glu
                165                 170                 175
Lys Ala Ala Trp Lys Phe Ala Glu Glu Asn Asn Ile Asp Leu Ile Thr
            180                 185                 190
Val Ile Pro Thr Leu Met Ala Gly Ser Ser Leu Thr Ser Asp Val Pro
        195                 200                 205
Ser Ser Ile Gly Leu Ala Met Ser Leu Ile Thr Gly Asn Glu Phe Leu
210                 215                 220
Ile Asn Gly Met Lys Gly Met Gln Met Leu Ser Gly Ser Val Ser Ile
225                 230                 235                 240
Ala His Val Glu Asp Val Cys Gln Ala His Ile Phe Val Ala Glu Lys
                245                 250                 255
Glu Ser Ala Ser Gly Arg Tyr Ile Cys Cys Ala Ala Asn Thr Ser Val
            260                 265                 270
Pro Glu Leu Ala Lys Phe Leu Ser Lys Arg Tyr Pro Gln Tyr Lys Val
        275                 280                 285
Pro Thr Asp Phe Gly Asp Phe Pro Pro Lys Ser Lys Leu Ile Ile Ser
        290                 295                 300
Ser Glu Lys Leu Val Lys Glu Gly Phe Ser Phe Lys Tyr Gly Ile Glu
305                 310                 315                 320
Glu Ile Tyr Asp Glu Ser Val Glu Tyr Phe Lys Ala Lys Gly Leu Leu
                325                 330                 335
Gln Asn

<210> SEQ ID NO 43
<211> LENGTH: 1101
<212> TYPE: DNA
<213> ORGANISM: Sorghum bicolor

<400> SEQUENCE: 43
atgtcgtcgt ccgcgggtaa caagaagacg atgaagacgg cgtgcgttac tggagggagc    60
gggtacatcg gctccgcact catcaagttg ctgctggaga agggctatgc cgtcaagacg   120
acggtcagga accccgatga catggagaag aactcccacc tcaaggacct gcagaagctt   180
ggaccgctaa cggtcttccg cgccgacatg acgaagaag gcagcttcga cgacgctgtc   240
gccggctgcg attacgtctt cctcgtcgcc gccccgctgc acttcgaggc acaggatcca   300
gagaaagagc agatcgagcc ggctatccaa ggaacgctca acacaatgag gtcgtgcgtg   360
aaggccggga cggtgcggcg tgtgatcctg acctcgtcgg tggccgctgt ctacttccgg   420
ccggacctgc taggcgacgg acatgggcat gtgctggacg aggactcctg gtccgacgtc   480
gacttcctca gagcccacaa gccgccaacc tggtcacact gcgtgtccaa ggtgctcctg   540
gagaaggaag cggccggtt cgcggaggag cacggcatta gcctggtcac catcctcccc   600
gtcatcgtcg ttggcgcggc gccggcaccc aaggcccgct ccagcatcgt cgactgcctc   660
```

```
tccatgctgt ccggcgacga ggccgggctc gccatgctca gagccatcca gaagacctcc    720
ggcgaggtgc agctggtcca cgtcgacgac ctctgccgcg ccgagctgtt cctcgcagag    780
aacgcgacgg ccaatgggag gtacatttgc agcagatacc acccgaccct cgtcgagctc    840
gcgactttcc tggcacaaaa gtacccgcag tacggcgtga accaacaga tttcgacgat     900 gaggagaggc cgagagtgac catgtcgttg gagaagctga tccgggaagg gtttgagtac    960
aagcacaaca ccctggaaga gatctacgac aacgtggtcg agtacggcaa ggcattagga   1020
attctgccct actgatatat agatgcccga tttagcttaa ataaatgggc agtatgtcag   1080
tcggacgtat gagtctagag g                                             1101
```

<210> SEQ ID NO 44
<211> LENGTH: 344
<212> TYPE: PRT
<213> ORGANISM: Sorghum bicolor

<400> SEQUENCE: 44

```
Met Ser Ser Ser Ala Gly Asn Lys Lys Thr Met Lys Thr Ala Cys Val
  1               5                  10                  15

Thr Gly Gly Ser Gly Tyr Ile Gly Ser Ala Leu Ile Lys Leu Leu Leu
             20                  25                  30

Glu Lys Gly Tyr Ala Val Lys Thr Thr Val Arg Asn Pro Asp Asp Met
         35                  40                  45

Glu Lys Asn Ser His Leu Lys Asp Leu Gln Lys Leu Gly Pro Leu Thr
     50                  55                  60

Val Phe Arg Ala Asp Met Asp Glu Glu Gly Ser Phe Asp Asp Ala Val
 65                  70                  75                  80

Ala Gly Cys Asp Tyr Val Phe Leu Val Ala Ala Pro Leu His Phe Glu
                 85                  90                  95

Ala Gln Asp Pro Glu Lys Glu Gln Ile Glu Pro Ala Ile Gln Gly Thr
            100                 105                 110

Leu Asn Thr Met Arg Ser Cys Val Lys Ala Gly Thr Val Arg Arg Val
        115                 120                 125

Ile Leu Thr Ser Ser Val Ala Ala Val Tyr Phe Arg Pro Asp Leu Leu
    130                 135                 140

Gly Asp Gly His Gly His Val Leu Asp Glu Asp Ser Trp Ser Asp Val
145                 150                 155                 160

Asp Phe Leu Arg Ala His Lys Pro Pro Thr Trp Ser His Cys Val Ser
                165                 170                 175

Lys Val Leu Leu Glu Lys Glu Ala Gly Arg Phe Ala Glu Glu His Gly
            180                 185                 190

Ile Ser Leu Val Thr Ile Leu Pro Val Ile Val Gly Ala Ala Pro
        195                 200                 205

Ala Pro Lys Ala Arg Ser Ser Ile Val Asp Cys Leu Ser Met Leu Ser
    210                 215                 220

Gly Asp Glu Ala Gly Leu Ala Met Leu Arg Ala Ile Gln Lys Thr Ser
225                 230                 235                 240

Gly Glu Val Gln Leu Val His Val Asp Asp Leu Cys Arg Ala Glu Leu
                245                 250                 255

Phe Leu Ala Glu Asn Ala Thr Ala Asn Gly Arg Tyr Ile Cys Ser Arg
            260                 265                 270

Tyr His Pro Thr Leu Val Glu Leu Ala Thr Phe Leu Ala Gln Lys Tyr
        275                 280                 285
```

```
Pro Gln Tyr Gly Val Lys Pro Thr Asp Phe Asp Asp Glu Glu Arg Pro
    290                 295                 300

Arg Val Thr Met Ser Leu Glu Lys Leu Ile Arg Glu Gly Phe Glu Tyr
305                 310                 315                 320

Lys His Asn Thr Leu Glu Glu Ile Tyr Asp Asn Val Val Glu Tyr Gly
                325                 330                 335

Lys Ala Leu Gly Ile Leu Pro Tyr
            340

<210> SEQ ID NO 45
<211> LENGTH: 1093
<212> TYPE: DNA
<213> ORGANISM: Sorghum bicolor

<400> SEQUENCE: 45
atgtcgtcgt ctgcgcgcaa cacgacgaag ctgaagacgg cgtgcgtgac cggaggaaat      60
ggctacatcg gctccgcgct cattaagatg ctgctggagg aaggctacgc cgtgaagacg     120
acggtcagga accccgatga catggagaag aactcccatc tcaagggctt gcaggagctt     180
ggaccgctga cggtcctccg cgccgacatg gacgaagaag cagcttgga cgacgccgtt      240
gccggctgcg attacgcctt cctcgttgcc gccccggtga acctctgggc gcaggatcca     300
gagaaacagc agatcgagcc gtctgtccga ggaacgctga acgcagtgag gtcgtgcgtg     360
aaggccggga cggtgcggcg cgtgatcctg acctcgtcgg cggccggagt ctacatcagg     420
ccggacctgc aaggcgacgg gcacgcgctg acgaggact cctggtccga cgtcgacttc      480
ctcagagcaa acaagccgcc gacctgggga tactgcgtgt cgaaggtgct cctggagaag     540
gcggcgtgca ggttcgcgga ggagcacggc atcagcctcg tcaccgtctg ccccgtcctc     600
accgtcggcg ccgcgccggc acccaaggtc cgcaccagca tcgtcgacag cctctccatg     660
ctgtctggcg acgaggccgg gctcgccgtg ctcagaggca tcgagacgac ctccggcgct     720
ctgcagctgg tccacatcga cgacctctgc cgcgccgagc tgttcctggc agaggaggcg     780
gcggccggcg ggaggtacat ctgctgcagc ctcaacacga ccgtcgtcga gctcgcgcgt     840
tccctggcac acaagtaccc gcagtaccgc gtgaagacaa atttcgacga cgatgagcat     900
ctcctggaga ggccgagagt gatcatgtcg tcggagaagc tggtccggga agggtttgag     960
tacaggcaca acacgctgga tgagatatac gacaacgtgg tcgagtacgg caaggcatta    1020
ggaattctgc cctactgatt taaactagta caagccatgt cagtaataat tcaagctcga    1080
gtttgaaatg tct                                                        1093

<210> SEQ ID NO 46
<211> LENGTH: 347
<212> TYPE: PRT
<213> ORGANISM: Sorghum bicolor

<400> SEQUENCE: 46

Pro Ala Met Ser Ser Ala Arg Asn Thr Thr Lys Leu Lys Thr Ala
  1               5                  10                  15

Cys Val Thr Gly Gly Asn Gly Tyr Ile Gly Ser Ala Leu Ile Lys Met
                20                  25                  30

Leu Leu Glu Glu Gly Tyr Ala Val Lys Thr Thr Val Arg Asn Pro Asp
            35                  40                  45

Asp Met Glu Lys Asn Ser His Leu Lys Gly Leu Gln Glu Leu Gly Pro
        50                  55                  60

Leu Thr Val Leu Arg Ala Asp Met Asp Glu Glu Gly Ser Leu Asp Asp
```

|   |   |   |   |   | 65  |   |   |   |   | 70  |   |   |   |   | 75  |   |   |   |   | 80  |
|---|---|---|---|---|-----|---|---|---|---|-----|---|---|---|---|-----|---|---|---|---|-----|

Ala Val Ala Gly Cys Asp Tyr Ala Phe Leu Val Ala Ala Pro Val Asn
                   85                   90                   95

Leu Trp Ala Gln Asp Pro Glu Lys Gln Gln Ile Glu Pro Ser Val Arg
        100                 105                 110

Gly Thr Leu Asn Ala Val Arg Ser Cys Val Lys Ala Gly Thr Val Arg
        115                 120                 125

Arg Val Ile Leu Thr Ser Ser Ala Ala Gly Val Tyr Ile Arg Pro Asp
   130                 135                 140

Leu Gln Gly Asp Gly His Ala Leu Asp Glu Asp Ser Trp Ser Asp Val
145                 150                 155               160

Asp Phe Leu Arg Ala Asn Lys Pro Pro Thr Trp Gly Tyr Cys Val Ser
        165                 170                 175

Lys Val Leu Leu Glu Lys Ala Ala Cys Arg Phe Ala Glu Glu His Gly
        180                 185                 190

Ile Ser Leu Val Thr Val Cys Pro Val Leu Thr Val Gly Ala Ala Pro
        195                 200                 205

Ala Pro Lys Val Arg Thr Ser Ile Val Asp Ser Leu Ser Met Leu Ser
   210                 215                 220

Gly Asp Glu Ala Gly Leu Ala Val Leu Arg Gly Ile Glu Thr Thr Ser
225                 230                 235               240

Gly Ala Leu Gln Leu Val His Ile Asp Asp Leu Cys Arg Ala Glu Leu
        245                 250                 255

Phe Leu Ala Glu Glu Ala Ala Gly Gly Arg Tyr Ile Cys Cys Ser
        260                 265                 270

Leu Asn Thr Thr Val Val Glu Leu Ala Arg Phe Leu Ala His Lys Tyr
        275                 280                 285

Pro Gln Tyr Arg Val Lys Thr Asn Phe Asp Asp Glu His Leu Leu
   290                 295                 300

Glu Arg Pro Arg Val Ile Met Ser Ser Glu Lys Leu Val Arg Glu Gly
305                 310                 315               320

Phe Glu Tyr Arg His Asn Thr Leu Asp Glu Ile Tyr Asp Asn Val Val
        325                 330                 335

Glu Tyr Gly Lys Ala Leu Gly Ile Leu Pro Tyr
        340                 345

<210> SEQ ID NO 47
<211> LENGTH: 1029
<212> TYPE: DNA
<213> ORGANISM: Arabidopsis thaliana

<400> SEQUENCE: 47

| atggaccaga | ctcttacaca | caccggatcg | aagaaggctt | gtgtcattgg | tggcacggga | 60 |
| aacttagcct | ctattctcat | caagcatttg | cttcaaagtg | gctacaaagt | taacactaca | 120 |
| gttagagatc | cagaaaacga | gaagaaaata | gctcaccttaa | ggcaacttca | agaacttggc | 180 |
| gacctgaaga | tcttcaaggc | agatttgact | gatgaagaca | gtttcgaatc | ctcattctcc | 240 |
| ggctgtgaat | acatcttcca | tgtcgcaact | ccgatcaact | taaatccga | agatcccgag | 300 |
| aaagacatga | tcaagccggc | gatacaagga | gtgatcaatg | tgttgaaatc | ttgcttaaaa | 360 |
| tcgaaatcag | tcaagcgtgt | gatctacaca | tcttcagctg | ctgctgtttc | catcaacaat | 420 |
| ctttctggaa | ccggactcgt | gatgaacgaa | gaaaactgga | ctgacattga | ttttctcaca | 480 |
| gaggagaagc | cttttaactg | gggttaccca | atctcgaagg | tgctagcaga | aaagaaagct | 540 |

```
tgggaatttg cagaagagaa taagatcaat ctcgtaaccg tgattccggc acttatagcc    600
ggaaactctc tcctctccga tcctccgagc agtttatctc tctcgatgtc tttcatcacc    660
gggaaagaaa tgcatgtgac gggtctcaag gaaatgcaga agctatctgg ctcgatctcg    720
ttcgtgcacg tagacgattt agctcgtgcc catttgtttc ttgcggagaa agaaactgct    780
tctggtcgct acatttgctg tgcttacaac acaagtgttc cagagattgc ggattttctc    840
atacagagat atcctaagta caatgtgttg tccgaattcg aagagggctt gtcgattccg    900
aaattaacac tatcttcgca aaaacttatc aatgaaggct ttcgattcga atatgggatc    960
aatgagatgt atgatcagat gatagagtac ttcgagtcaa aggattgat caaagctaaa    1020 gaatcttga                                                            1029
```

<210> SEQ ID NO 48
<211> LENGTH: 342
<212> TYPE: PRT
<213> ORGANISM: Arabidopsis thaliana

<400> SEQUENCE: 48

```
Met Asp Gln Thr Leu Thr His Thr Gly Ser Lys Lys Ala Cys Val Ile
 1               5                  10                  15

Gly Gly Thr Gly Asn Leu Ala Ser Ile Leu Ile Lys His Leu Leu Gln
            20                  25                  30

Ser Gly Tyr Lys Val Asn Thr Thr Val Arg Asp Pro Glu Asn Glu Lys
        35                  40                  45

Lys Ile Ala His Leu Arg Gln Leu Gln Glu Leu Gly Asp Leu Lys Ile
    50                  55                  60

Phe Lys Ala Asp Leu Thr Asp Glu Asp Ser Phe Glu Ser Ser Phe Ser
65                  70                  75                  80

Gly Cys Glu Tyr Ile Phe His Val Ala Thr Pro Ile Asn Phe Lys Ser
                85                  90                  95

Glu Asp Pro Glu Lys Asp Met Ile Lys Pro Ala Ile Gln Gly Val Ile
            100                 105                 110

Asn Val Leu Lys Ser Cys Leu Lys Ser Lys Ser Val Lys Arg Val Ile
        115                 120                 125

Tyr Thr Ser Ser Ala Ala Ala Val Ser Ile Asn Asn Leu Ser Gly Thr
    130                 135                 140

Gly Leu Val Met Asn Glu Glu Asn Trp Thr Asp Ile Asp Phe Leu Thr
145                 150                 155                 160

Glu Glu Lys Pro Phe Asn Trp Gly Tyr Pro Ile Ser Lys Val Leu Ala
                165                 170                 175

Glu Lys Lys Ala Trp Glu Phe Ala Glu Glu Asn Lys Ile Asn Leu Val
            180                 185                 190

Thr Val Ile Pro Ala Leu Ile Ala Gly Asn Ser Leu Leu Ser Asp Pro
        195                 200                 205

Pro Ser Ser Leu Ser Leu Ser Met Ser Phe Ile Thr Gly Lys Glu Met
    210                 215                 220

His Val Thr Gly Leu Lys Glu Met Gln Lys Leu Ser Gly Ser Ile Ser
225                 230                 235                 240

Phe Val His Val Asp Asp Leu Ala Arg Ala His Leu Phe Leu Ala Glu
                245                 250                 255

Lys Glu Thr Ala Ser Gly Arg Tyr Ile Cys Cys Ala Tyr Asn Thr Ser
            260                 265                 270

Val Pro Glu Ile Ala Asp Phe Leu Ile Gln Arg Tyr Pro Lys Tyr Asn
        275                 280                 285
```

```
Val Leu Ser Glu Phe Glu Glu Gly Leu Ser Ile Pro Lys Leu Thr Leu
    290                 295                 300

Ser Ser Gln Lys Leu Ile Asn Glu Gly Phe Arg Phe Glu Tyr Gly Ile
305                 310                 315                 320

Asn Glu Met Tyr Asp Gln Met Ile Glu Tyr Phe Glu Ser Lys Gly Leu
                325                 330                 335

Ile Lys Ala Lys Glu Ser
            340

<210> SEQ ID NO 49
<211> LENGTH: 52
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
aggctggtgc cacgcggttc ttccatggcg gcgggcgagg ggaggaagac gg          52

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
agatctagaa catgtcaatg gcgcaaaatc ccggtgctc                         39

<210> SEQ ID NO 51
<211> LENGTH: 51
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
caggctggtg ccacgcggtt cttccatggc ggcggcggct ggtgatggga c            51

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52
agatctagag aagagcctgt tatatcagta t                                 31
```